(12) United States Patent
Shilatifard et al.

(10) Patent No.: US 10,308,698 B2
(45) Date of Patent: Jun. 4, 2019

(54) THERAPEUTIC TARGETING OF SET1B/COMPASS PATHWAY FOR TREATING CANCERS

(71) Applicant: Northwestern University, Evanston, IL (US)

(72) Inventors: Ali Shilatifard, Chicago, IL (US); Lu Wang, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/645,282

(22) Filed: Jul. 10, 2017

(65) Prior Publication Data

US 2018/0009870 A1    Jan. 11, 2018

Related U.S. Application Data

(60) Provisional application No. 62/359,978, filed on Jul. 8, 2016.

(51) Int. Cl.
| | |
|---|---|
| *C07K 7/06* | (2006.01) |
| *A61K 38/22* | (2006.01) |
| *C07K 14/47* | (2006.01) |
| *C07K 16/30* | (2006.01) |
| *C07K 14/575* | (2006.01) |
| *C12Q 1/6886* | (2018.01) |

(52) U.S. Cl.
CPC ...... *C07K 14/5759* (2013.01); *A61K 38/2264* (2013.01); *C07K 7/06* (2013.01); *C07K 14/4702* (2013.01); *C07K 16/3015* (2013.01); *C12Q 1/6886* (2013.01); *C12Q 2600/156* (2013.01); *C12Q 2600/158* (2013.01); *C12Q 2600/178* (2013.01)

(58) Field of Classification Search
CPC ............ A61K 38/2264; B60K 17/3505; C07K 14/4702; C07K 14/5759; C07K 16/3015; C07K 7/06; C12Q 1/6886; C12Q 2600/156; C12Q 2600/158; C12Q 2600/178
See application file for complete search history.

(56) References Cited

U.S. PATENT DOCUMENTS

2007/0123451 A1* 5/2007 Mantzoros ........... A61K 31/426
                                                                 514/9.7
2015/0284723 A1* 10/2015 Rice ..................... C12Q 1/6886
                                                                 514/44 A

OTHER PUBLICATIONS

Okada-Iwabu et al. (Applicants' cited IDS: Nature, 503, 2013) (Year: 2013).*
Otvos et al. (BMC Biotechnology, 11:90, 2011) (Year: 2011).*
Lee et al. (J of Diabetes Investigation, 6, 3, May 2015). (Year: 2015).*
Anderson, A.S., Key, T.J., Norat, T., Scoccianti, C., Cecchini, M., Berrino, F., Boutron-Ruault, M.C., Espina, C., Leitzmann, M., Powers, H., et al. (2015). European Code against Cancer 4th Edition: Obesity, body fatness and cancer. Cancer Epidemiol 39 Suppl 1, S34-45.
Bauer, K.R., Brown, M., Cress, R.D., Parise, C.A., and Caggiano, V. (2007). Descriptive analysis of estrogen receptor (ER)-negative, progesterone receptor (PR)-negative, and HER2-negative invasive breast cancer, the so-called triple-negative phenotype: a population-based study from the California cancer Registry. Cancer 109, 1721-1728.
Bledau, A.S., Schmidt, K., Neumann, K., Hill, U., Ciotta, G., Gupta, A., Torres, D.C., Fu, J., Kranz, A., Stewart, A.F., et al. (2014). The H3K4 methyltransferase Setd1a is first required at the epiblast stage, whereas Setd1b becomes essential after gastrulation. Development 141, 1022-1035.
Bremer, K., Kocha, K.M., Snider, T., and Moyes, C.D. (2015). Sensing and responding to energetic stress: The role of the AMPK-PGC1alpha-NRF1 axis in control of mitochondrial biogenesis in fish. Comp Biochem Physiol B Biochem Mol Biol.
Chen, F.X., Woodfin, A.R., Gardini, A., Rickets, R.A., Marshall, S.A., Smith, E.R., Shiekhattar, R., and Shilatifard, A. (2015). PAF1, a Molecular Regulator of Promoter-Proximal Pausing by RNA Polymerase II. Cell 162, 1003-1015.
Cho, Y.W., Hong, T., Hong, S., Guo, H., Yu, H., Kim, D., Guszczynski, T., Dressler, G.R., Copeland, T.D., Kalkum, M., et al. (2007). PTIP associates with MLL3- and MLL4-containing histone H3 lysine 4 methyltransferase complex. The Journal of biological chemistry 282, 20395-20406.
Cociorva, D., D, L.T., and Yates, J.R. (2007). Validation of tandem mass spectrometry database search results using DTASelect. Current protocols in bioinformatics / editoral board, Andreas D. Baxevanis . . . [et al.] Chapter 13, Unit 13 14.
Dent, R., Trudeau, M., Pritchard, K.I., Hanna, W.M., Kahn, H.K., Sawka, C.A., Lickley, L.A., Rawlinson, E., Sun, P., and Narod, S.A. (2007). Triple-negative breast cancer: clinical features and patterns of recurrence. Clin Cancer Res 13, 4429-4434.
Elias, J.E., and Gygi, S.P. (2007). Target-decoy search strategy for increased confidence in large-scale protein identifications by mass spectrometry. Nature methods 4, 207-214.
Eng, J.K., McCormack, A.L., and Yates, J.R. (1994). An approach to correlate tandem mass spectral data of peptides with amino acid sequences in a protein database. Journal of the American Society for Mass Spectrometry 5, 976-989.

(Continued)

*Primary Examiner* — Umamaheswari Ramachandran

(74) *Attorney, Agent, or Firm* — Quarles & Brady LLP

(57) ABSTRACT

Disclosed are methods for treating Set1/COMPASS-associated cancers characterized by expression of Set1B/COMPASS. The methods typically include administering a therapeutic amount of an inhibitor of the Set1B/COMPASS pathway and/or an agonist for a target that is negatively regulated by the Set1B/COMPASS pathway.

2 Claims, 66 Drawing Sheets
Specification includes a Sequence Listing.

(56) References Cited

OTHER PUBLICATIONS

Ferguson, A.D., Larsen, N.A., Howard, T., Pollard, H., Green, I., Grande, C., Cheung, T., Garcia-Arenas, R., Cowen, S., Wu, J., et al. (2011). Structural basis of substrate methylation and inhibition of SMYD2. Structure 19, 1262-1273.

Gathirua-Mwangi, W.G., Zollinger, T.W., Murage, M.J., Pradhan, K.R., and Champion, V.L. (2015). Adult BMI change and risk of Breast Cancer: National Health and Nutrition Examination Survey (NHANES) 2005-2010. Breast Cancer 22, 648-656.

Hamamoto, R., Furukawa, Y., Morita, M., Iimura, Y., Silva, F.P., Li, M., Yagyu, R., and Nakamura, Y. (2004). SMYD3 encodes a histone methyltransferase involved in the proliferation of cancer cells. Nature cell biology 6, 731-740.

He, L., Diedrich, J., Chu, Y.Y., and Yates, J.R., 3rd (2015). Extracting Accurate Precursor Information for Tandem Mass Spectra by RawConverter. Analytical chemistry 87, 11361-11367.

Herz, H.M., Hu, D., and Shilatifard, A. (2014). Enhancer malfunction in cancer. Molecular cell 53, 859-866.

Kandoth, C., McLellan, M.D., Vandin, F., Ye, K., Niu, B., Lu, C., Xie, M., Zhang, Q., McMichael, J.F., Wyczalkowski, M.A., et al. (2013). Mutational landscape and significance across 12 major cancer types. Nature 502, 333-339.

Kershaw, E.E., and Flier, J.S. (2004). Adipose tissue as an endocrine organ. J Clin Endocr Metab 89, 2548-2556.

Klaus, C.R., Iwanowicz, D., Johnston, D., Campbell, C.A., Smith, J.J., Moyer, M.P., Copeland, R.A., Olhava, E.J., Scott, M.P., Pollock, R.M., et al. (2014). DOT1L inhibitor EPZ-5676 displays synergistic antiproliferative activity in combination with standard of care drugs and hypomethylating agents in MLL-rearranged leukemia cells. J Pharmacol Exp Ther 350, 646-656.

Kotake, Y., Cao, R., Viatour, R, Sage, J., Zhang, Y., and Xiong, Y. (2007). pRB family proteins are required for H3K27 trimethylation and Polycomb repression complexes binding to and silencing p16INK4alpha tumor suppressor gene. Genes Dev 21, 49-54.

Kouzarides, T. (2007). Chromatin modifications and their function. Cell 128, 693-705.

Krogan, N.J., Dover, J., Khorrami, S., Greenblatt, J.F., Schneider, J., Johnston, M., and Shilatifard, A. (2002). COMPASS, a histone H3 (Lysine 4) methyltransferase required for telomeric silencing of gene expression. The Journal of biological chemistry 277, 10753-10755.

Kubicek, S., O'Sullivan, R.J., August, E.M., Hickey, E.R., Zhang, Q., Teodoro, M.L., Rea, S., Mechtler, K., Kowalski, J.A., Homon, C.A., et al. (2007). Reversal of H3K9me2 by a small-molecule inhibitor for the G9a histone methyltransferase. Mol Cell 25, 473-481.

Langmead, B., Trapnell, C., Pop, M., and Salzberg, S.L. (2009). Ultrafast and memory-efficient alignment of short DNA sequences to the human genome. Genome biology 10, R25.

Lee, J.H., and Skalnik, D.G. (2012). Rbm15-Mkl1 interacts with the Setd1b histone H3-Lys4 methyltransferase via a SPOC domain that is required for cytokine-independent proliferation. PLoS One 7, e42965.

Lee, J.H., Tate, C.M., You, J.S., and Skalnik, D.G. (2007). Identification and characterization of the human Set1B histone H3-Lys4 methyltransferase complex. The Journal of biological chemistry 282, 13419-13428.

Mazur, P.K., Reynoird, N., Khatri, P., Jansen, P.W., Wilkinson, A.W., Liu, S., Barbash, O., Van Aller, G.S., Huddleston, M., Dhanak, D., et al. (2014). SMYD3 links lysine methylation of MAP3K2 to Ras-driven cancer. Nature 510, 283-287.

Miller, T., Krogan, N.J., Dover, J., Erdjument-Bromage, H., Tempst, P., Johnston, M., Greenblatt, J.F., and Shilatifard, A. (2001). COMPASS: a complex of proteins associated with a trithorax-related SET domain protein. Proceedings of the National Academy of Sciences of the United States of America 98, 12902-12907.

Mohan, M., Herz, H.M., and Shilatifard, A. (2012). SnapShot: Histone lysine methylase complexes. Cell 149, 498-498 e491.

Nagaraju, G.P., Rajitha, B., Aliya, S., Kotipatruni, R.P., Madanraj, A.S., Hammond, A., Park, D., Chigurupati, S., Alam, A., and Pattnaik, S. (2016). The role of adiponectin in obesity-associated female-specific carcinogenesis. Cytokine & growth factor reviews.

Neuhouser, M.L., Aragaki, A.K., Prentice, R.L., Manson, J.E., Chlebowski, R., Carty, C.L., Ochs-Balcom, H.M., Thomson, C.A., Caan, B.J., Tinker, L.F., et al. (2015). Overweight, Obesity, and Postmenopausal Invasive Breast Cancer Risk: A Secondary Analysis of the Women's Health Initiative Randomized Clinical Trials. JAMA Oncol 1, 611-621.

Okada-Iwabu, M., Yamauchi, T., Iwabu, M., Honma, T., Hamagami, K., Matsuda, K., Yamaguchi, M., Tanabe, H., Kimura-Someya, T., Shirouzu, M., et al. (2013). A small-molecule AdipoR agonist for type 2 diabetes and short life in obesity. Nature 503, 493-499.

Pfeiler, G., Hudelist, G., Wulfing, P., Mattsson, B., Konigsberg, R., Kubista, E., and Singer, C.F. (2010). Impact of AdipoR1 expression on breast cancer development. Gynecologic oncology 117, 134-138.

Piunti, A., and Shilatifard, A. (2016). Epigenetic balance of gene expression by Polycomb and COMPASS families. Science 352, aad9780.

Porter, I.M., McClelland, S.E., Khoudoli, G.A., Hunter, C.J., Andersen, J.S., McAinsh, A.D., Blow, J.J., and Swedlow, J.R. (2007). Bod1, a novel kinetochore protein required for chromosome biorientation. The Journal of cell biology 179, 187-197.

Porter, I.M., Schleicher, K., Porter, M., and Swedlow, J.R. (2013). Bod1 regulates protein phosphatase 2A at mitotic kinetochores. Nat Commun 4.

Robinson, M.D., McCarthy, D.J., and Smyth, G.K. (2010). edgeR: a Bioconductor package for differential expression analysis of digital gene expression data. Bioinformatics 26, 139-140.

Rouzier, R., Perou, C.M., Symmans, W.F., Ibrahim, N., Cristofanilli, M., Anderson, K., Hess, K.R., Stec, J., Ayers, M., Wagner, P., et al. (2005). Breast cancer molecular subtypes respond differently to preoperative chemotherapy. Clin Cancer Res 11, 5678-5685.

Salz, T., Deng, C.W., Pampo, C., Siemann, D., Qiu, Y., Brown, K., and Huang, S.M. (2015). Histone Methyltransferase hSETD1A Is a Novel Regulator of Metastasis in Breast Cancer. Mol Cancer Res 13, 461-469.

Salz, T., Li, G., Kaye, F., Zhou, L., Qiu, Y., and Huang, S. (2014). hSETD1A regulates Wnt target genes and controls tumor growth of colorectal cancer cells. Cancer research 74, 775-786.

Shilatifard, A. (2012). The Compass family of histone H3K4 methylases: mechanisms of regulation in development and disease pathogenesis. Annu Rev Biochem 81, 65-95.

Surmacz, E. (2013). Leptin and adiponectin: emerging therapeutic targets in breast cancer. Journal of mammary gland biology and neoplasia 18, 321-332.

Tabb, D.L., McDonald, W.H., and Yates, J.R., 3rd (2002). DTASelect and Contrast: tools for assembling and comparing protein identifications from shotgun proteomics. Journal of proteome research 1, 21-26.

Takahashi, Y.H., Westfield, G.H., Oleskie, A.N., Trievel, R.C., Shilatifard, A., and Skiniotis, G. (2011). Structural analysis of the core Compass family of histone H3K4 methylases from yeast to human. Proceedings of the National Academy of Sciences of the United States of America 108, 20526-20531.

Tang, Z.Y., Chen, W.Y., Shimada, M., Nguyen, U.T.T., Kim, J., Sun, X.J., Sengoku, T., McGinty, R.K., Fernandez, J.P., Muir, T.W., et al. (2013). SET1 and p300 Act Synergistically, through Coupled Histone Modifications, in Transcriptional Activation by p53. Cell 154, 297-310.

Trapnell, C., Pachter, L., and Salzberg, S.L. (2009). TopHat: discovering splice junctions with RNA-Seq. Bioinformatics 25, 1105-1111.

Tripathi, S., Pohl, M.O., Zhou, Y., Rodriguez-Frandsen, A., Wang, G., Stein, D.A., Moulton, H.M., DeJesus, P., Che, J., Mulder, L.C., et al. (2015). Meta- and Orthogonal Integration of Influenza "OMICs" Data Defines a Role for UBR4 in Virus Budding. Cell host & microbe 18, 723-735.

Wu, M., Wang, P.F., Lee, J.S., Martin-Brown, S., Florens, L., Washburn, M., and Shilatifard, A. (2008). Molecular regulation of H3K4 trimethylation by Wdr82, a component of human Set1/COMPASS. Molecular and cellular biology 28, 7337-7344.

(56) References Cited

OTHER PUBLICATIONS

Xu, T., Park, S.K., Venable, J.D., Wohlschlegel, J.A., Diedrich, J.K., Cociorva, D., Lu, B., Liao, L., Hewel, J., Han, X., et al. (2015). ProLuCID: An improved SEQUEST-like algorithm with enhanced sensitivity and specificity. Journal of proteomics 129, 16-24.
Yamauchi, T., Kamon, J., Ito, Y., Tsuchida, A., Yokomizo, T., Kita, S., Sugiyama, T., Miyagishi, M., Hara, K., Tsunoda, M., et al. (2003). Cloning of adiponectin receptors that mediate antidiabetic metabolic effects. Nature 423, 762-769.
Anders et al., "Understanding and Treating Triple-Negative Breast Cancer," Oncology (Williston Park). Oct. 2008; 22(11): 1233-1243.

\* cited by examiner

|  | Cytoplasmic ||
|  | GFP | RBBP5 |
| --- | --- | --- |
| SET1A | 0 | 46 |
| SET1B | 0 | 86 |
| KMT2A | 0 | 0 |
| KMT2B | 0 | 7 |
| KMT2C | 0 | 15 |
| KMT2D | 0 | 21 |

|  | Nuclear ||
|  | GFP | RBBP5 |
| --- | --- | --- |
| SET1A | 0 | 65 |
| SET1B | 0 | 11 |
| KMT2A | 0 | 3 |
| KMT2B | 0 | 16 |
| KMT2C | 0 | 94 |
| KMT2D | 0 | 64 |

B 293T cells
Flag-SET1B transiently transfection

B    PBS    AdipoRon

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Forward CRISPR primer for human SET1B gene
      locus

<400> SEQUENCE: 1 gcttttctt ccggaactgt                                                   20

<210> SEQ ID NO 2
<211> LENGTH: 20
<212> TYPE: DNA
<213> ORGANISM: Artificial
<220> FEATURE:
<223> OTHER INFORMATION: Reverse CRISPR primer for human SET1B gene
      locus

<400> SEQUENCE: 2
gcaggagcag atcatgcttt                                                  20

<210> SEQ ID NO 3
<211> LENGTH: 23
<212> TYPE: DNA
<213> ORGANISM: Artificial
<220> FEATURE:
<223> OTHER INFORMATION: Forward CRISPR primer for AdipoR1 gene locus

<400> SEQUENCE: 3
ccatattgag gtactgtgcc aag                                              23

<210> SEQ ID NO 4
<211> LENGTH: 23
<212> TYPE: DNA
<213> ORGANISM: Artificial
<220> FEATURE:
<223> OTHER INFORMATION: Reverse CRISPR primer for AdipR1 gene locus

<400> SEQUENCE: 4 cctttggac ggtgagctct taa                                               23
```

THERAPEUTIC TARGETING OF SET1B/COMPASS PATHWAY FOR TREATING CANCERS

CROSS-REFERENCE TO RELATED PATENT APPLICATIONS

This application claims the benefit of priority under 35 U.S.C. § 119(e) to U.S. Provisional Patent Application No. 62/359,978, filed on Jul. 8, 2016, the content of which is incorporated herein by reference in its entirety.

STATEMENT REGARDING FEDERALLY SPONSORED RESEARCH OR DEVELOPMENT

This invention was made with government support under R35 CA197569 awarded by the National Institutes of Health. The government has certain rights in the invention.

BACKGROUND

The field of the invention relates to methods for treating cancers. In particular, the field of the invention relates to methods for treating Set1B/COMPASS-associated cancers that are characterized by overexpression of Set1B/COMPASS.

Mutations and translocations within the COMPASS (Complex Proteins Associated with Set1) family of histone lysine methyltransferases are associated with a large number of human diseases including cancer. We have found that Set1B/COMPASS is overexpressed in human breast cancer and that COMPASS overexpression is significantly correlated with ER-negative patients' survival. We also have demonstrated that the depletion of Set1B selectively inhibits multiple triple negative cancer (TNBC) cell survival, but does not affect ER-positive or normal epithelia cell growth. Furthermore, we have demonstrated that the loss of Set1B or Set1B/BOD1 interactions induces activation of the AdipoR1/AMPK signaling pathway, which is hyper-inactivated in both obesity and during TNBC development. Finally, we have identified small molecular agonists for the Set1B/COMPASS target, the Adiponectin receptor 1, and demonstrated that these inhibitors effectively inhibit TNBC cells growth in vitro and in vivo.

SUMMARY

Disclosed are methods for treating Set1B/COMPASS-associated cancers that are characterized by expression of Set1B/COMPASS. The methods typically include administering to the patient a therapeutic amount of an inhibitor of Set1B/COMPASS and/or administering an agonist for a target that is negatively regulated by Set1B/COMPASS. Cancer that are treated by the disclosed methods may include breast cancers, such as ER-negative breast cancer, HER2-negative breast cancer, PR-negative breast cancer, or triple negative breast cancer (TNBC).

The disclosed methods typically include administering to the patient a therapeutic amount of an inhibitor of Set1B/COMPASS pathway and/or an agonist for a target that is negatively regulated by Set1B/COMPASS. In particular, the disclosed methods may include administering to the patient an agonist of an adiponectin receptor to the patient, such as an agonist of adiponectin receptor 1. Suitable agonists may include but are not limited to a compound having a formula:

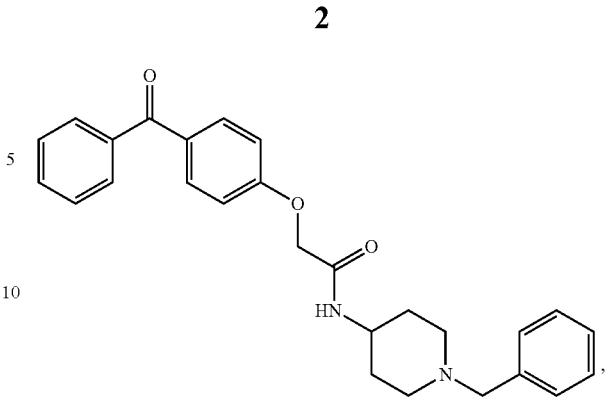

which is otherwise referred to as "adiporon." (See Okada-Iwabu et al., "A small-molecule AdipoR agonist for type 2 diabetes and short life in obesity," Nature 493 (503), Nov. 28, 2013, the content of which is incorporated herein by reference in its entirety).

Also disclosed are methods that include identifying a cancer patient that has one or more mutations in a gene of the Set1/COMPASS pathway and/or identifying a cancer patient that is overexpressing Set1/COMPASS, and subsequently administering to the patient a therapeutic amount of an agonist and/or an inhibitor of the Set1B/COMPASS pathway to the patient identified as having one or more mutations in Set1/COMPASS and/or identified as overexpression Set1/COMPASS. Mutations may be identified, for example, by obtaining a genomic DNA sample from the patient and sequencing the genomic DNA sample to identify one or more mutations in Set1/COMPASS. Overexpression may be identified by obtaining a biological sample from the patient and measuring Set1/COMPASS in the biological sample relative to a control sample (e.g., a sample from a normal patient).

Therapeutic agents administered in the disclosed methods may include agonists and/or inhibitors associated with components of the Set1B/COMPASS pathway. The therapeutic agents may include, but are not limited to, small molecule agonists/inhibitors, peptide agonists/inhibitors, and/or nucleic acid molecules. Agonists and inhibitors may include small molecule agonists and/or inhibitors (e.g., which be non-protein agonists and/or inhibitors such as adiporon or derivative thereof) and also may include proteinaceous agonists and/or inhibitors.

Specifically contemplated herein is the use of agonists of the adiponectin receptor 1 (adipoR1 agonists) to treat triple negative breast cancer. In addition to adipoR1 agonists, other agents that can inhibit the Set1B/BOD1 pathway may be administered for treating triple negative breast cancer.

**P<0.01; *P<0.05. Error bars represent sd. C) mRNA level of SET1B in the indicated cell lines are determined by real-time PCR. **P<0.01; *P<0.05. Error bars represent sd. D) LM2 cells were infected with lentivirus expressing shNONT and shSET1B. After puromycin selection, $4\times10^6$ cells were inoculated into the fat pad of nude mice. Tumor growth was measured two weeks after inoculation (n=7). Student's t test was used for statistical analysis. **P<0.001; *P<0.01. E) Representative tumors from each group of mice are shown. F) Tranwell assay was performed with LM2 cells transduced by shNONT and shSET1B. G) Quantification of migrated cell number as shown in F), **P<0.01; *P<0.05. Error bars represent sd.

Figure 2:
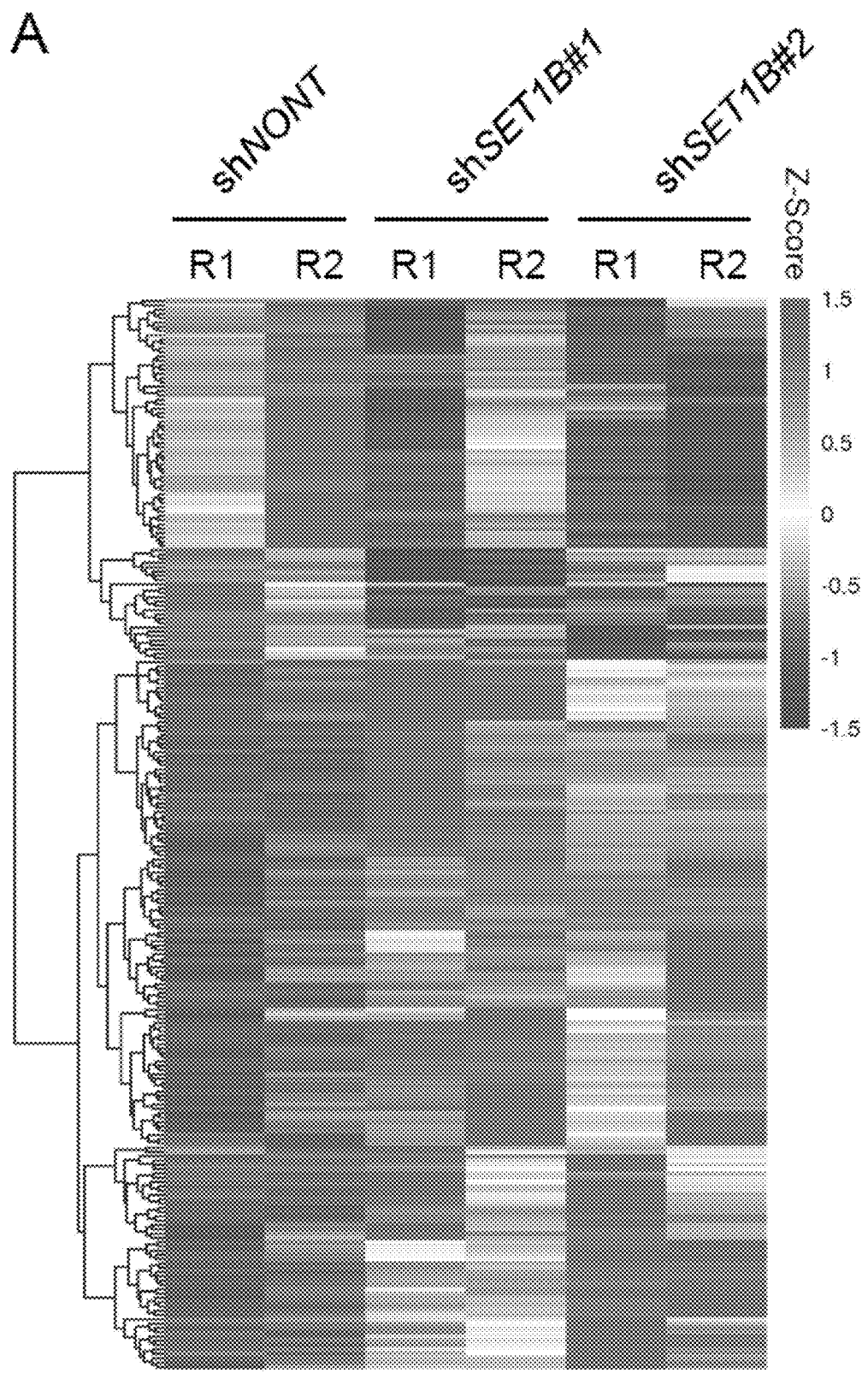
Figure 2:
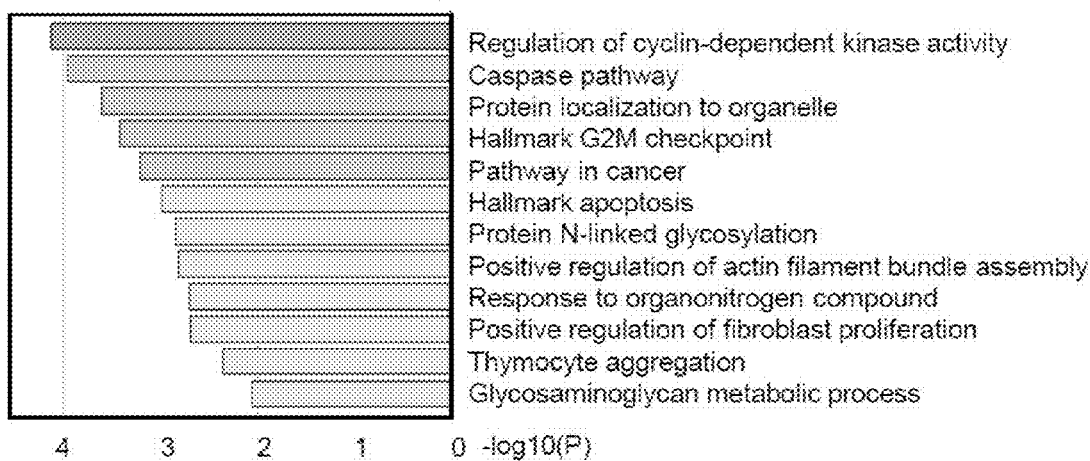
Figure 2:
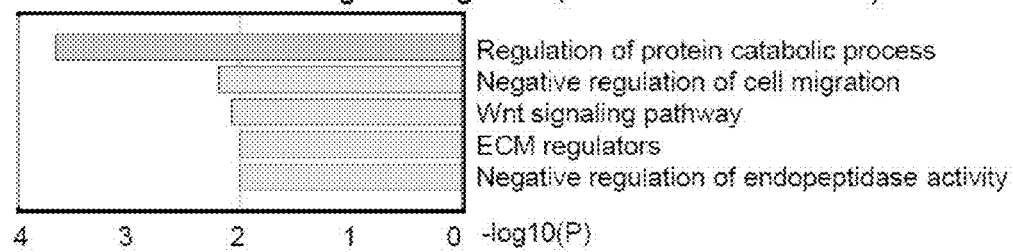
Figure 2:
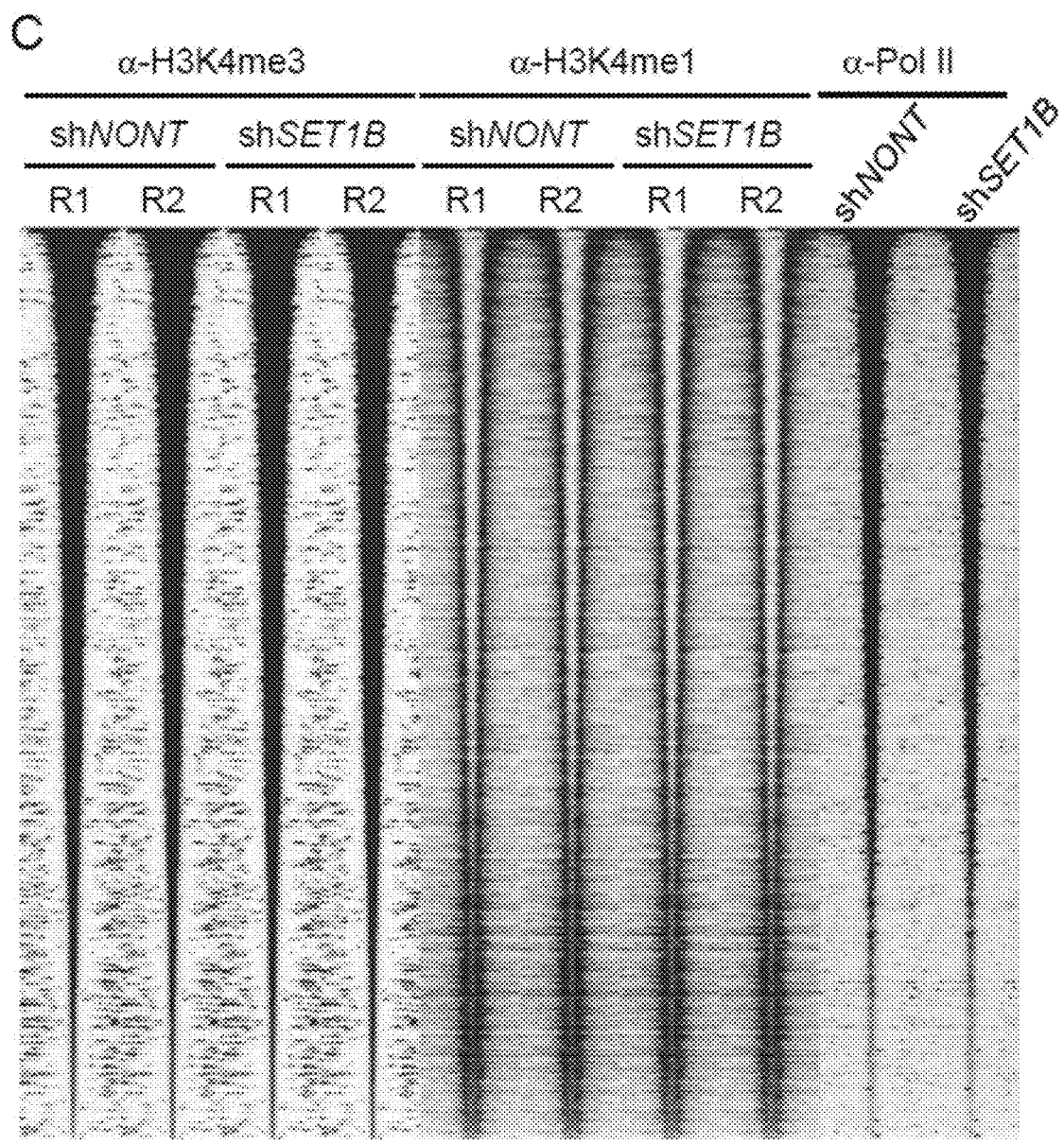
Figure 2:
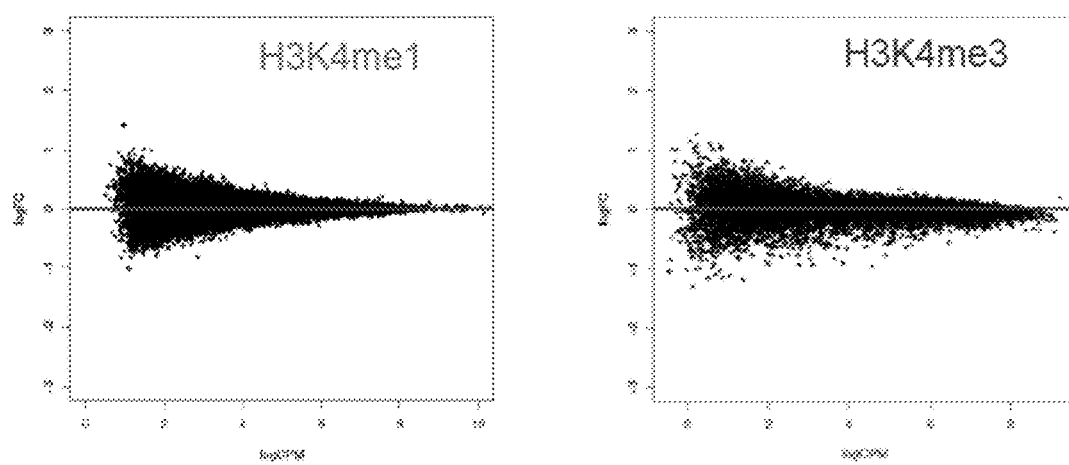
Figure 2:
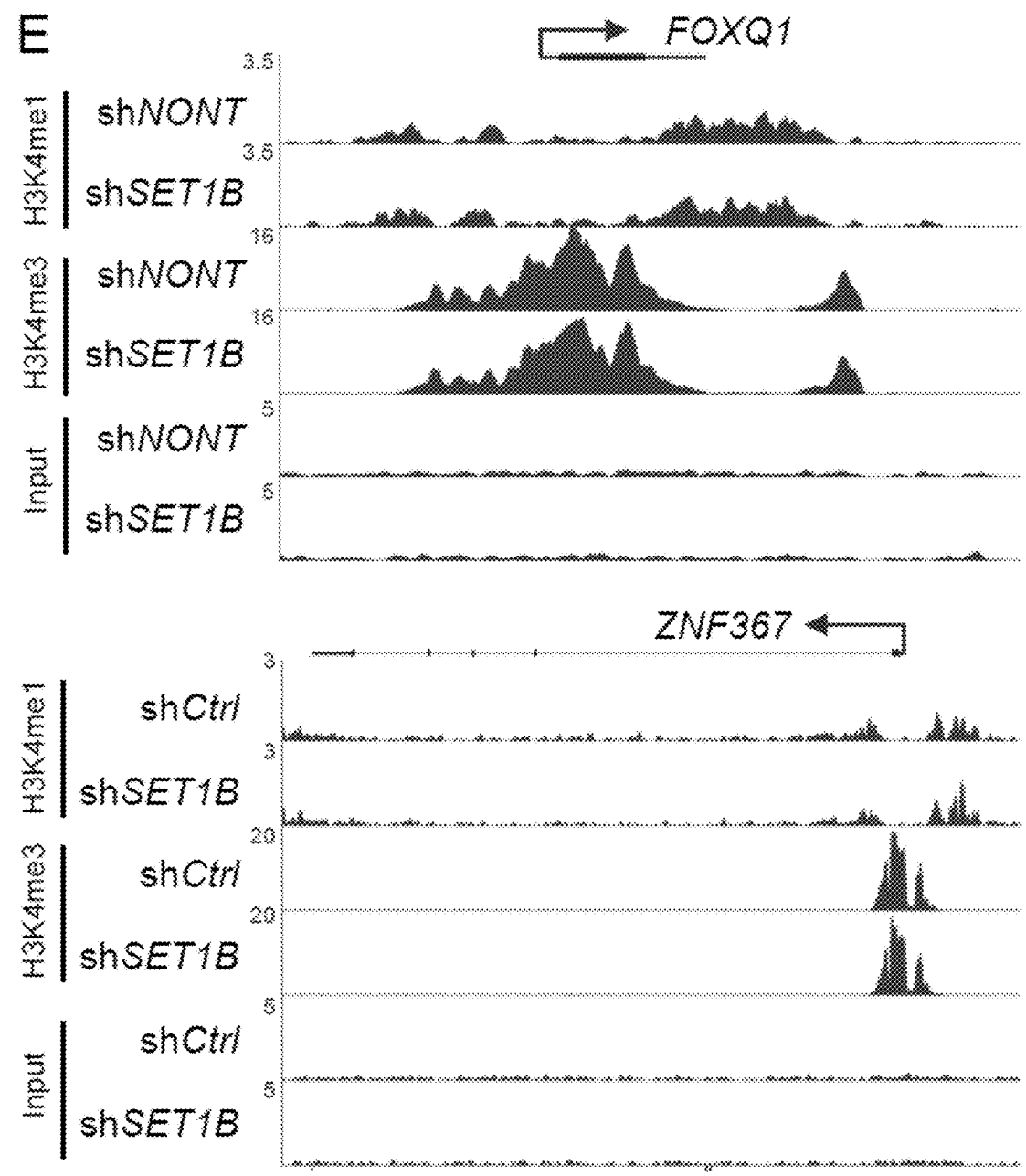

FIG. 2. SET1B/COMPASS regulates the expression of genes involved in tumorigenesis. A) MDA-MB-231 cells were infected with lentiviruses expressing shNONT, shSET1B#1, and shSET1B#2. Cells were selected with puromycin (2 ug/ml) 24 hours after virus infection. Total RNA was extracted from cells 72 hours after selection and subjected to RNA-seq. Heat map of genes significantly regulated by SET1B (adj.P<0.05) is shown, two replicates. B) Pathway enrichment analysis was performed with the Metascape platform available at its website. C) The occupancies of H3K4me3, H3K4me1, and RNA Polymerase II with and without shSET1B are plotted in +/−5 KB windows with respect to 17,959 H3K4me3 peak centers and sorted by decreasing H3K4me3 shNONT-R1 occupancy, two replicates. D) Differential occupancy analyses of H3K4me1 and H3K4me3 under H3K4me1 and H3K4me3 peaks, respectively, show no significant changes in occupancy between conditions in the MA plots. E) Genome browser track examples of H3K4me1 and H3K4me3 ChIP-seq in MDA-MB-231 cells transduced with shNONT, shSET1B#1, and shSET1B#2 for the indicated genes. The x-axis indicates the chromosome position, and the y-axis represents normalized read density in reads per million (rpm).

Figure 3:
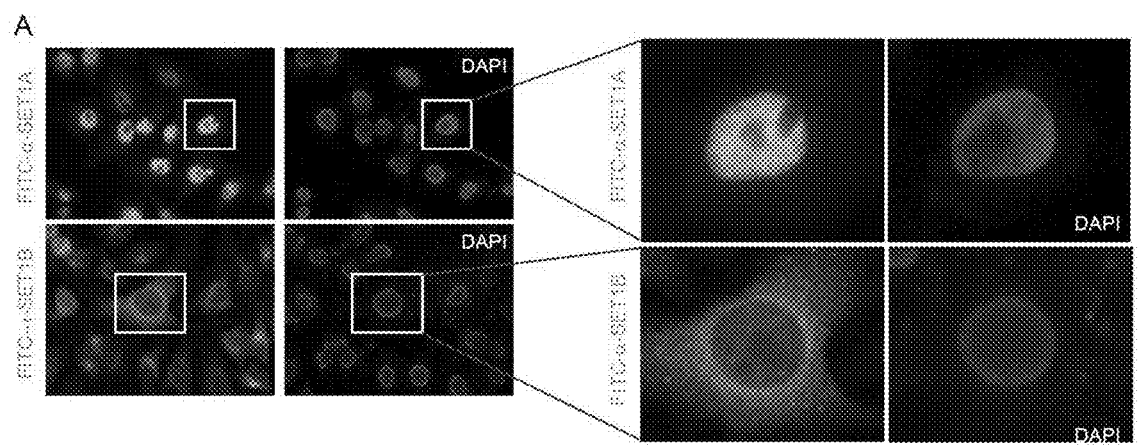
Figure 3:
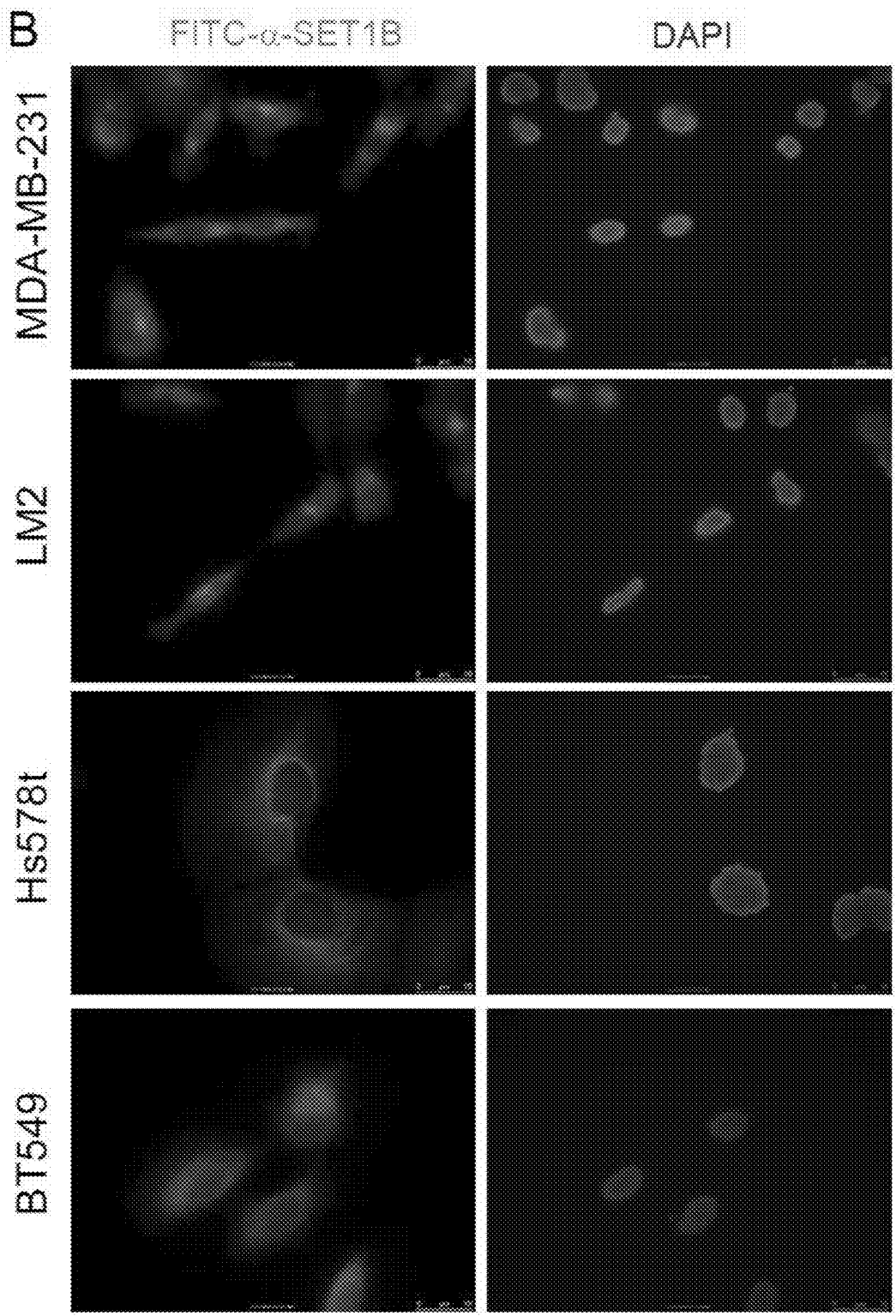
Figure 3:
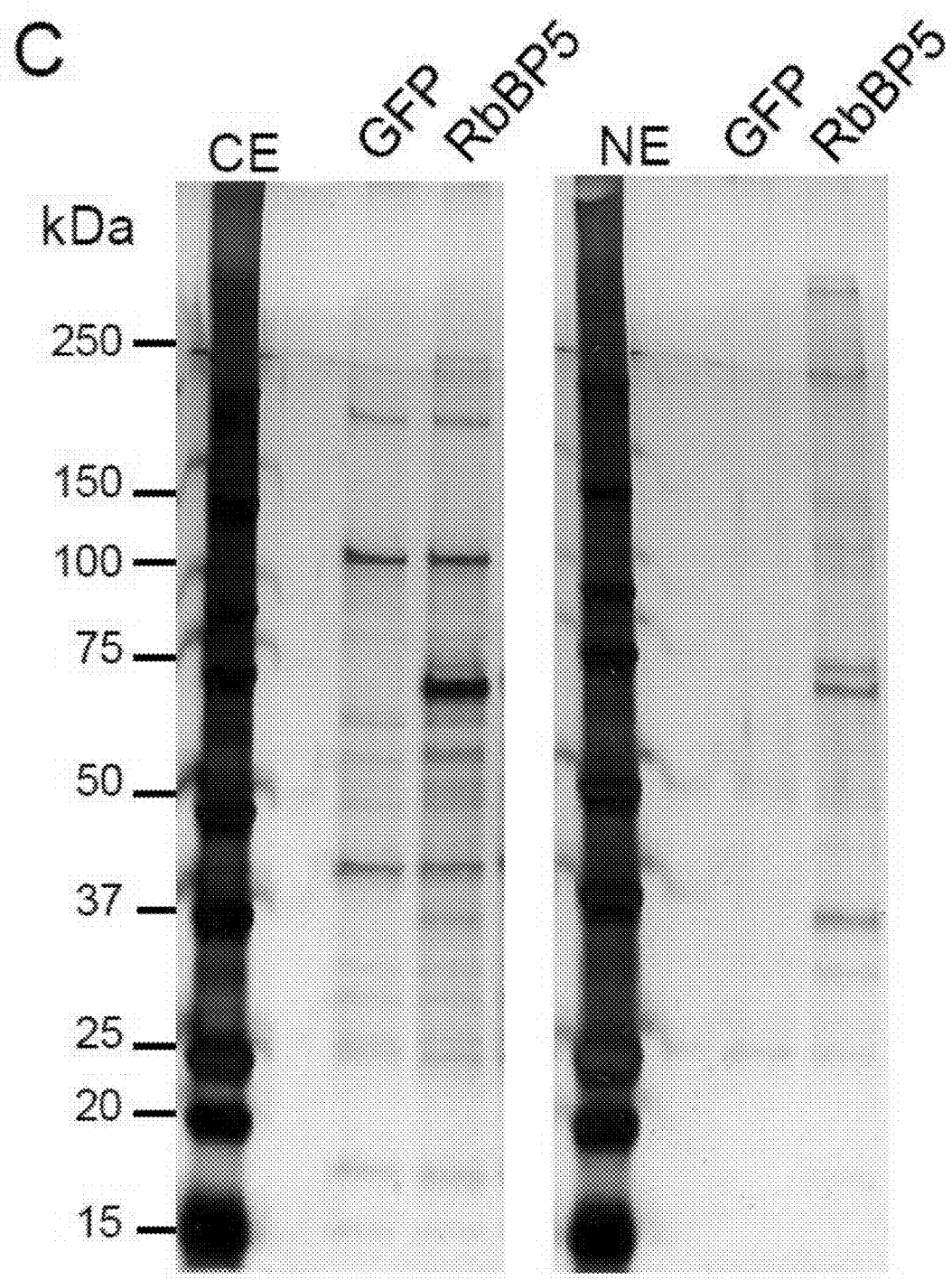
Figure 3:
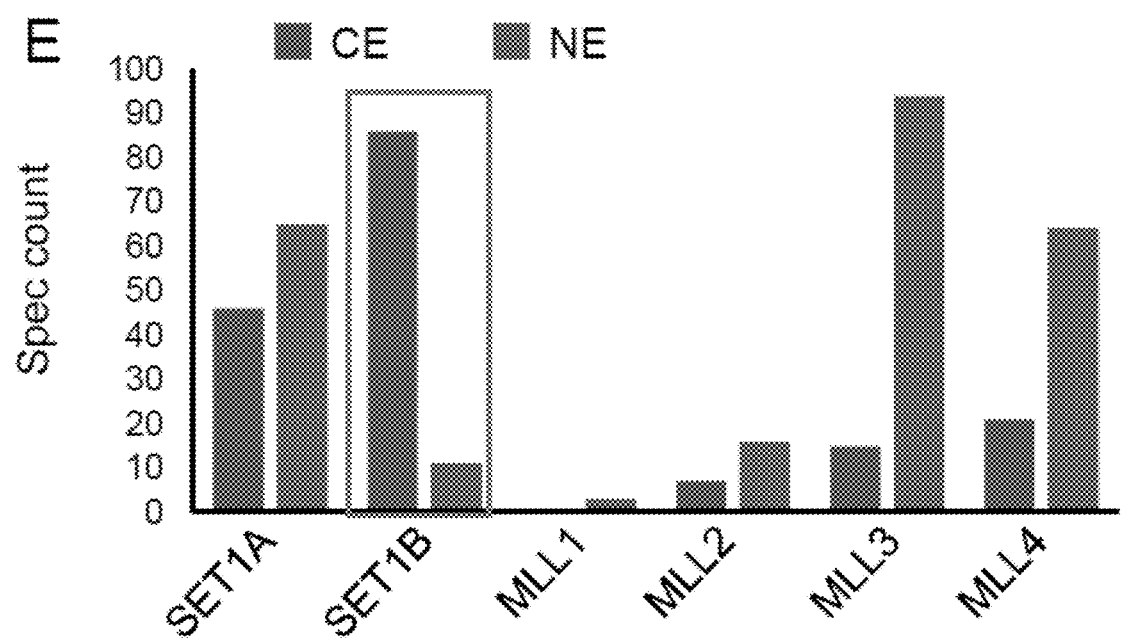
Figure 3:
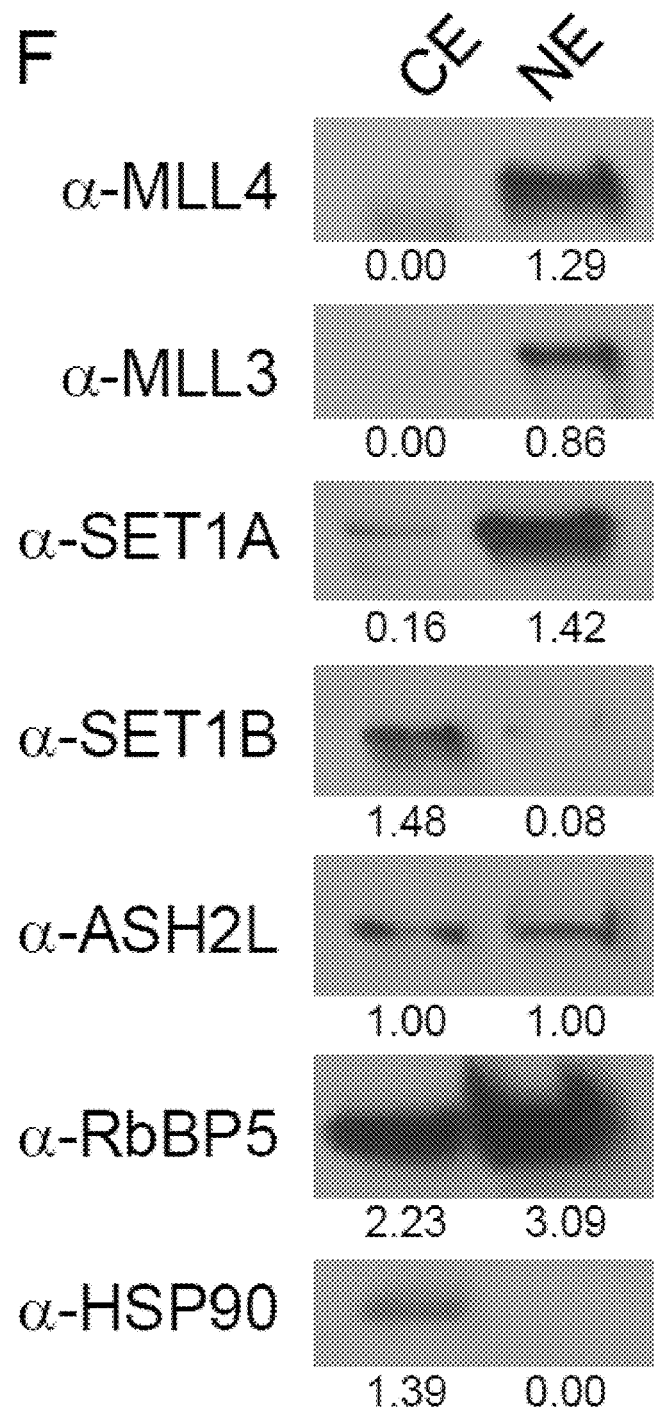
Figure 3:
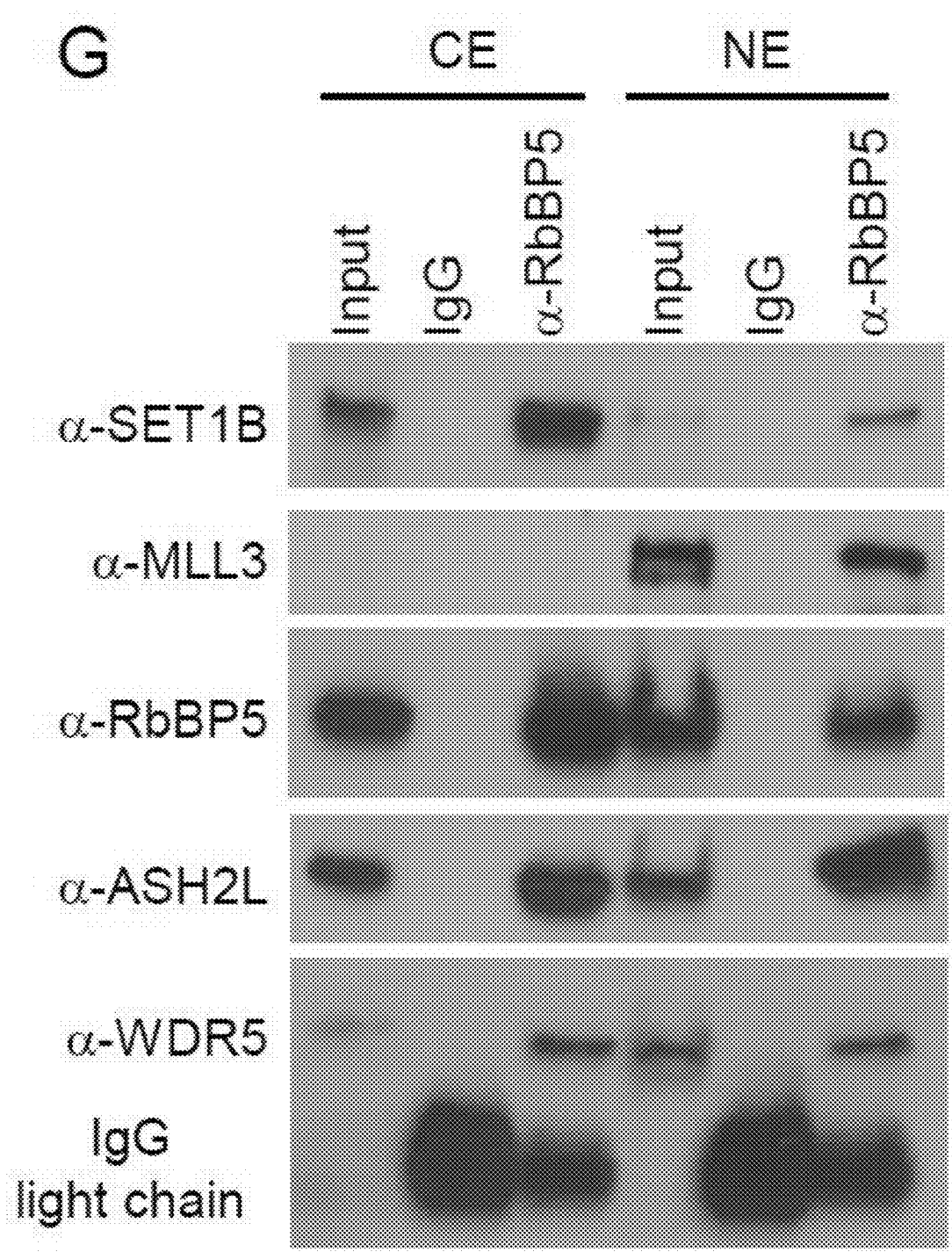

FIG. 3. SET1B is a major cytoplasmic COMPASS. A) Immunofluorescence was performed in HeLa cells with antibodies specific for SET1A or SET1B, left panel 10×, right panel 40×, n=4. B) Immunofluorescence was performed in MDA-MB-231, LM2, Hs578t, and BT549 cells, n=4. C) MCF7 cells were stably transfected with Flag-tagged RBBP5. COMPASS purified either from cytoplasmic or nuclear extracts was further subjected to mass spectrometric analysis. D, E) Number of spec count from the COMPASS family that purified with RBBP5 or GFP are shown. F) The cytoplasmic and nuclear proteins were extracted from MCF7 cells, the endogenous levels of SET1A, SET1B, MLL3, MLL4, ASH2L, and RBBP5 were detected by western blot analysis. HSP90 was used as the cytoplasmic fractionation marker, n=3, and the results are further quantified by ImageJ software. G) Immunoprecipitation was performed using anti-RBBP5 antibody from either cytoplasmic or nuclear extracts. SET1B, MLL3, ASH2L, RBBP5, and WDR5 protein levels were detected in the immunoprecipitates by Western blot analysis. CE, cytoplasmic extract; NE, nuclear extract, n=2.

Figure 4:
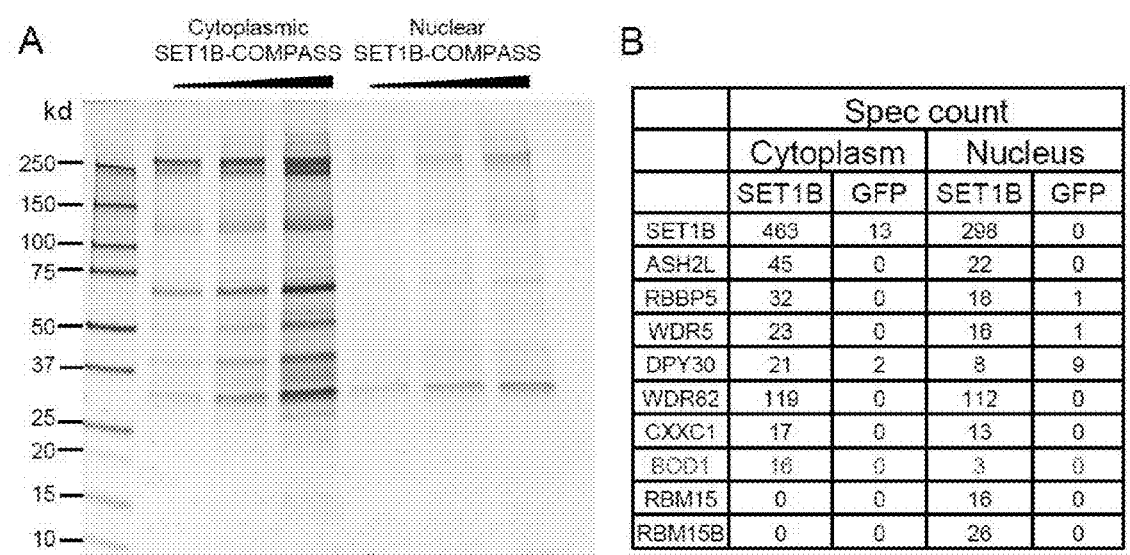
Figure 4:
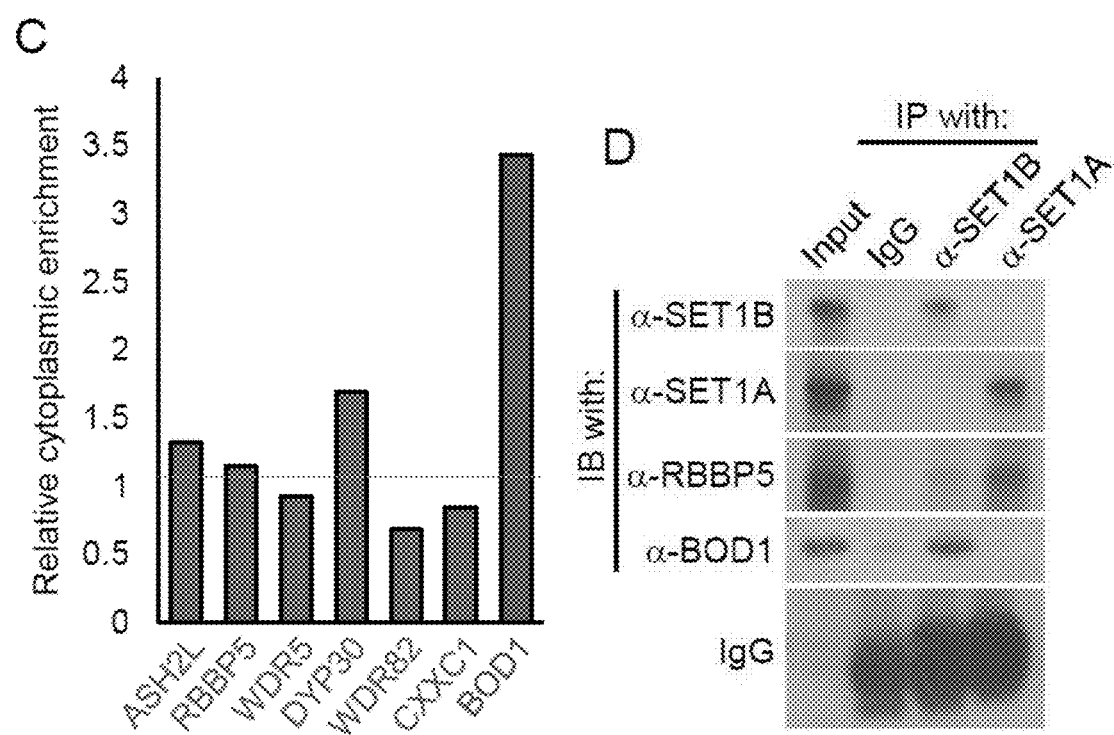
Figure 4:
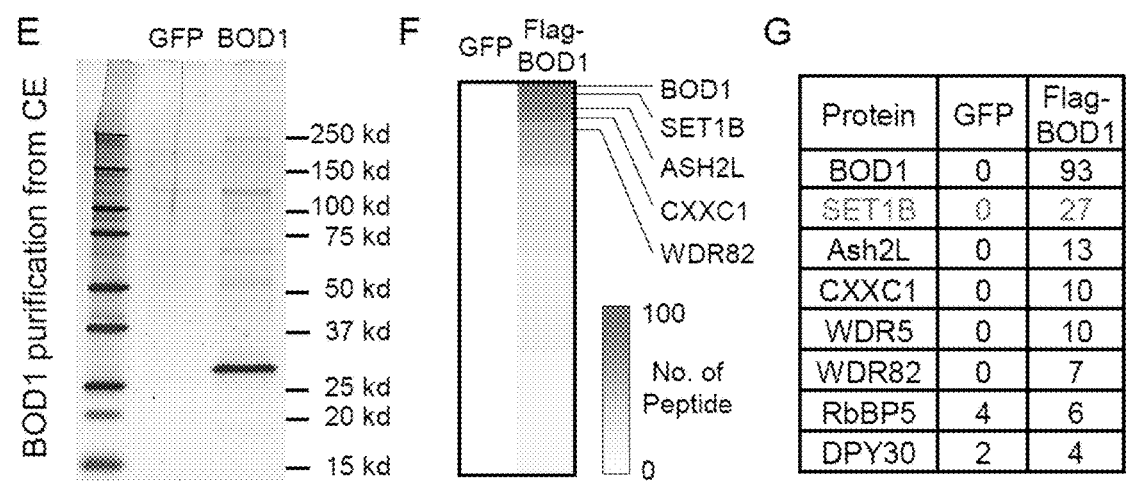
Figure 4:
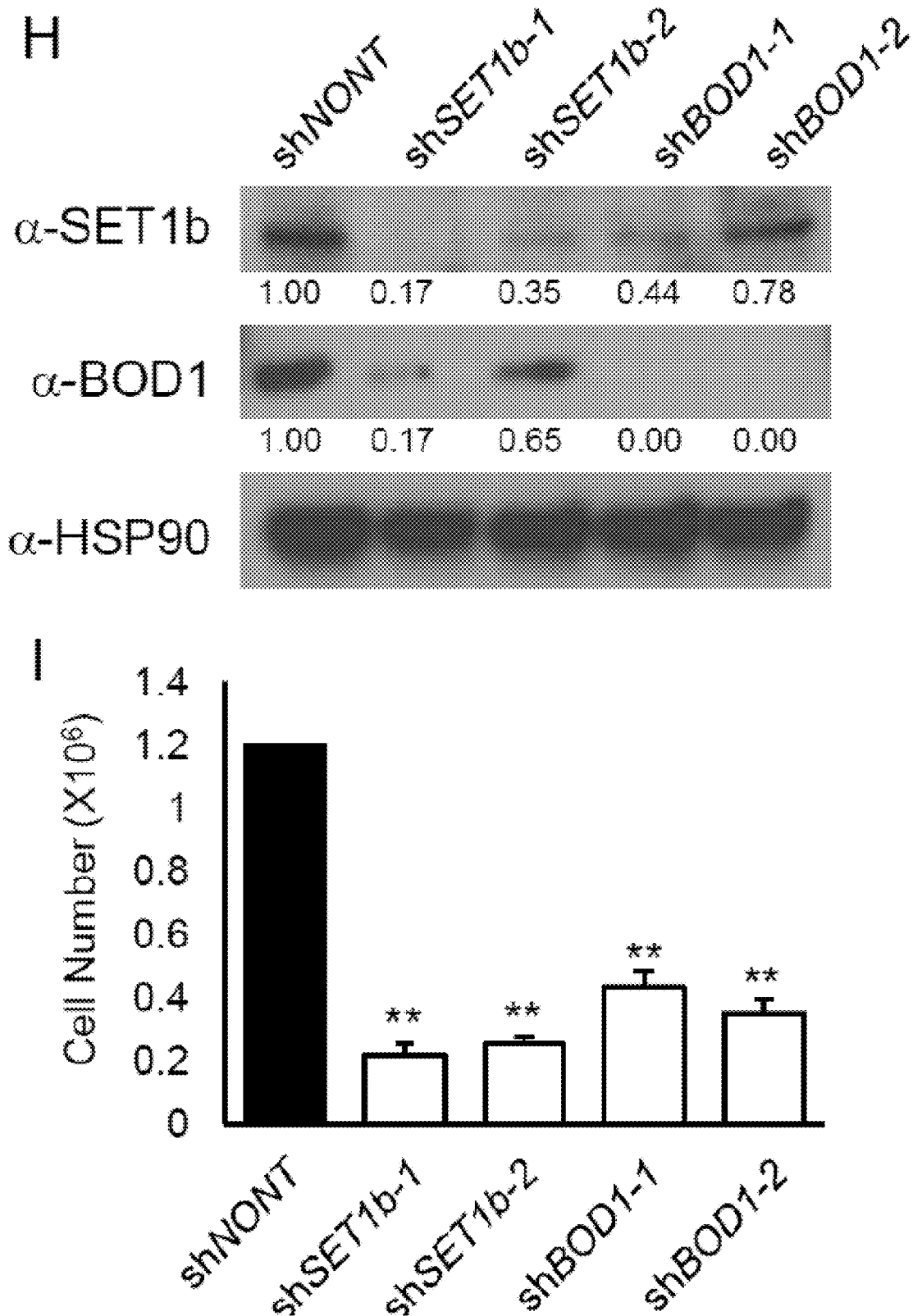
Figure 4:
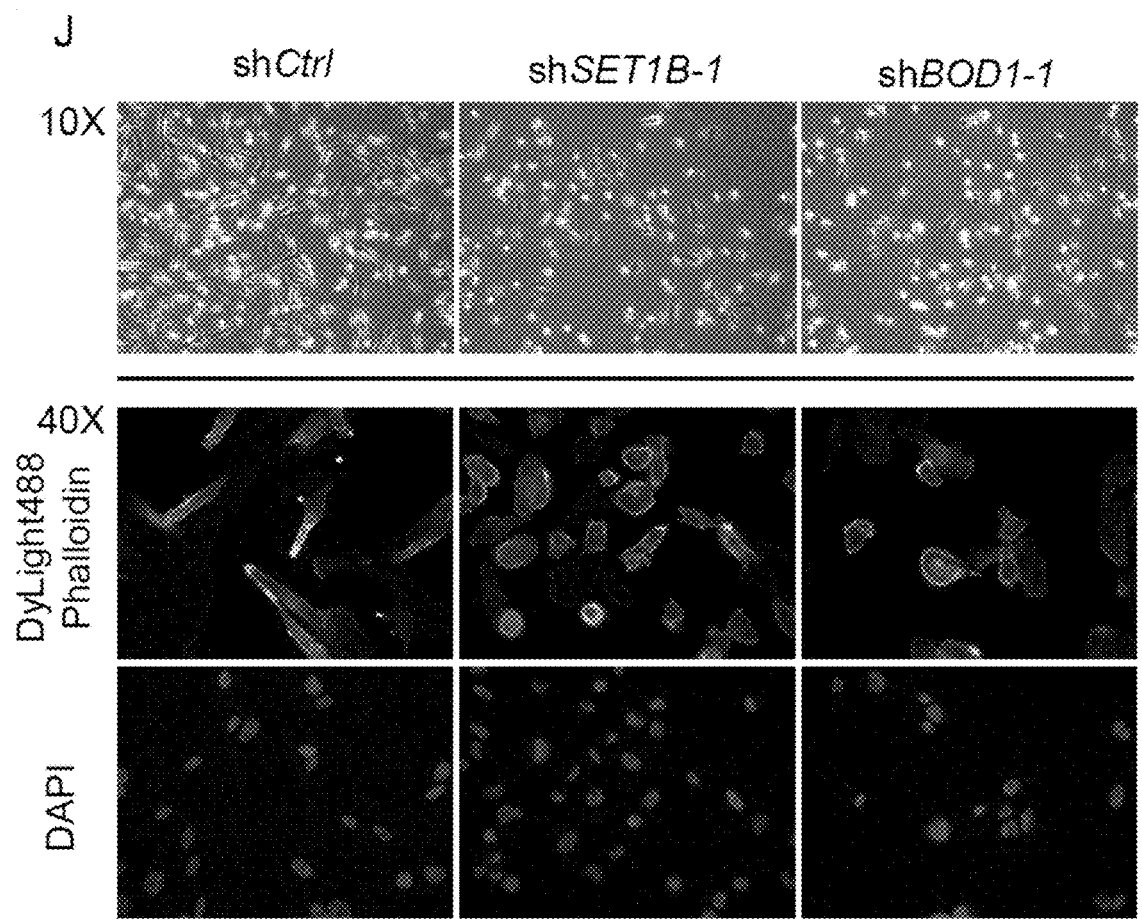

FIG. 4. BOD1 is a cytoplasm-specific subunit of SET1B COMPASS. A) MDA-MB-231 cells were stably infected with retroviruses expressing Flag-SET1B. Silver staining shows the flag-tagged SET1B protein purified with M2-beads from either cytoplasmic extracts or nuclear extracts (equal volume of eluted protein). B) The mass spectrometry analysis with equal amount of the interacting proteins of SET1B isolated from cytoplasmic and nuclear extracts are shown (equal amount). C) The result from panel B was further normalized with spec count of SET1B protein, and the relative cytoplasmic enrichment of protein was shown. The cytoplasmic enrichment was presented as Ratio between Cytoplasmic subunit/Cytoplasmic SET1B and Nuclear subunit/Nuclear SET1B. D) The endogens SET1A and SET1B protein was immunoprecipitated and the BOD1 protein in the immunoprecipitates was detected by western blot. The common subunit of SET1A and SET1B COMPASS, RBBP5 was used as control, n=2. E) Flag-BOD1 was purified from cytoplasmic extracts of MDA-MB-231-Flag-BOD1 cells and analyzed by silver staining. Mass spectrometry identified interacted proteins with Flag-BOD1. F) The heat map shows the top 100 protein co-purified with BOD1 but not GFP (0 peptide from GFP purification). G) Spec count of subunits from SET1B COMPASS are shown. Cells stably expressing GFP were used as the negative control. H) SET1B and BOD1 were knocked down with two distinct shRNAs in MDA-MB-231 cells, and the protein levels of SET1B and BOD1 were detected by Western blotting. HSP90 was used as the internal control, n=3. The results are further quantified by ImageJ software. H) The growth rate of SET1B or BOD1 knocked down cells was determined by cell counting. n=4, Student's t test was used for statistical analysis. **P<0.01; *P<0.05. Error bars represent sd. I) The representative cell morphology of SET1B or BOD1 knockdown cells are shown (upper panel). The cytoskeleton of cells transfected with shNONT, shSET1B, or shBOD1 was detected by phalloidin staining, n=4.

Figure 5:
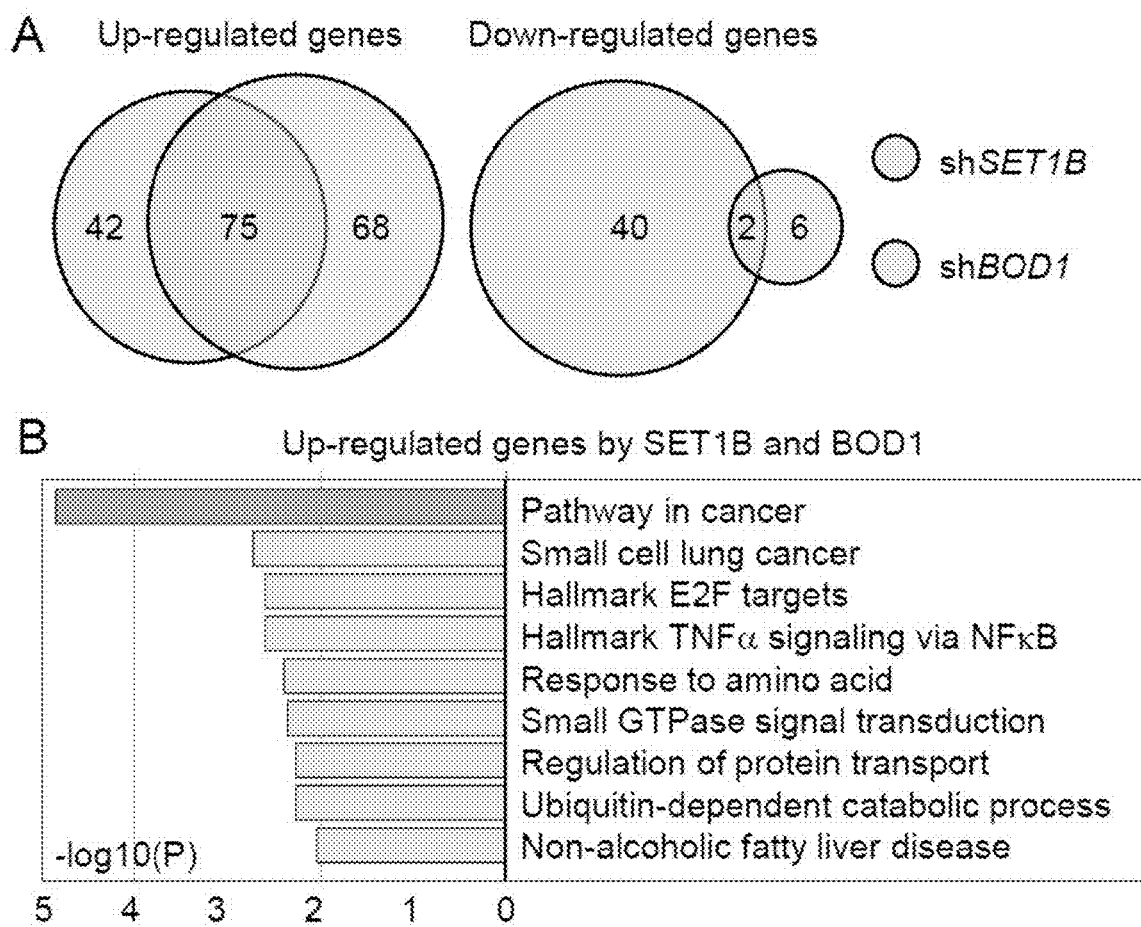
Figure 5:
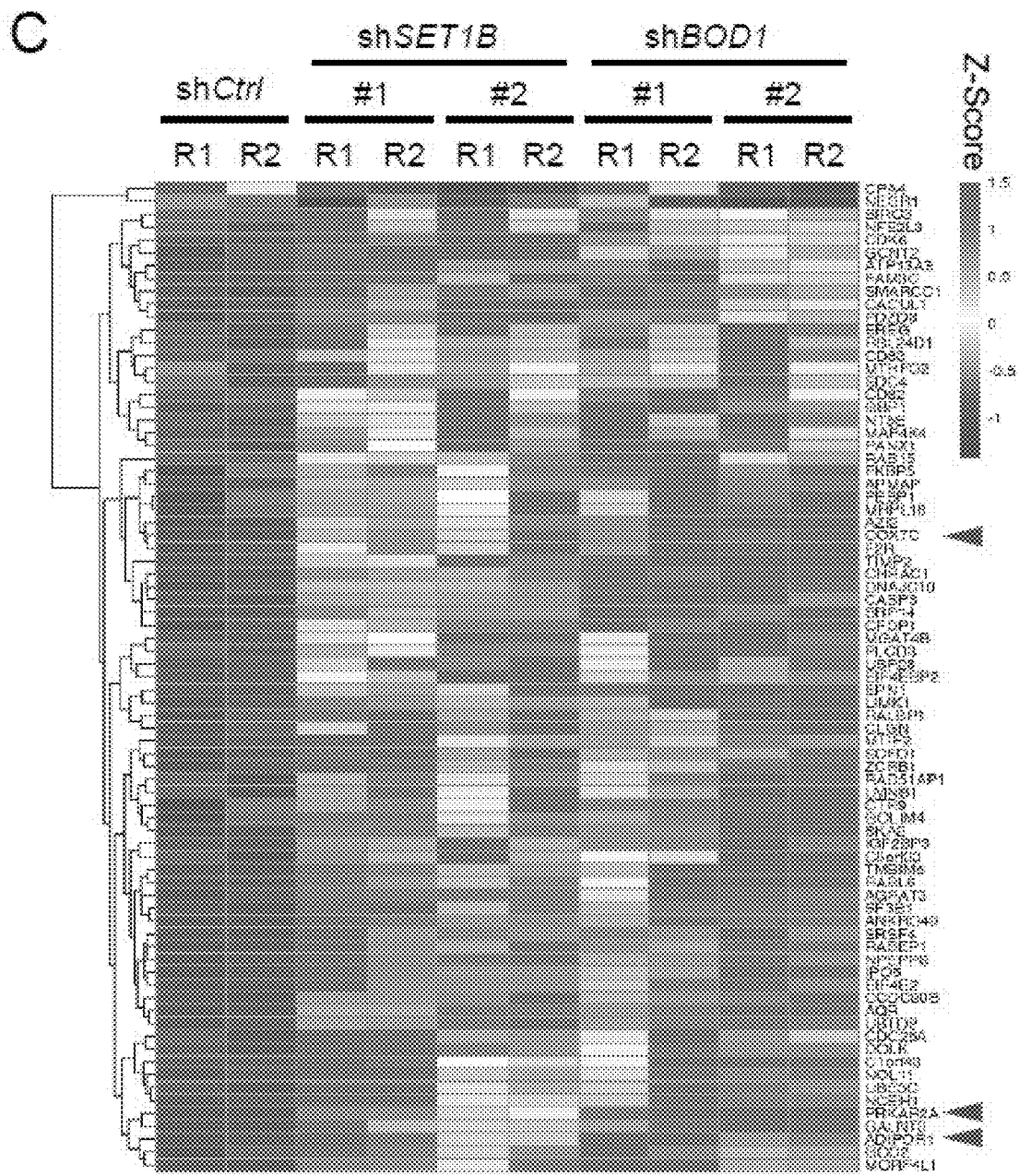
Figure 5:
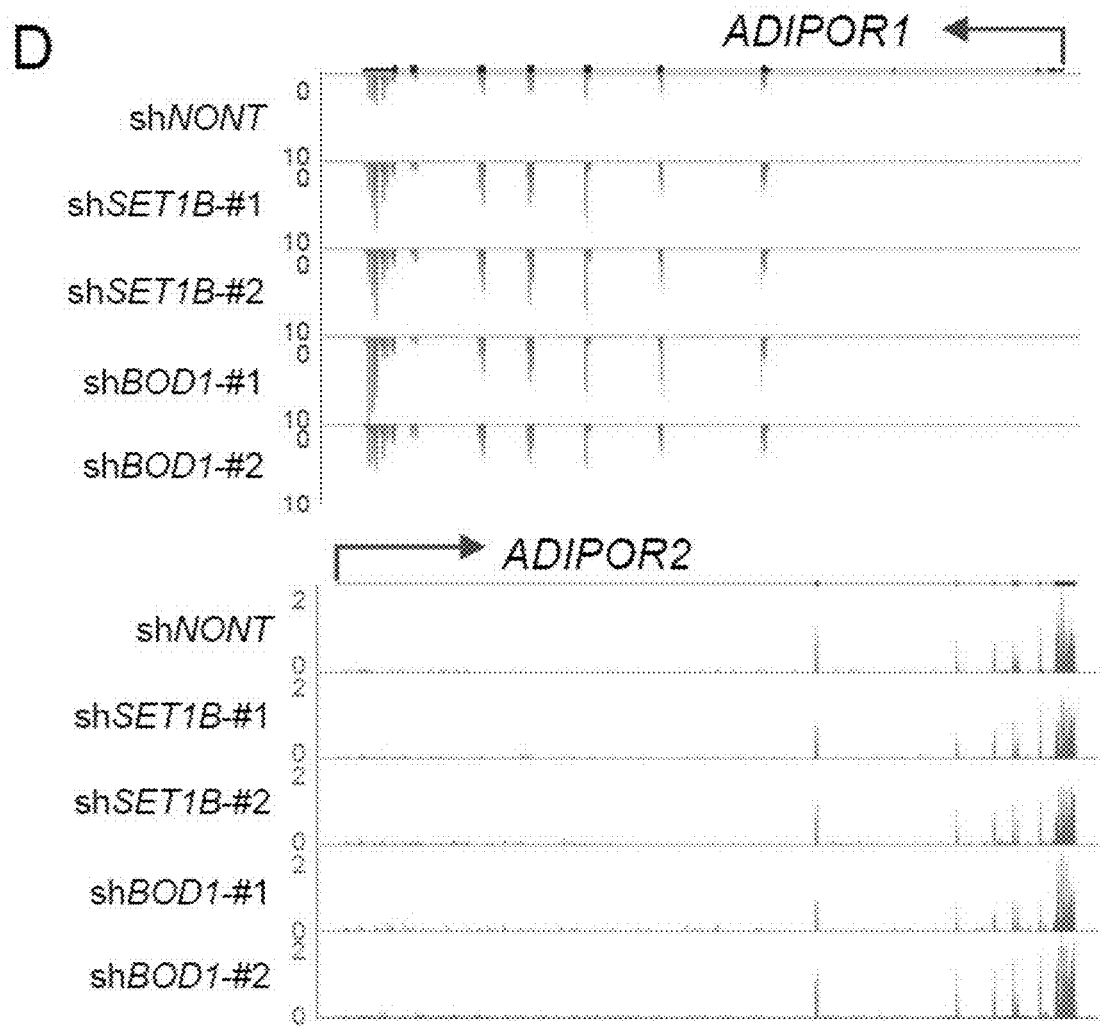
Figure 5:
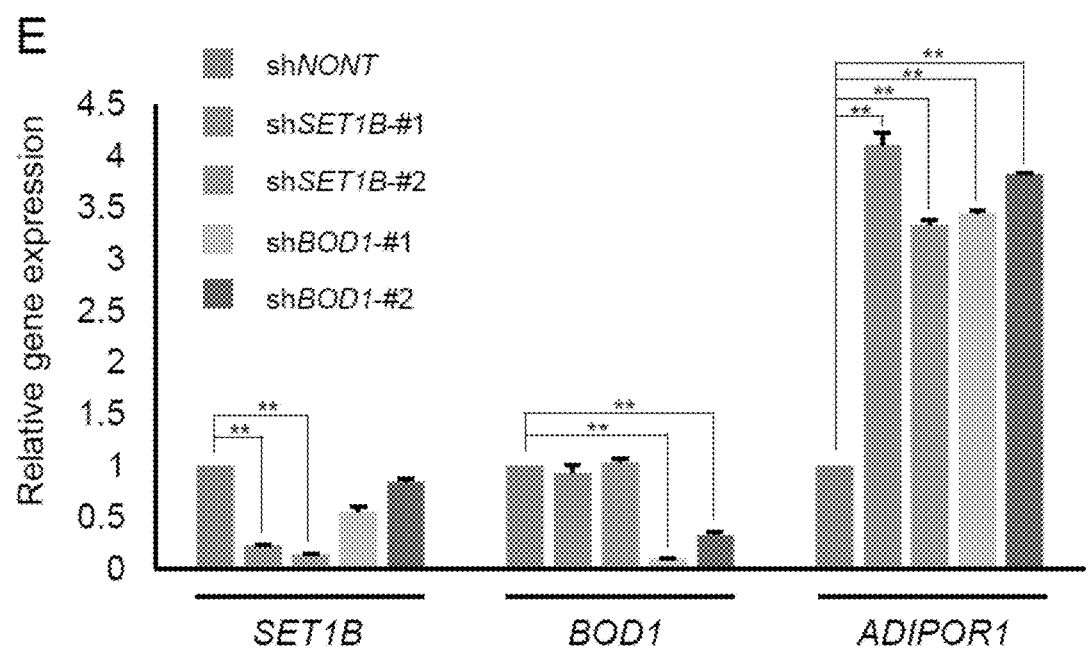
Figure 5:
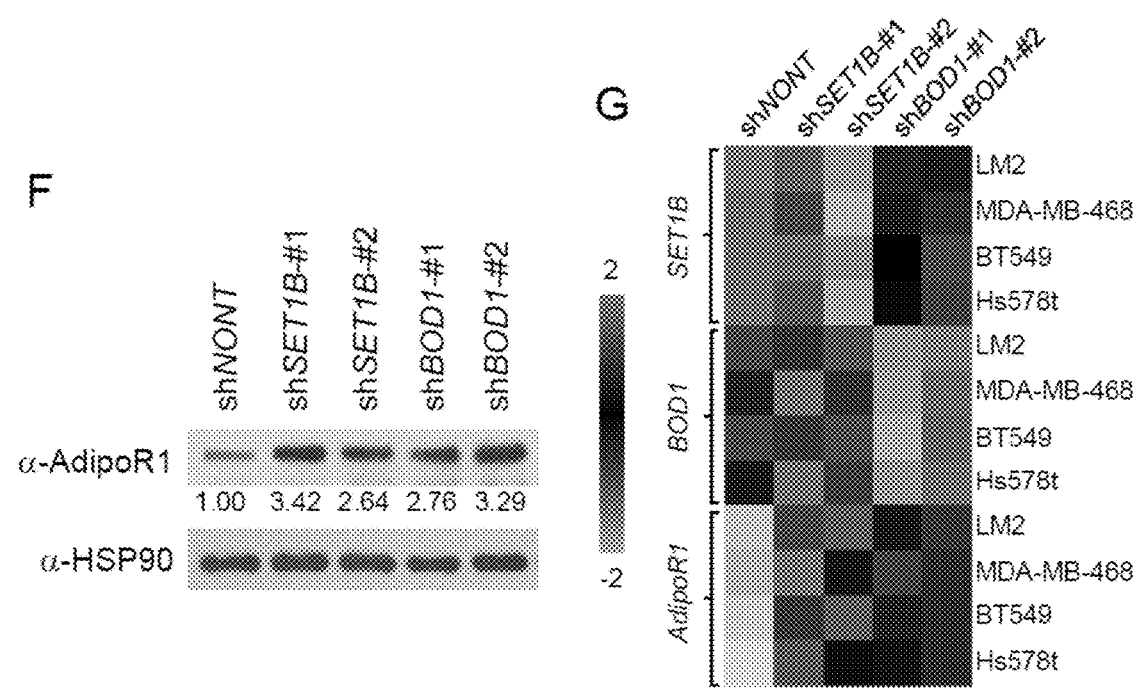
Figure 5:
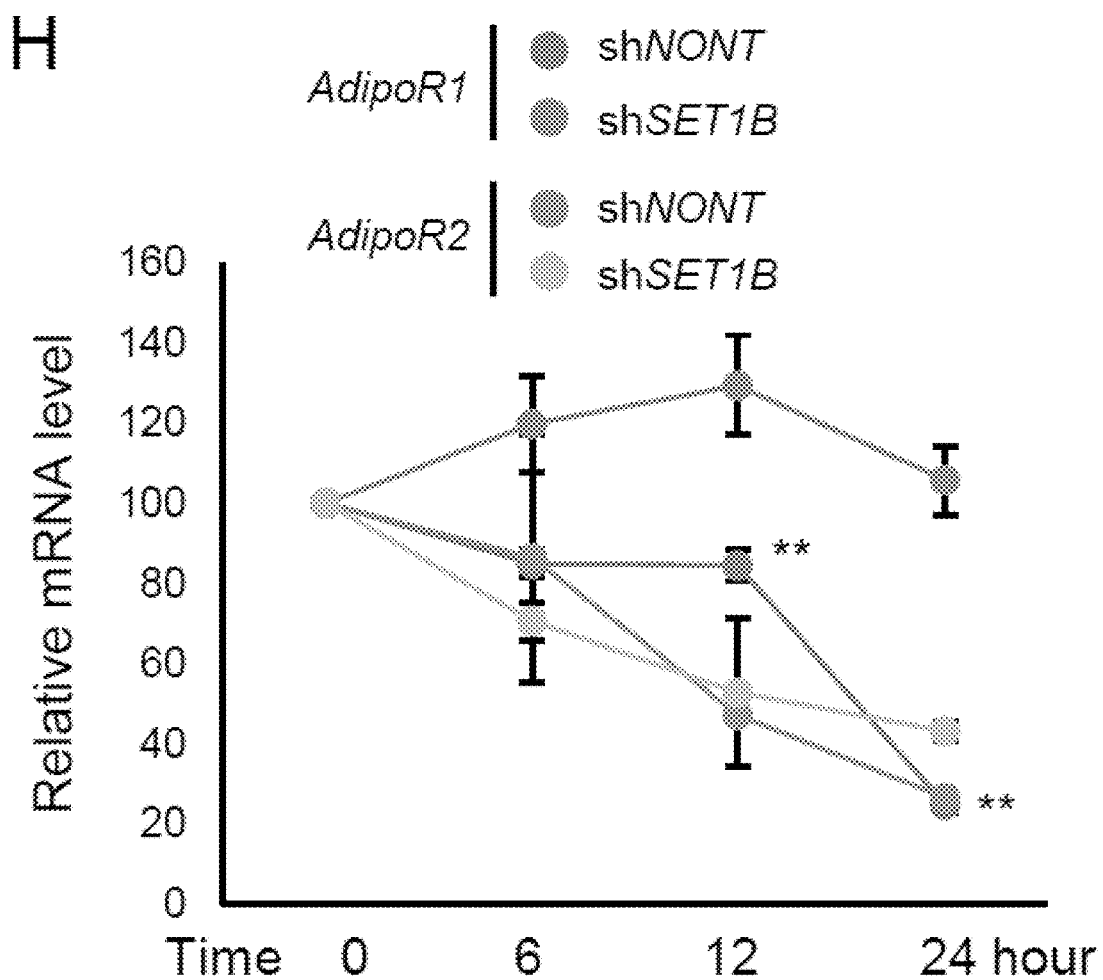

FIG. 5. Loss of SET1B/BOD1 COMPASS activates AdipoR1 signaling. A) MDA-MB-231 cells were infected with lentivirus expressing shNONT, shSET1B#1 and #2, and shBOD1#1 and #2. Cells were selected with puromycin (2 ug/ml) 48 hours after virus infection. Total RNA was extracted from the cells subjected to RNA-seq, two replicates. The Venn diagram shows the common genes regulated by both SET1B and BOD1. B) Significant enriched pathways regulated by both SET1B and BOD1 are shown. C) Heatmap analysis shows the genes significantly regulated by SET1B and BOD1. Genes involved in ADIPOR1 signaling are shown. D) Representative RNA-seq tracks of ADIPOR1 and ADIPOR2 in MDA-MB-231 cells infected with shNONT, shSET1B, and shBOD1 virus are shown. The mRNA and protein level of AdipoR1 in cells infected with shNONT, shSET1B, and shBOD1 virus are confirmed by real-time PCR (E) and western blot (F). n=3, Student's t test was used for statistical analysis. **P<0.01; *P<0.05. Error bars represent sd. The results from western blot was further quantified by ImageJ software. G) SET1B and BOD1 were knocked down in LM2, MDA-MB-468, BT549, and Hs578t cells with two distinct shRNAs. Heatmap analysis of the relative mRNA levels of SET1B, BOD1, and ADIPOR1 in the different knockdown conditions are shown, n=3. H) MDA-MB-231 cells were infected with shNONT, shSET1B, and shBOD1 virus for 12 hours and further selected with puromycin for additional 24 hours. After that, the cells were treated with DMSO, or Actinomycin D (20 ug/ml) for different time, respectively. The mRNA level of AdipoR1 and AdipoR2 was determined by real-time PCR, n=3, Student's t test was used for statistical analysis. **P<0.01; *P<0.05. Error bars represent sd.

Figure 6:
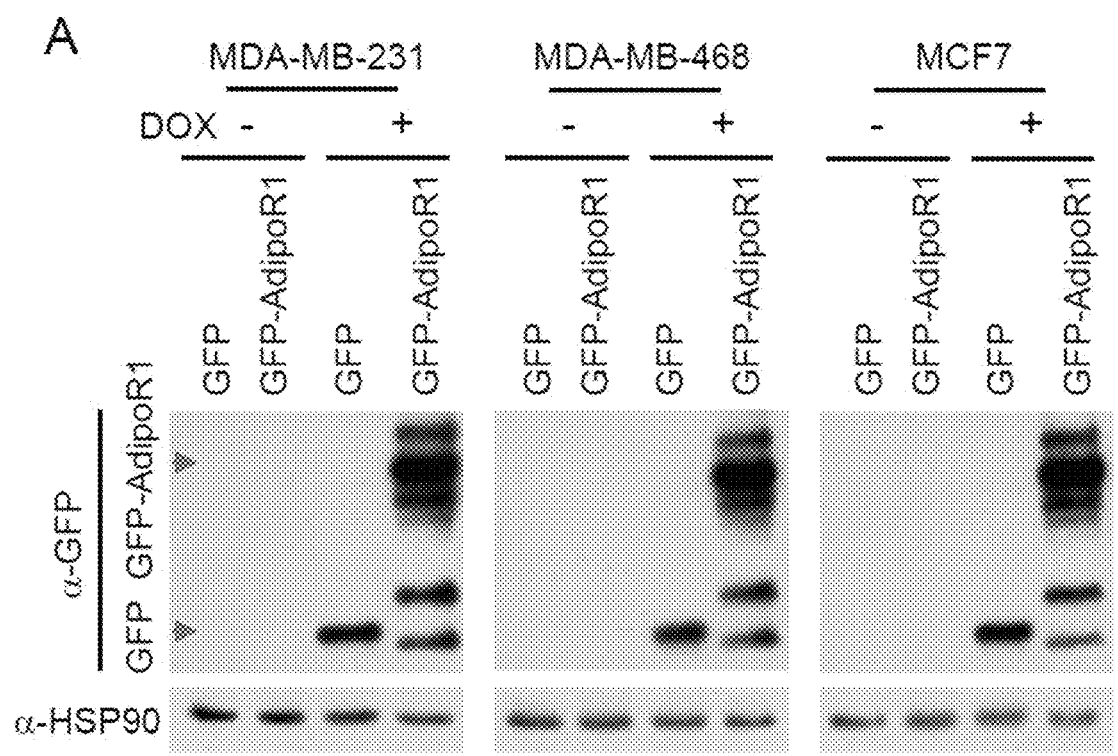
Figure 6:
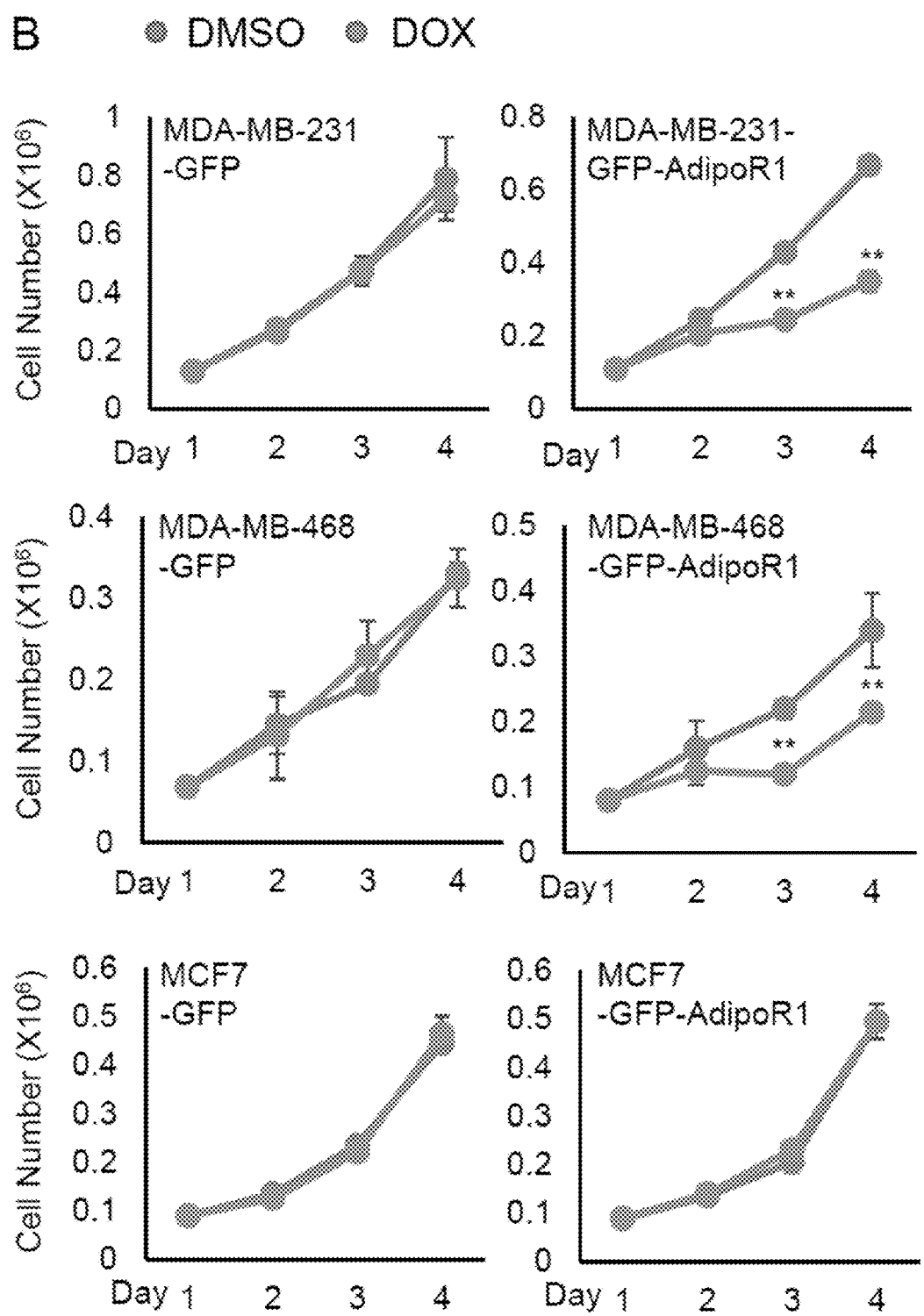
Figure 6:
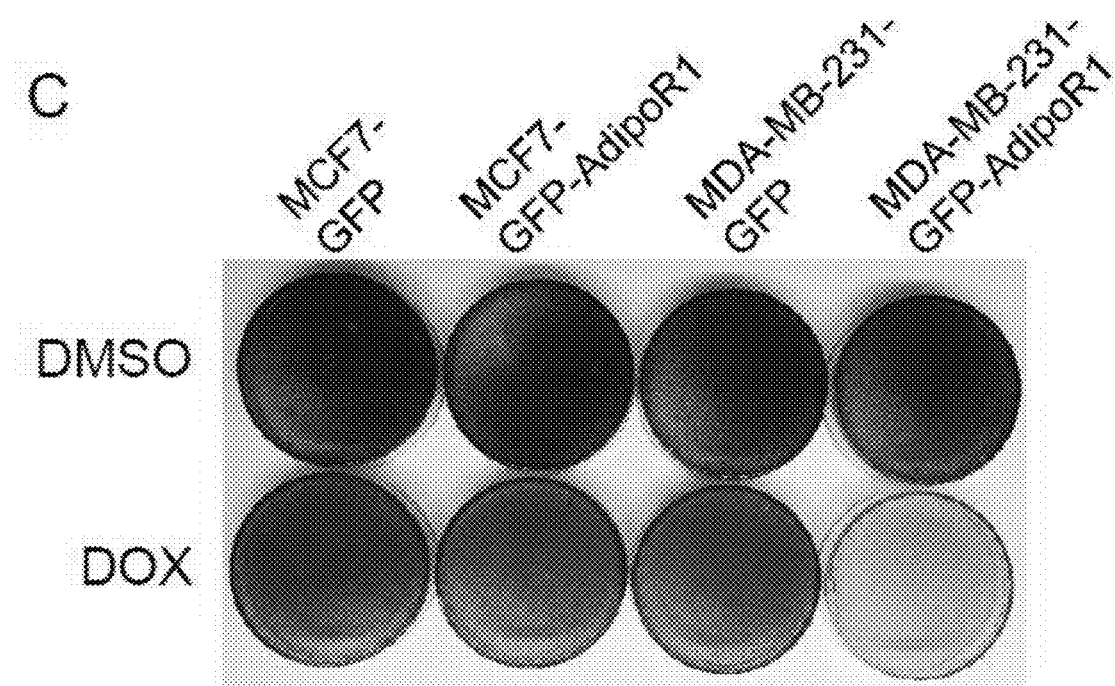
Figure 6:
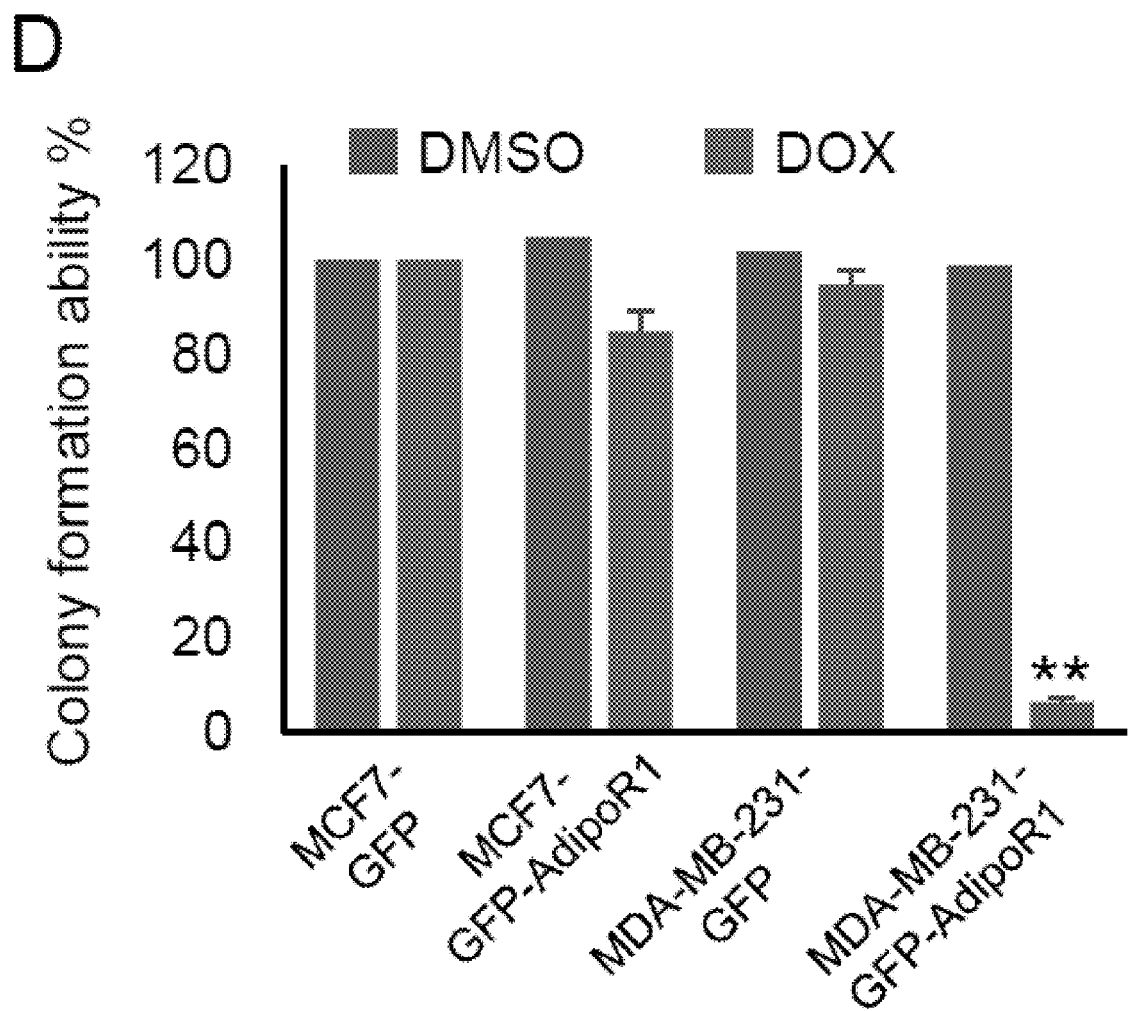
Figure 6:
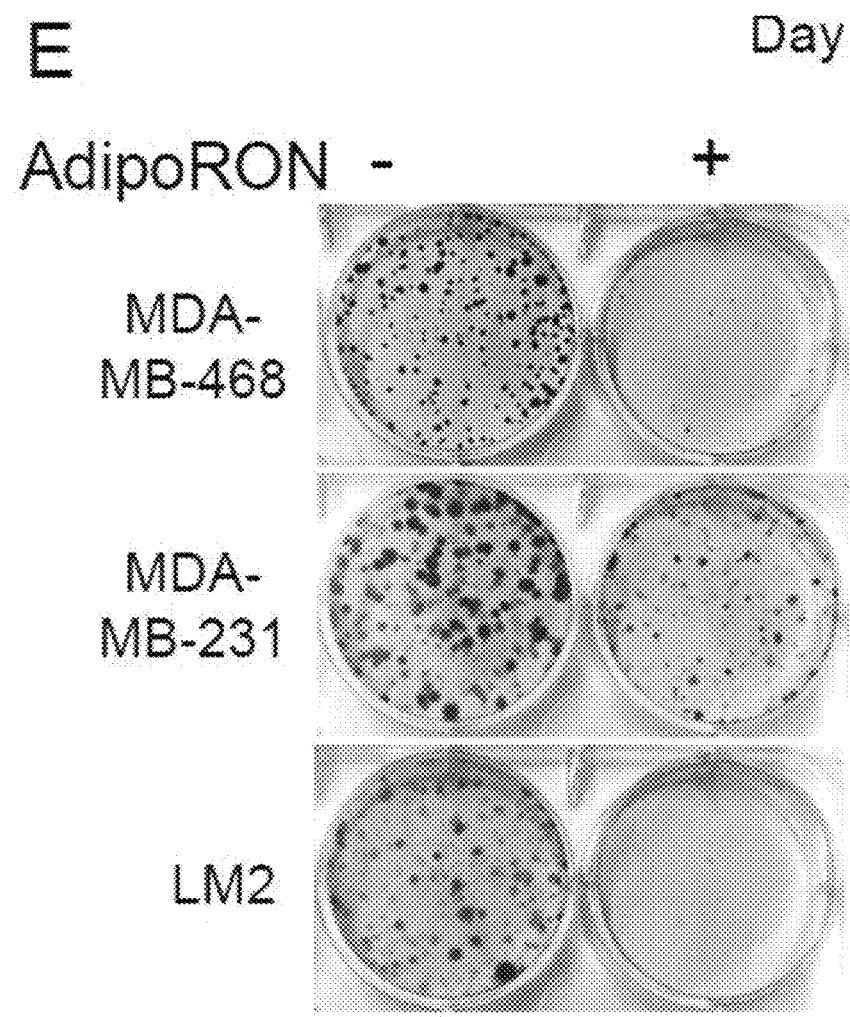
Figure 6:
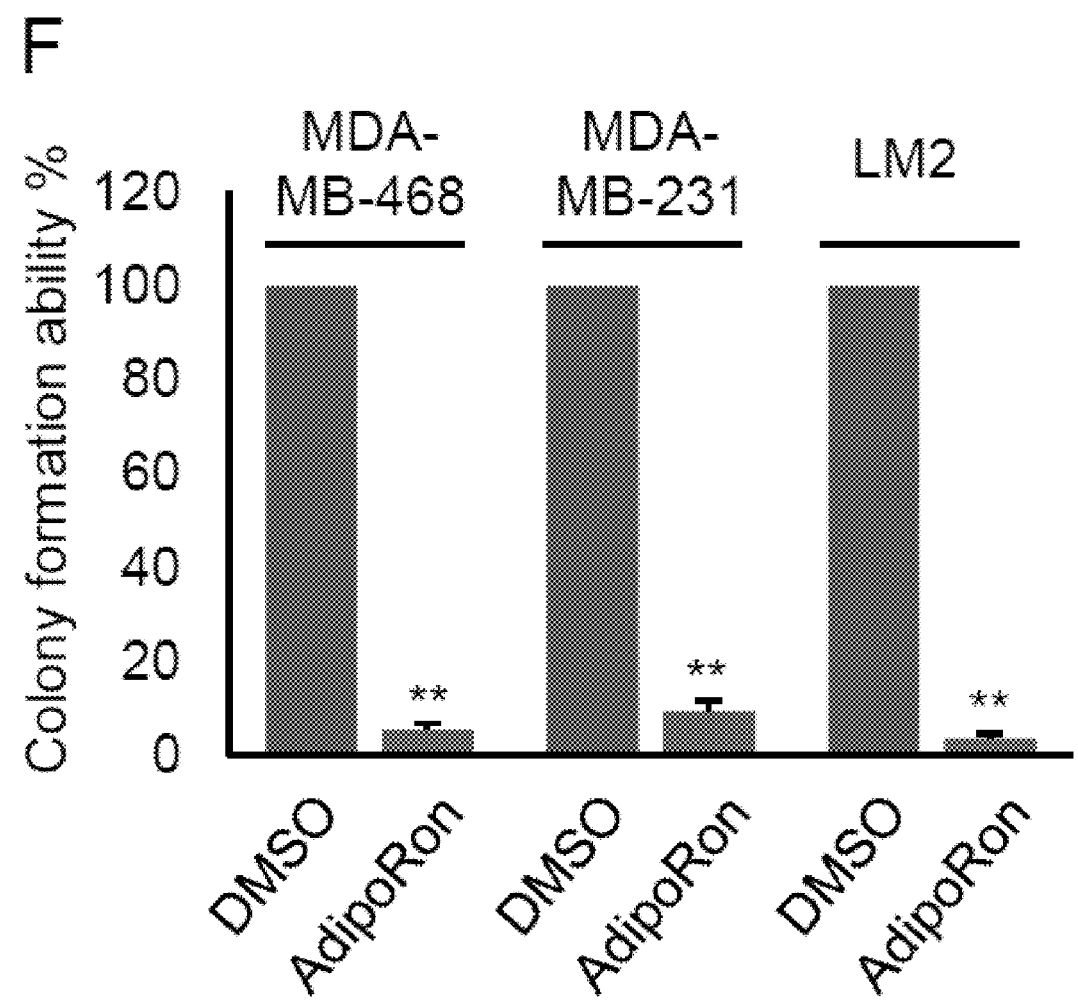
Figure 6:
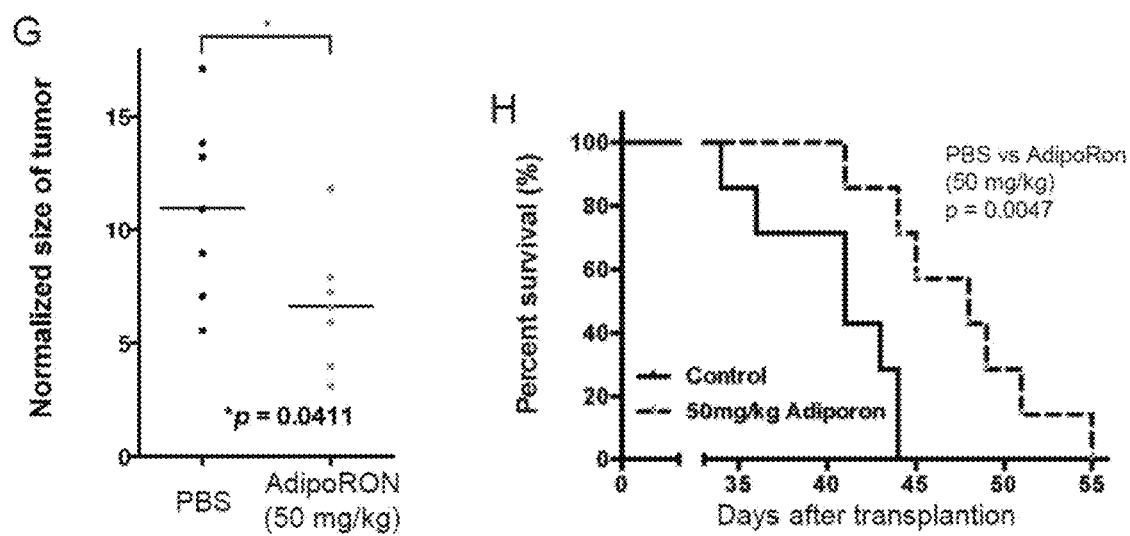

FIG. 6. Targeting AdipoR1 signaling in human TNBC. A) MDA-MB-231, MDA-MB-468 and MCF7 cells were infected with lentiviruses inducibly expressing either GFP or GFP-ADIPOR1. After neomycin selection, the stably transfected cells were treated with DMSO or doxycycline (DOX). The induced GFP or GFP-AdipoR1 was determined by western blot in three cell lines, n=3. B) The proliferation ability of GFP or GFP-ADIPOR1 inducible cell lines were determined by cell counting, n=3, Student's t test was used for statistical analysis. **P<0.01; *P<0.05. Error bars represent sd. C) The GFP or GFP-ADIPOR1 inducible cell lines were seeded in 6-well plates at the concentration of $4\times10^4$ living cells per well. The cells were then treated with DMSO or doxycycline. The cell survival was shown six days after doxycycline treatment by crystal violet staining. D) Quantification of crystal violet staining was determined as described in materials section. n=4, Student's t test was used for statistical analysis. **P<0.01; *P<0.05. Error bars represent sd. E) MDA-MB-231, MDA-MB-468, and LM2 cells were seeded in 6-well plates at the concentration of 200 cells per well. The cells were treated with either DMSO or AdipoRON (10 µM) for three weeks, and the colonies were stained with crystal violet. F) Quantification of crystal violet staining was determined as described in materials section. n=4, Student's t test was used for statistical analysis. **P<0.01; *P<0.05. Error bars represent sd. G, H) $4\times10^6$ of LM2 cells were inoculated into the fat pad of nude mice. 12 days after injection, when the tumor reached to 100 mm$^3$, mice were randomly divided into two groups. They were treated with either PBS or AdipoRon (50 mg/kg) for 10 times, and the tumor size (G) and animal survival (H) was monitored. Tumor growth was measured two weeks after inoculation (n=7). Student's t test was used for statistical analysis. **P<0.01; *P<0.05. Log-rank test was used to determine differences between survivals of each group.

Figure 7:
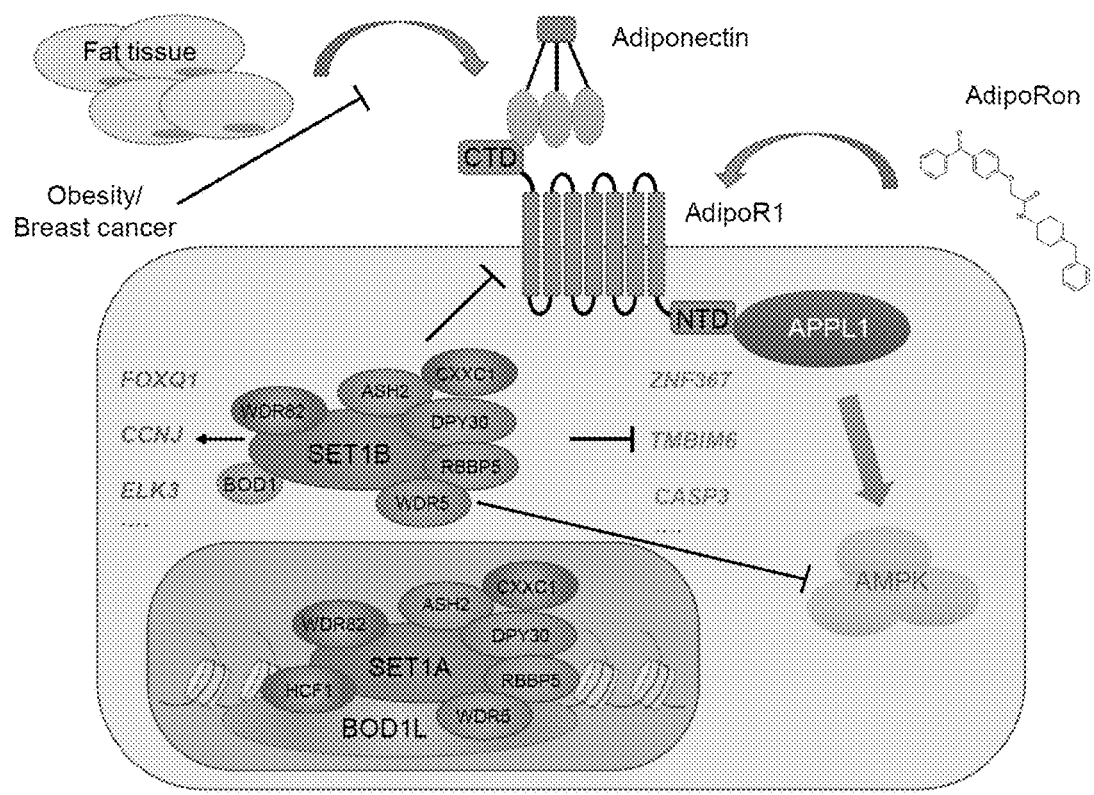

FIG. 7. Model. In human cells, SET1B/COMPASS functions as a cytoplasmic complex, and plays central role in mediating gene expression in H3K4 methylation-independent manner. Loss of SET1B/COMPASS leads to the activation of AdipoR1 signaling, which is greatly suppressed in breast cancer patients or obese people. Reactivating AdipoR1 signaling in human breast cancer by small molecule agonist provides a novel therapeutic strategy for TNBC treatment.

Figure 8:
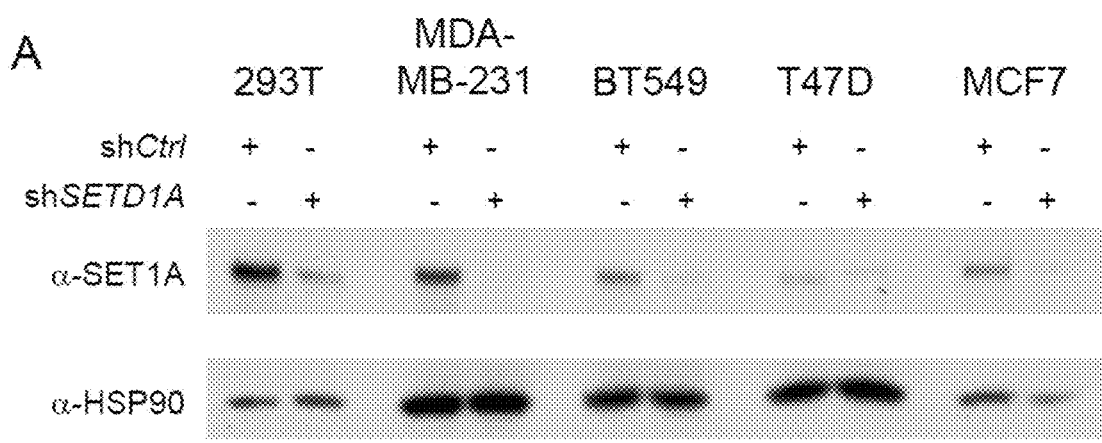
Figure 8:
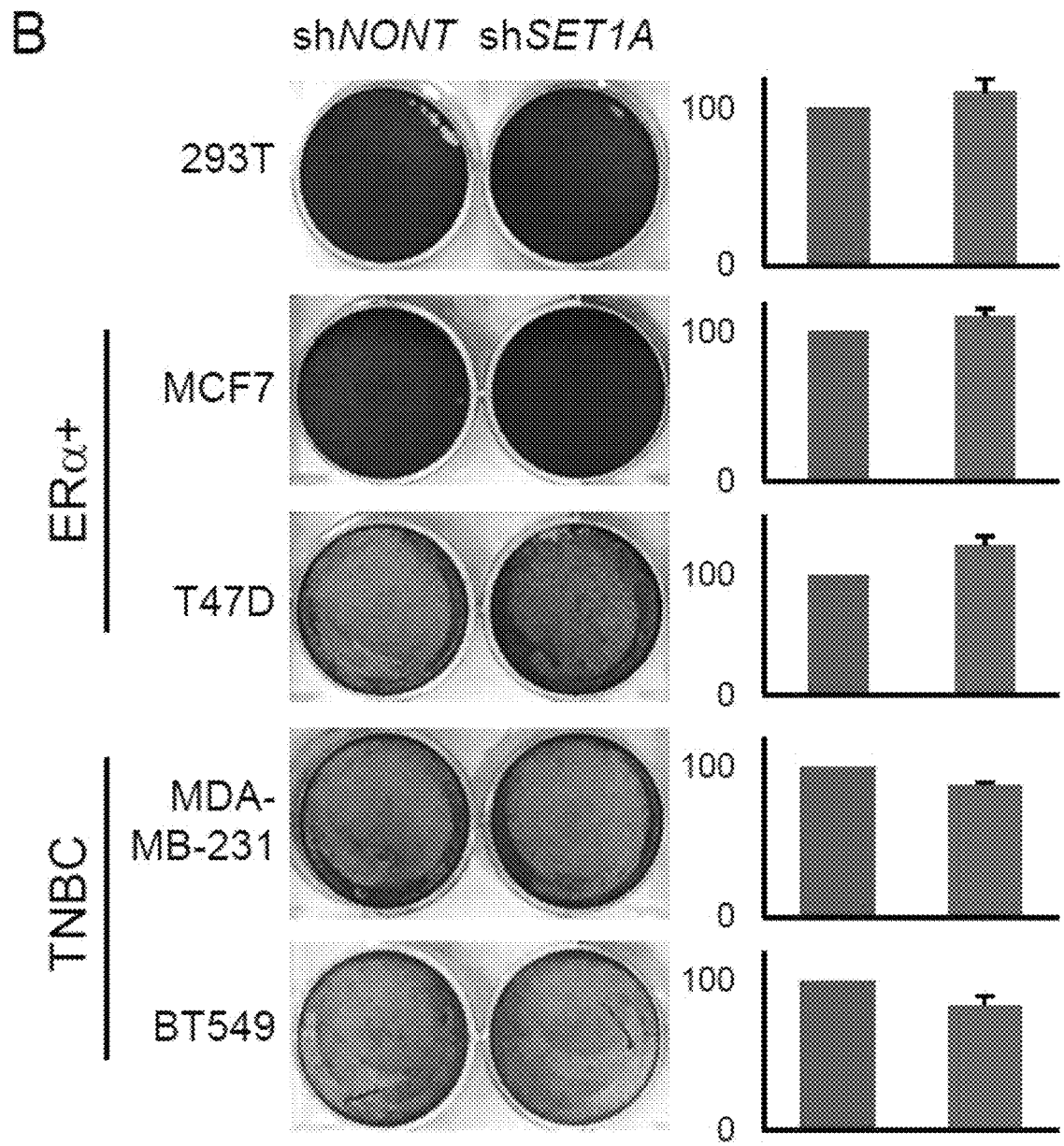
Figure 8:
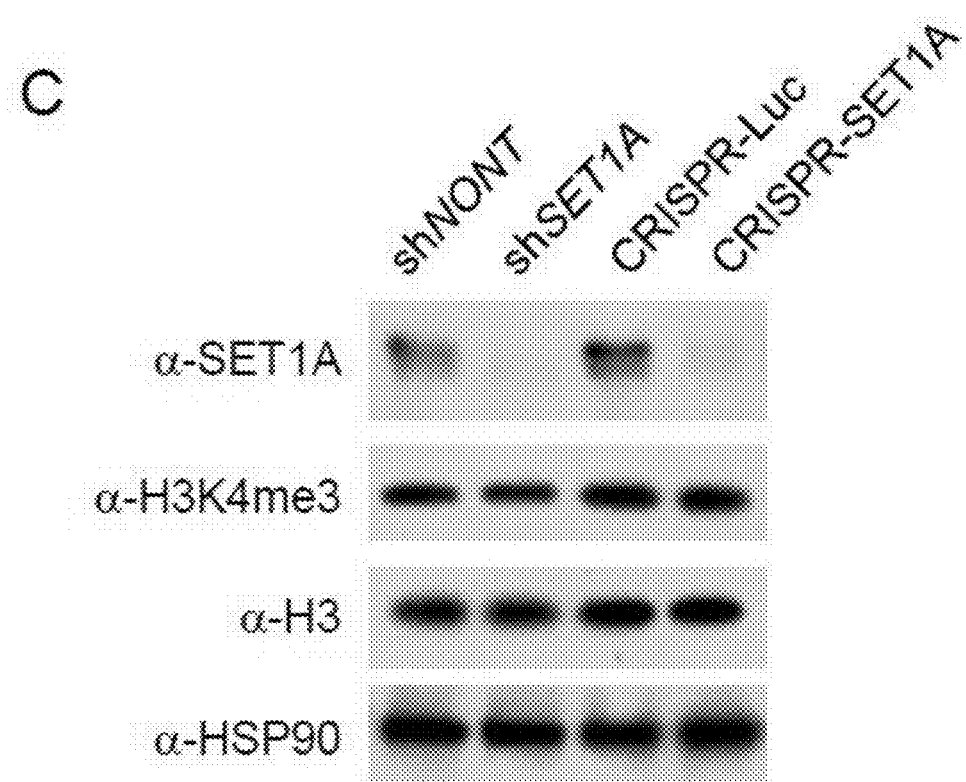
Figure 8:
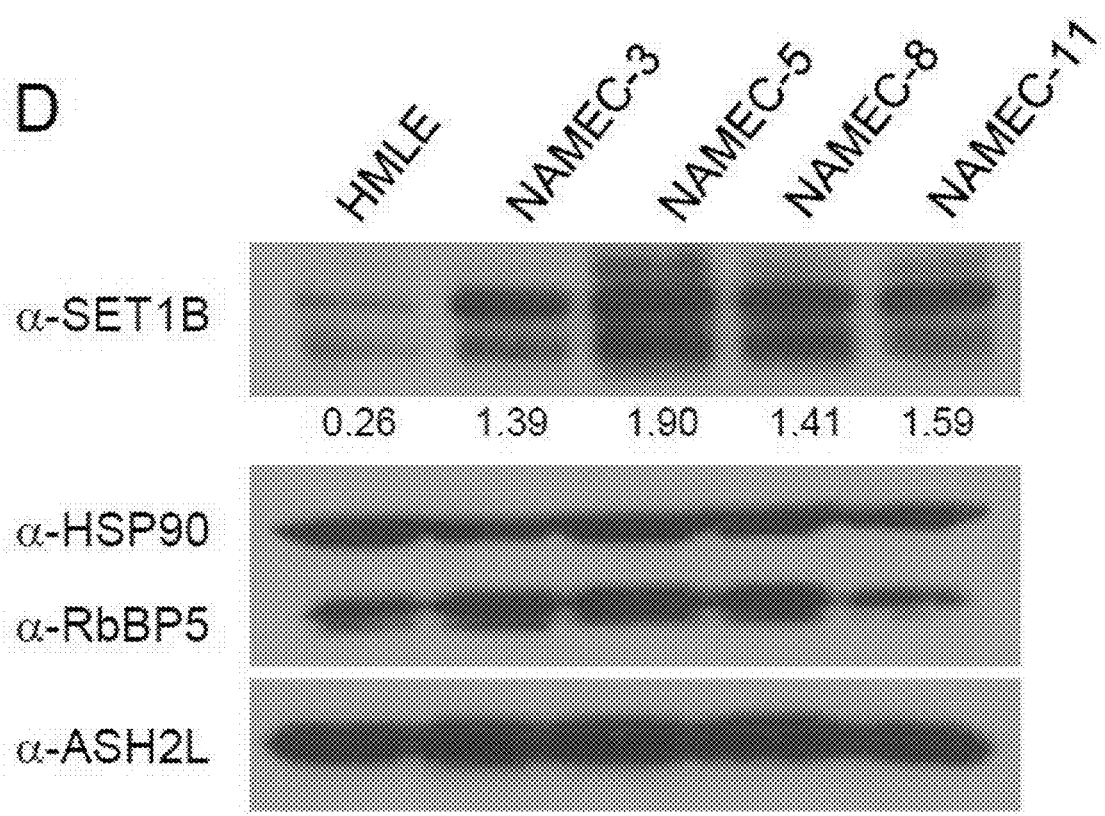

FIG. 8. SET1A is not essential for human breast cancer cells. A) SET1A was knocked down in five cell lines including HEK293T, MDA-MB-231, BT549, T47D, and MCF7 cells. The protein level of SET1A was determined by western blotting, which further quantified by ImageJ software, n=3. B) Cells in panel A were selected with puromycin for 48 hours, $4\times10^4$ living cells were seeded in 6-well plates and grown for one week before crystal violet staining (level panel). Quantification of crystal violet staining was determined as described in materials section. n=4, Student's t test was used for statistical analysis. **P<0.01; *P<0.05. Error bars represent sd. (right panel). C) SET1A was depleted by its specific shRNA or CRISPR-CAS9. The protein level of SET1A and H3K4me3 was determined by western blot. Total Histone H3 as well as HSP90 was used as control. n=3. D) The protein levels of SET1B, RBBP5, and ASH2L were detected by Western blotting in human normal epithelia cells (HMLE) and its malignant transformed sub-cell lines (NAMEC3-11). HSP90 was used as the internal control. This result was quantified by ImageJ software, n=3.

Figure 9:
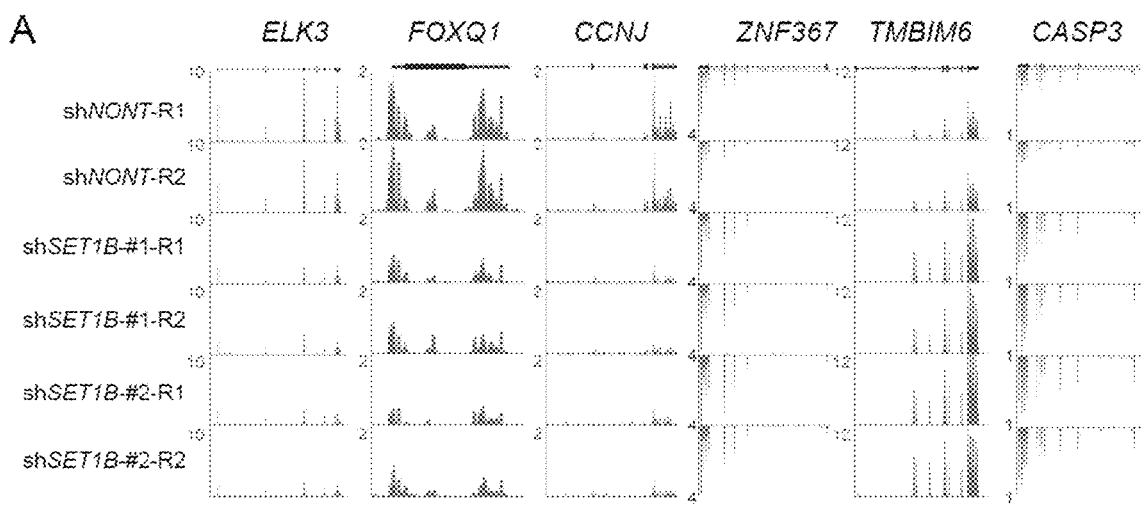
Figure 9:
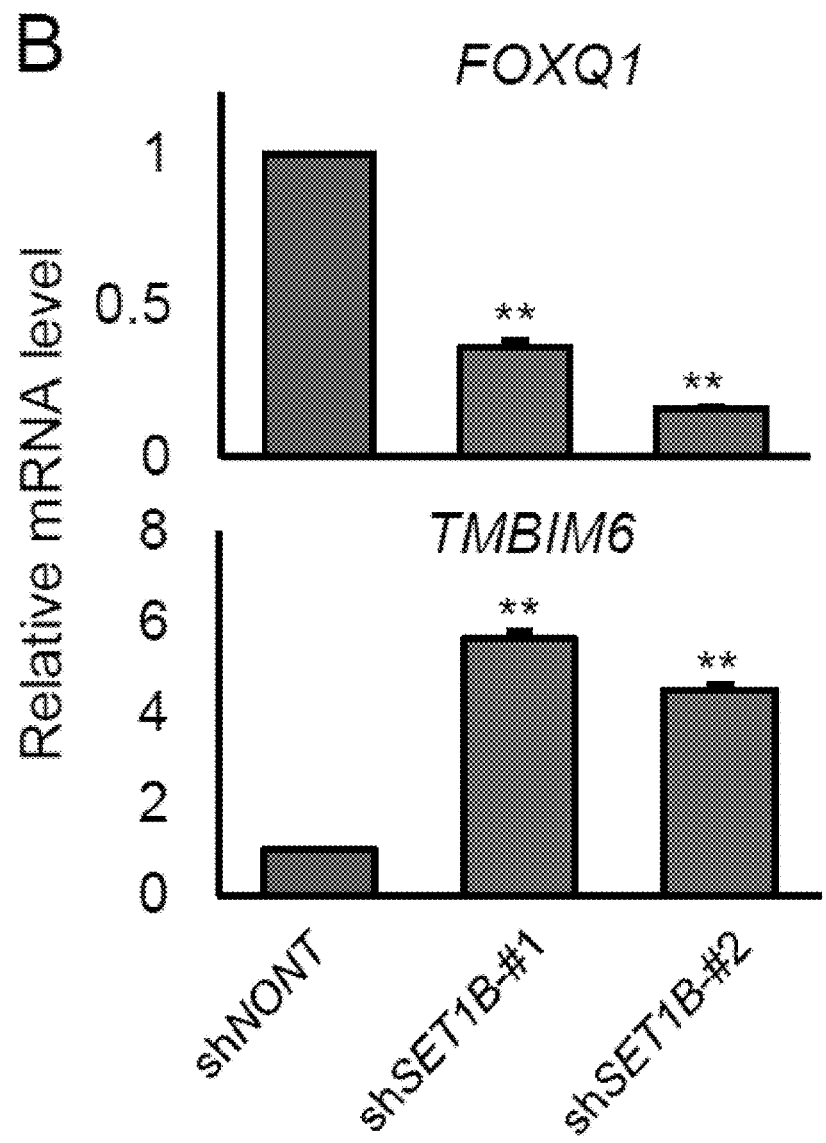
Figure 9:
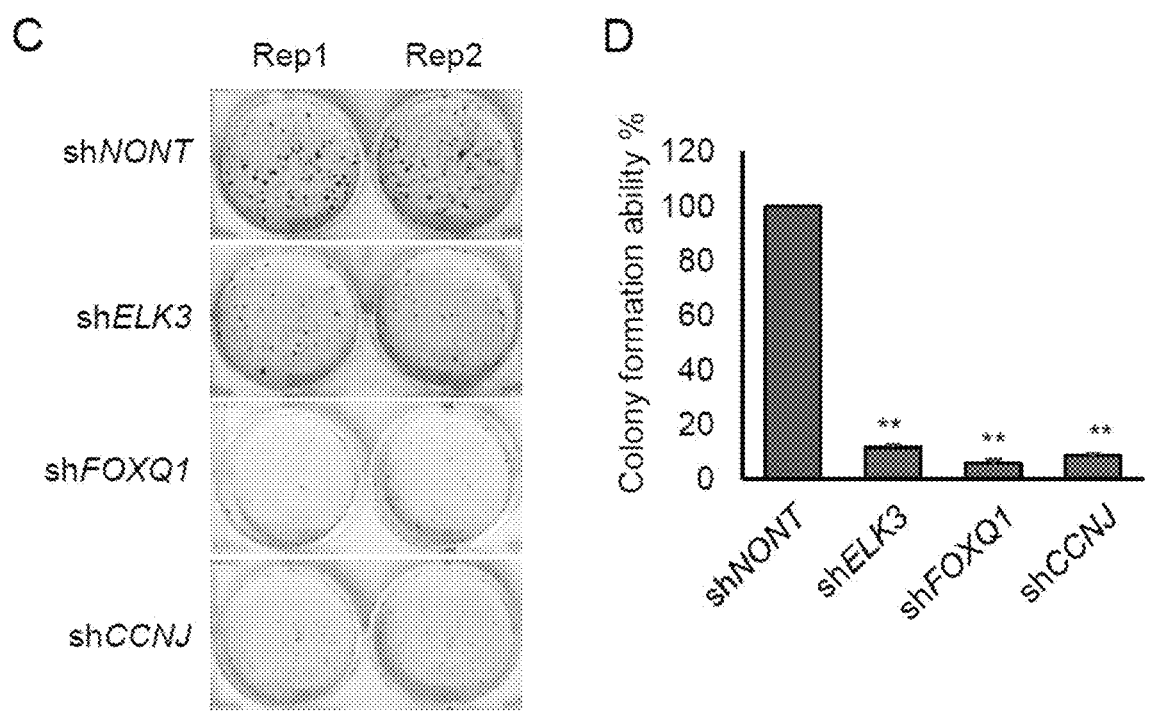
Figure 9:
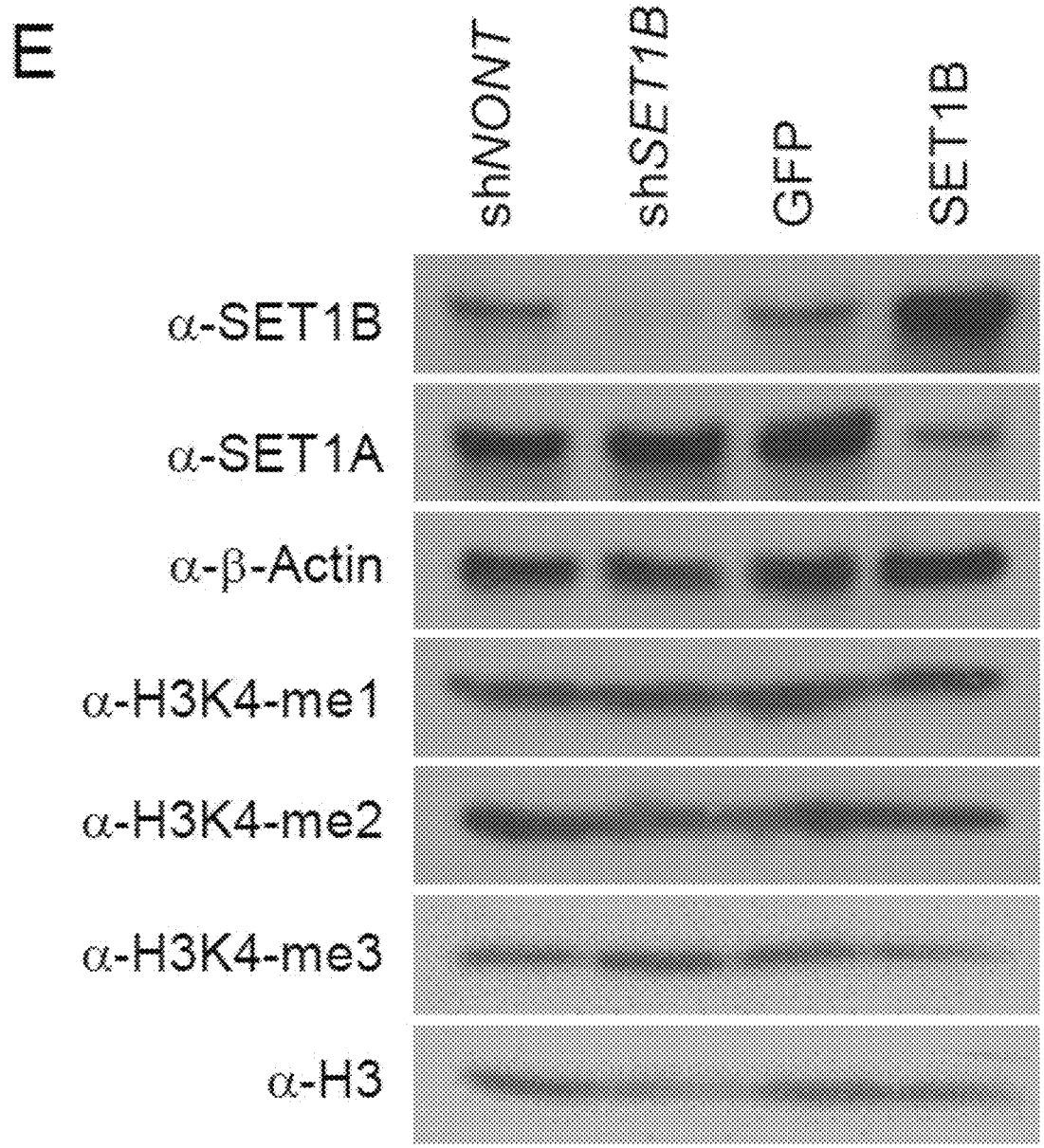
Figure 9:
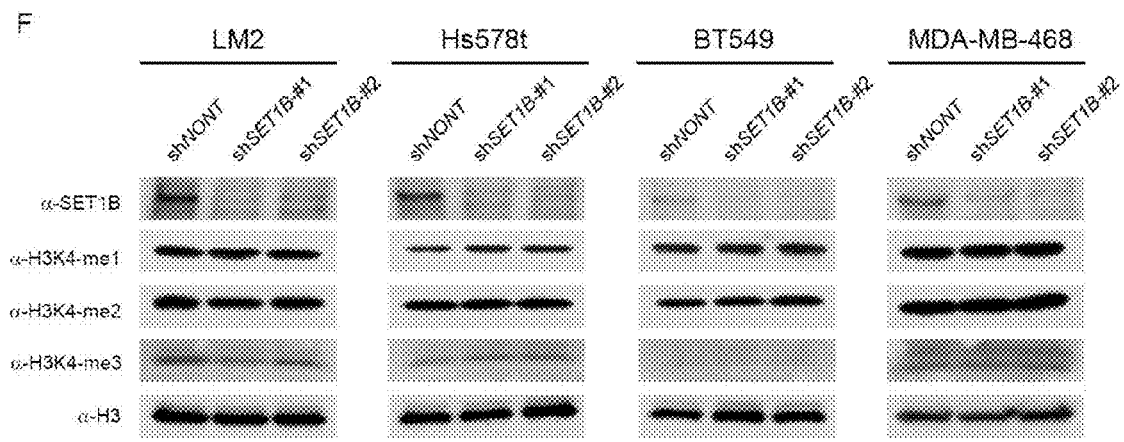

FIG. 9. Loss of SET1B does not affect histone H3K4 modifications. A) Representative tracks of ELK3, FOXQ1, CCNJ, ZNF367, TMBIM6 and CASP3 in MDA-MB-231 cells infected with shNONT, shSET1B-#1 and shSET1B-#2 virus were shown. B) The gene expression of FOXQ1 and TMBIM6 was in shNONT and shSET1B cells was further validated by real-time PCR. n=3, Student's t test was used for statistical analysis. **P<0.01; *P<0.05. Error bars represent sd. C) ELK3, FOXQ1, and CCNJ3 were knocked down in MDA-MB-231 cells. After puromycin selection, 500 living cells were seeded in 6-well plates for two weeks. The colony formation ability was determined by crystal violet staining. D) Quantification of crystal violet staining was determined as described in materials section. n=4, Student's t test was used for statistical analysis. **P<0.01; *P<0.05. Error bars represent sd. E) MCF7 cells were infected with retroviruses expressing Flag-tagged SET1B or lentiviruses expressing shSET1B. The protein levels of SET1B, SET1A, histone H3K4me1, H3K4me2, and H3K4me3 were determined by Western blotting. F) SET1B was knocked down in four triple-negative breast cancer lines, LM2, Hs578t, MDA-MB-468, and BT549 cells. Whole cell lysates were extracted and the protein levels of SET1B, H3K4me1, H3K4me2, and H3K4me3 were detected by Western blotting. Total histone H3 was used as the internal control.

Figure 10:
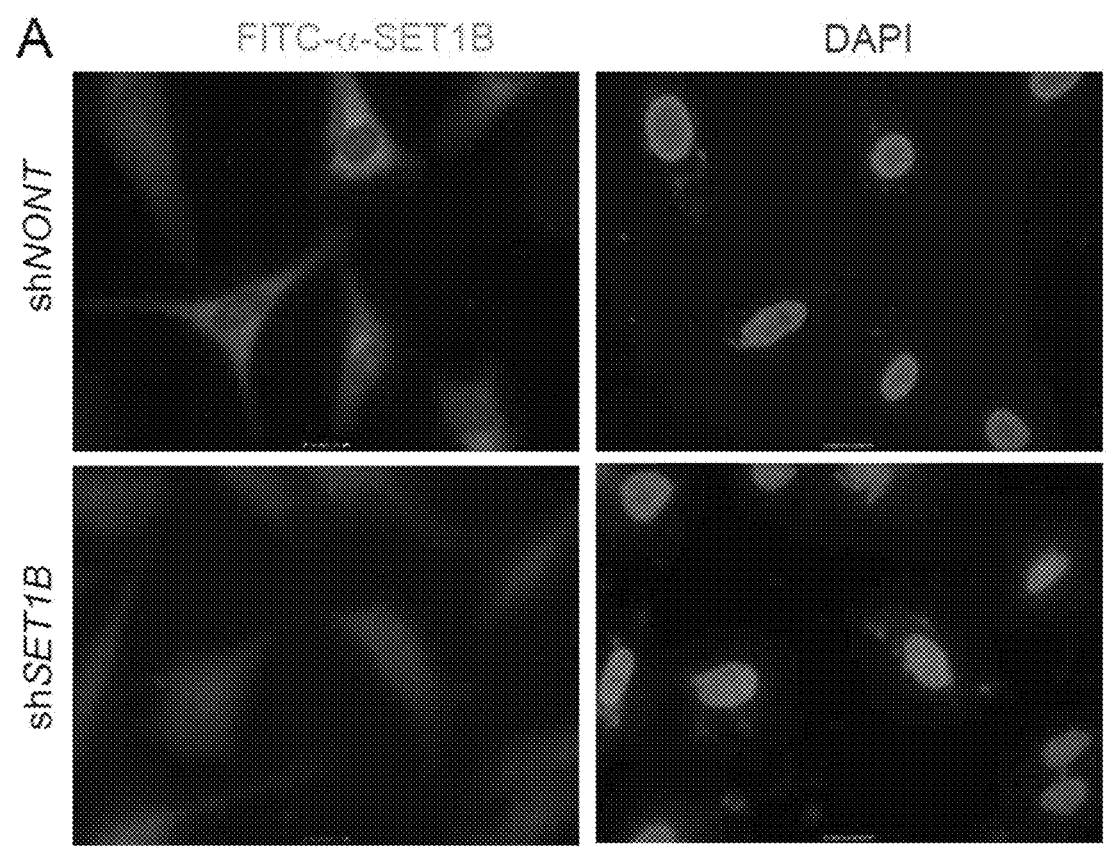
Figure 10:
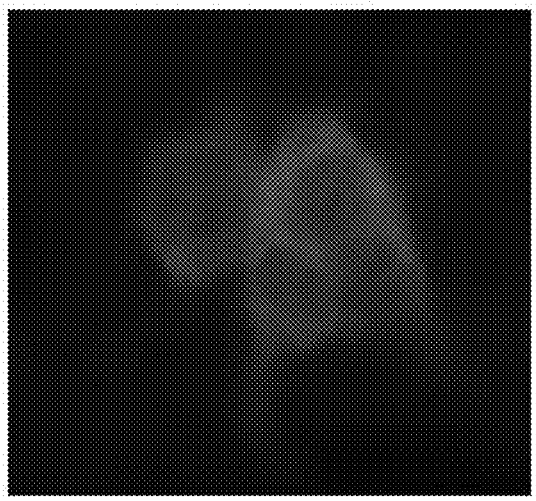
Figure 10:
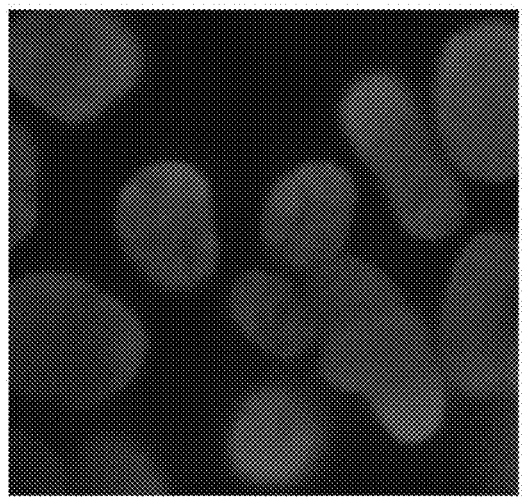
Figure 10:
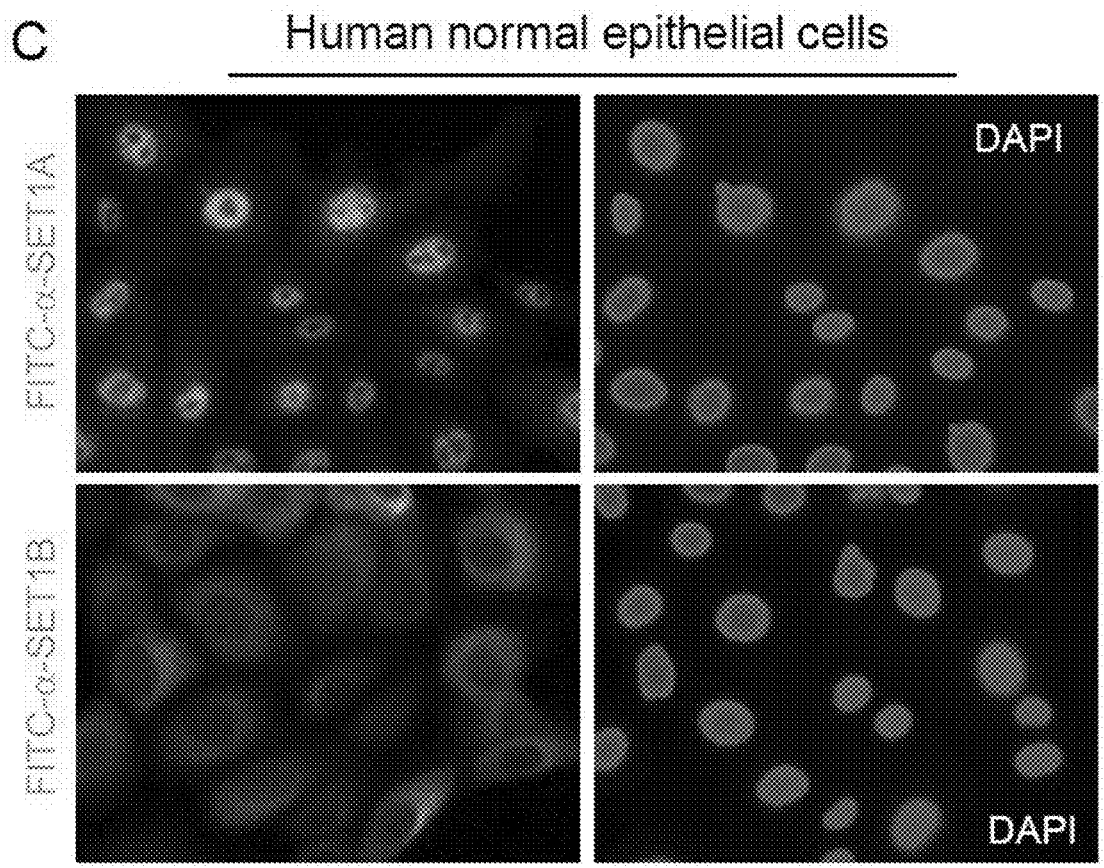
Figure 10:
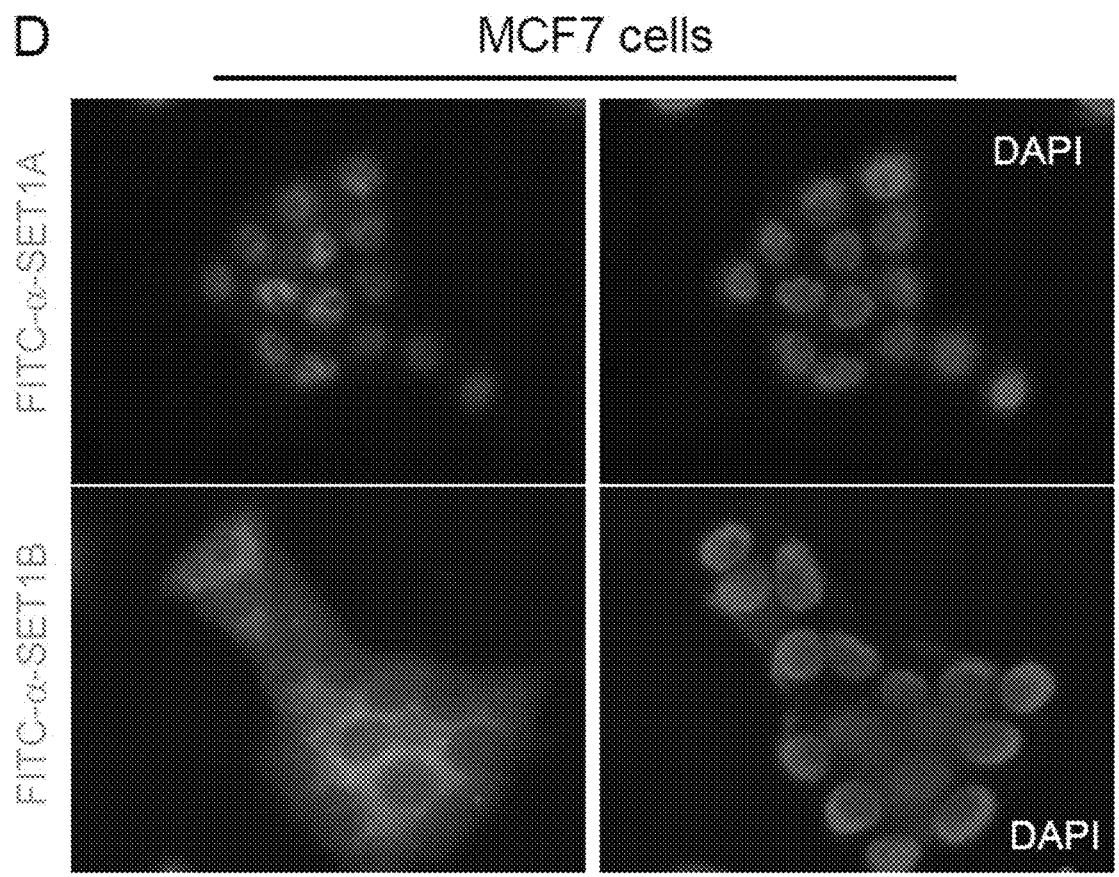
Figure 10:
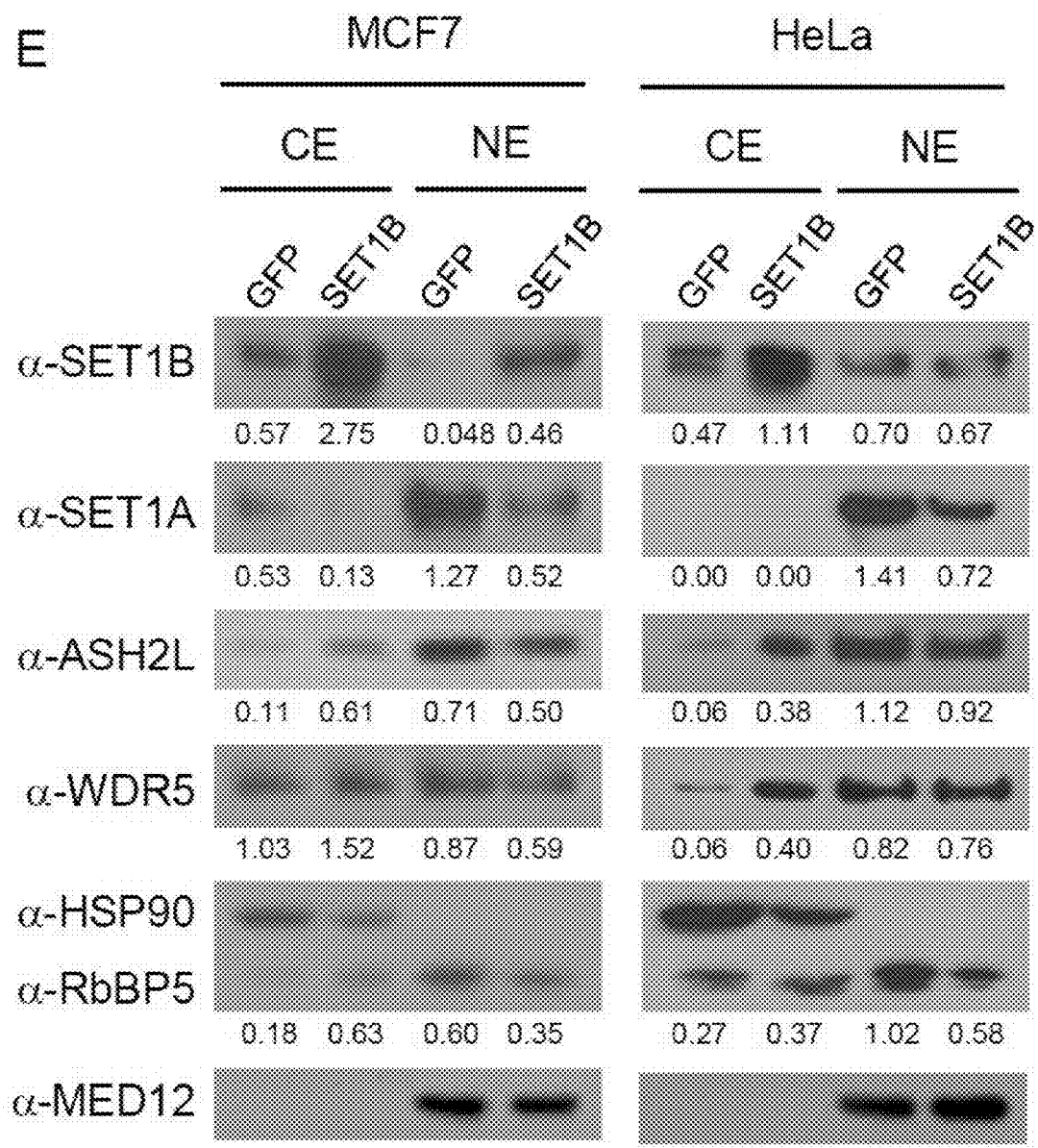

FIG. 10. SET1B complex is a major cytoplasmic COMPASS. A) SET1B was knocked down in HeLa cells. The endogenous SET1B protein levels were detected by immunofluorescence, n=4. B) HEK293T cells were transfected with Flag-SET1B. Immunofluorescence was performed with anti-Flag 24 hours after transfection, n=4. The endogenous protein of SET1B in HMLE cells (C) and MCF7 cells (D) was detected by immunofluorescence, n=4. E) MCF7 cells and HeLa cells were infected with retroviruses expressing Flag-SET1B. The protein levels of SET1B, SET1A, ASH2L, RBBP5, and WDR5 in both cytoplasmic and nuclear extracts were detected by Western blotting. HSP90 was used as a cytoplasmic fractionation marker, MED12 protein was used as a nuclear fractionation marker. The cytoplasmic protein was normalized to HSP90 protein level, and the nuclear protein was normalized to MED12 protein level. The results from the western blot was quantified by ImageJ software, n=3.

Figure 11:
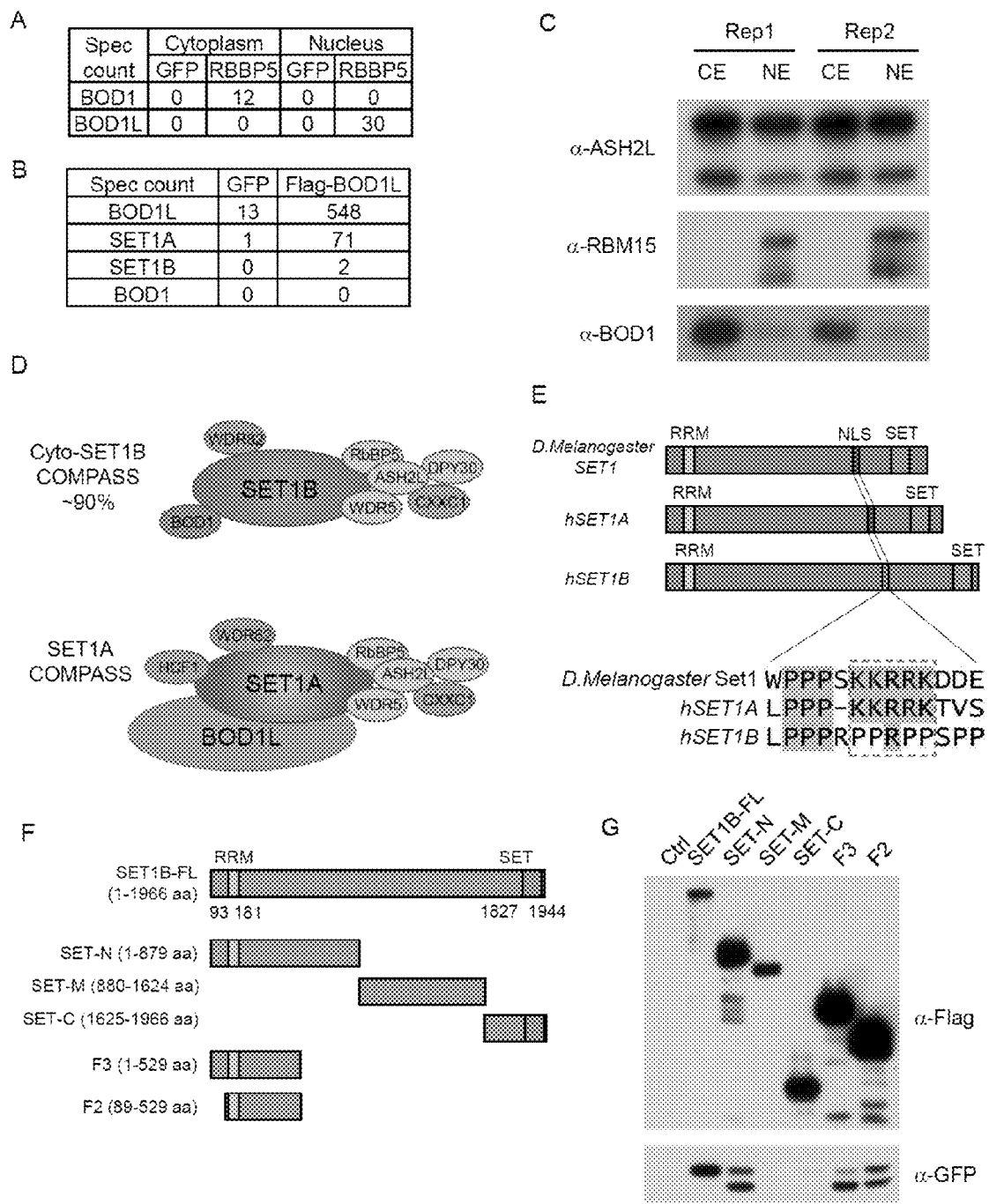

FIG. 11. BOD1 is a cytoplasm-specific subunit of SET1B/COMPASS. A) Spec count of BOD1 and BOD1L co-purified with RBBP5 in FIG. 3C are indicated in the table. B) HEK293T cells were transfected with plasmid expressing either GFP or Flag-tagged BOD1L. Nuclear extract was prepared from cells 48 hours after transfection and incubated with M2 beads. The interacting proteins of BOD1L were analyzed by mass spectrometry. Spec count of BOD1L, SET1A, SET1B, and BOD1 are shown in the table. C) The protein levels of ASH2L, RBM15, and BOD1 were determined by Western blotting with purified cyto-SET1B COMPASS and nuc-SET1B COMPASS, n=3. D) Cartoon depictions of cyto-SET1B COMPASS, and SET1A COMPASS. The WARD complex, which contains WDR5, ASH2L, RBBP5, and DPY30 is shown in orange; SET1A/B COMPASS complexes-specific subunits WDR82 and CXXC1 are shown in gray. Cyto-SET1B COMPASS-specific subunit BOD1 is shown in pink. E) CLUSTALW alignment of the NLS conserved between *Drosophila* SET1, human SET1A and the corresponding region of human SET1B, with conserved residues highlighted in gray. F) Schematic diagram of SET1B full-length cDNA and truncated derivatives, each with a Flag-tag fused to its N-terminus is shown. G) Plasmids expressing the SET1B cDNA derivatives shown in E) were transiently transfected into HEK293T cells together with GFP-BOD1 for 24 hours. The Flag-tagged SET1B truncations were then purified and the interacting GFP-BOD1 was detected by Western blotting with anti-GFP, n=4.

Figure 12:
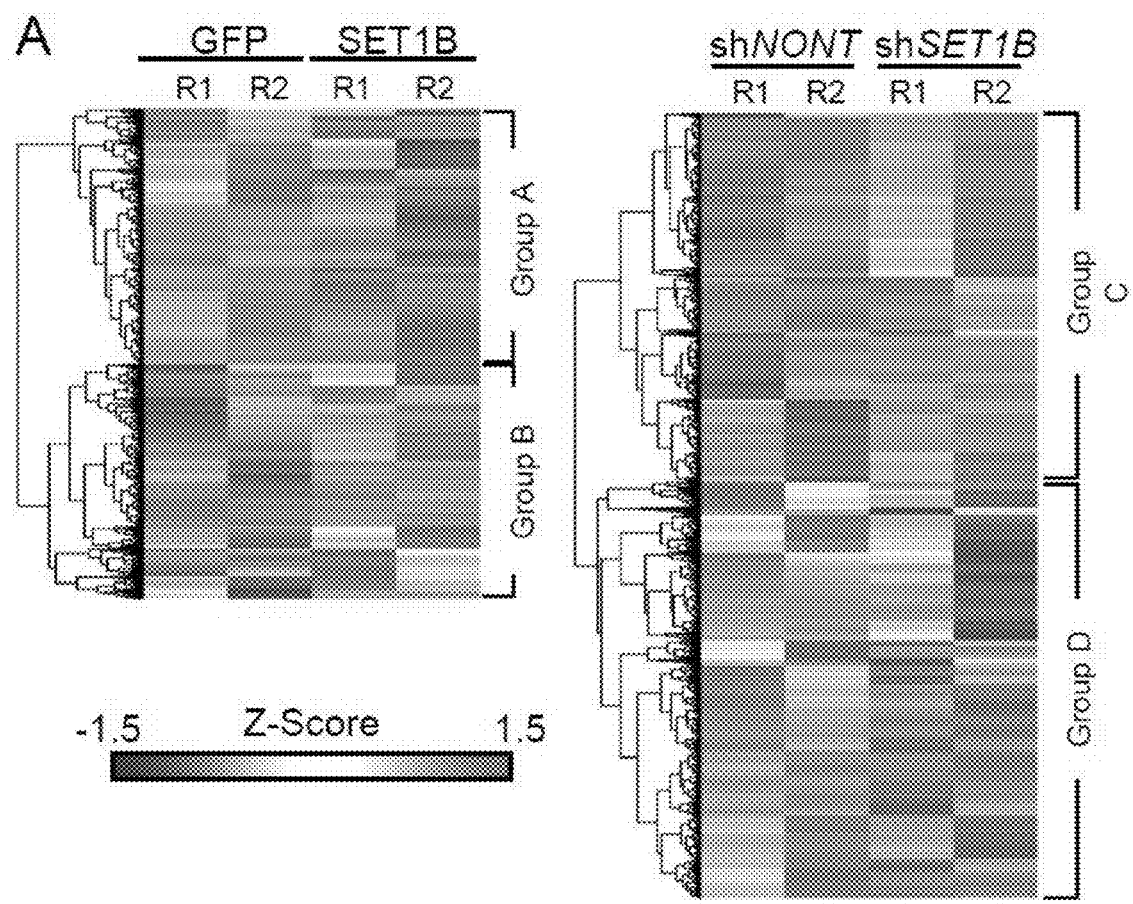
Figure 12:
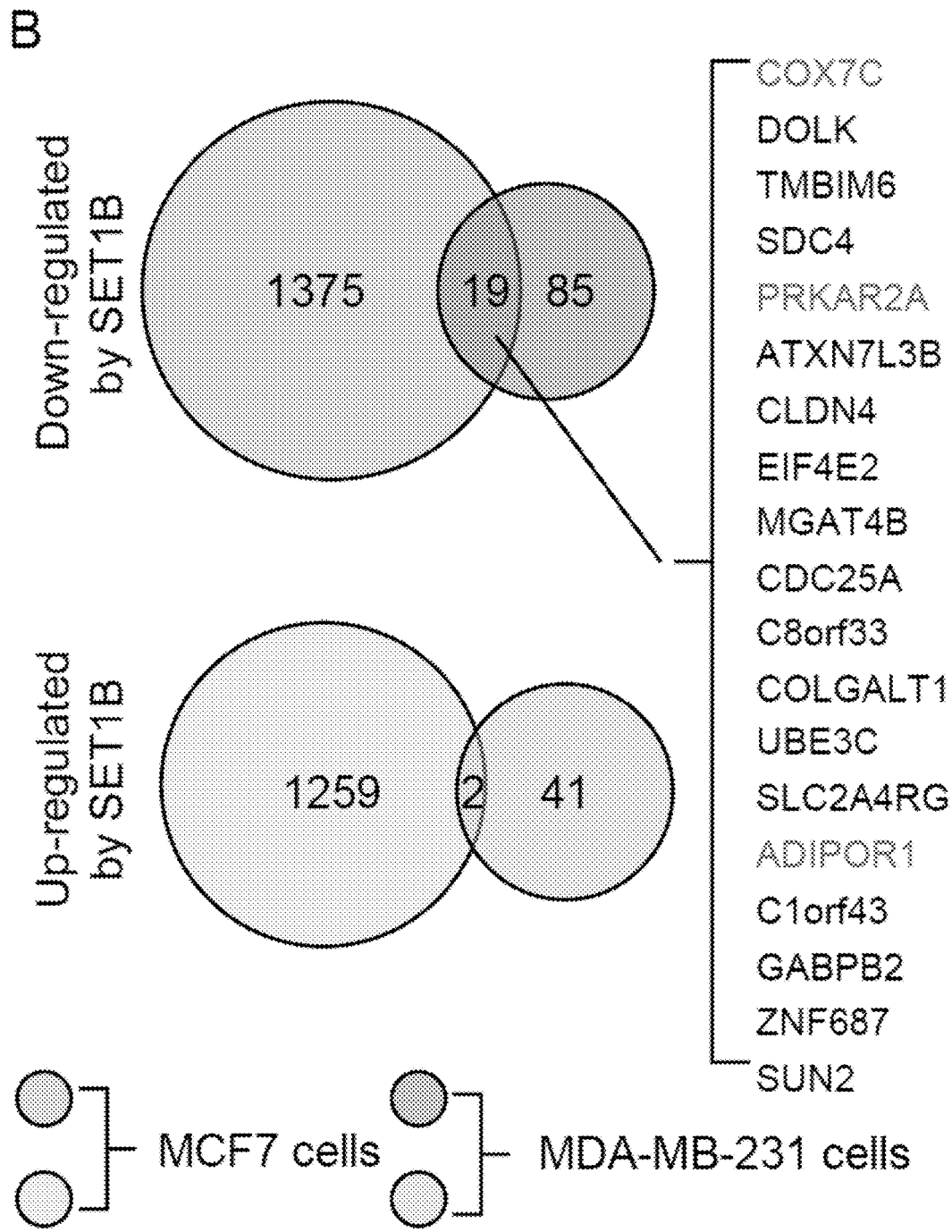
Figure 12:
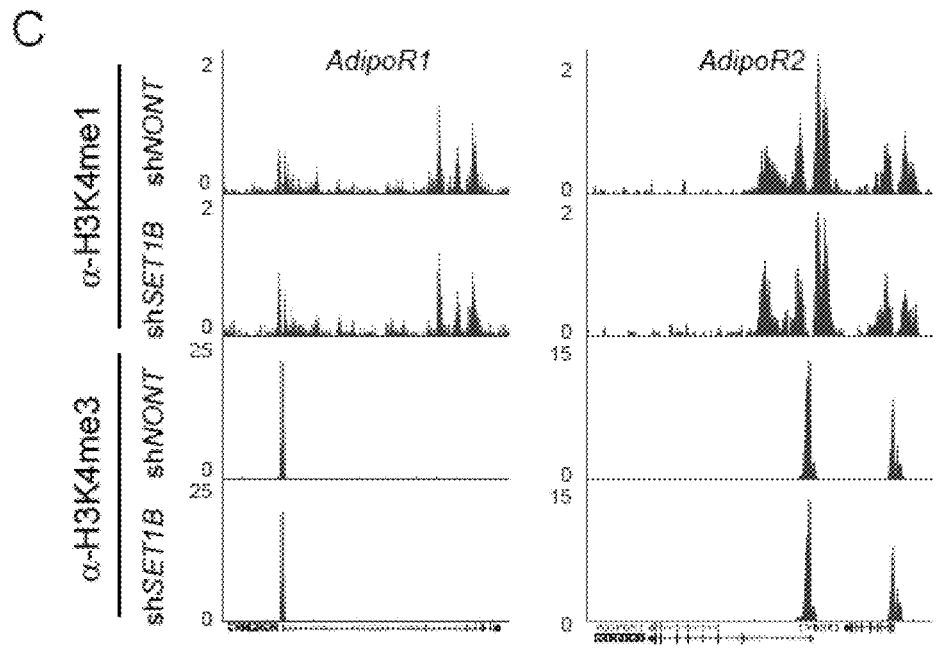
Figure 12:
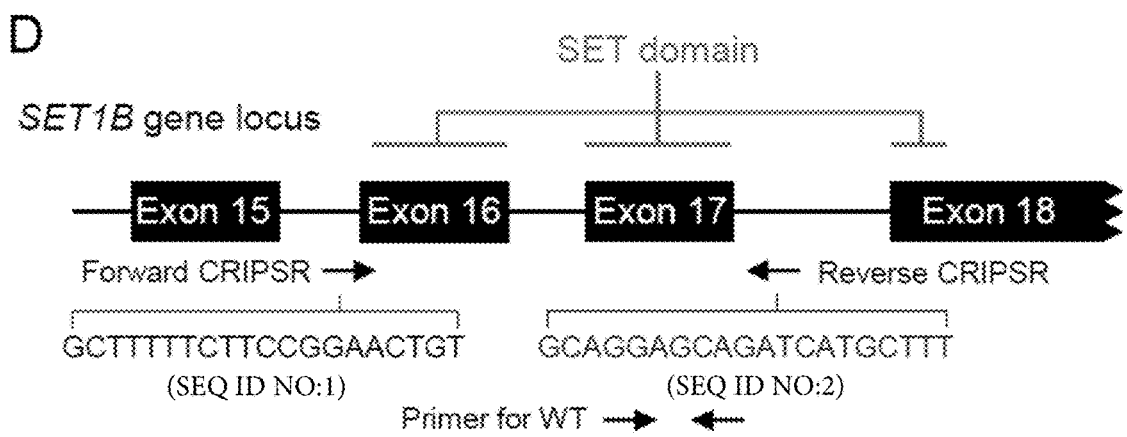
Figure 12:
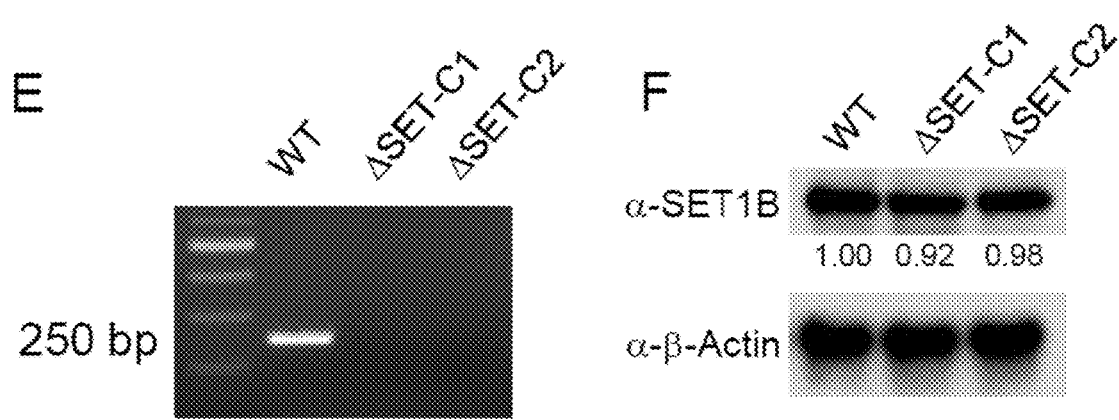
Figure 12:
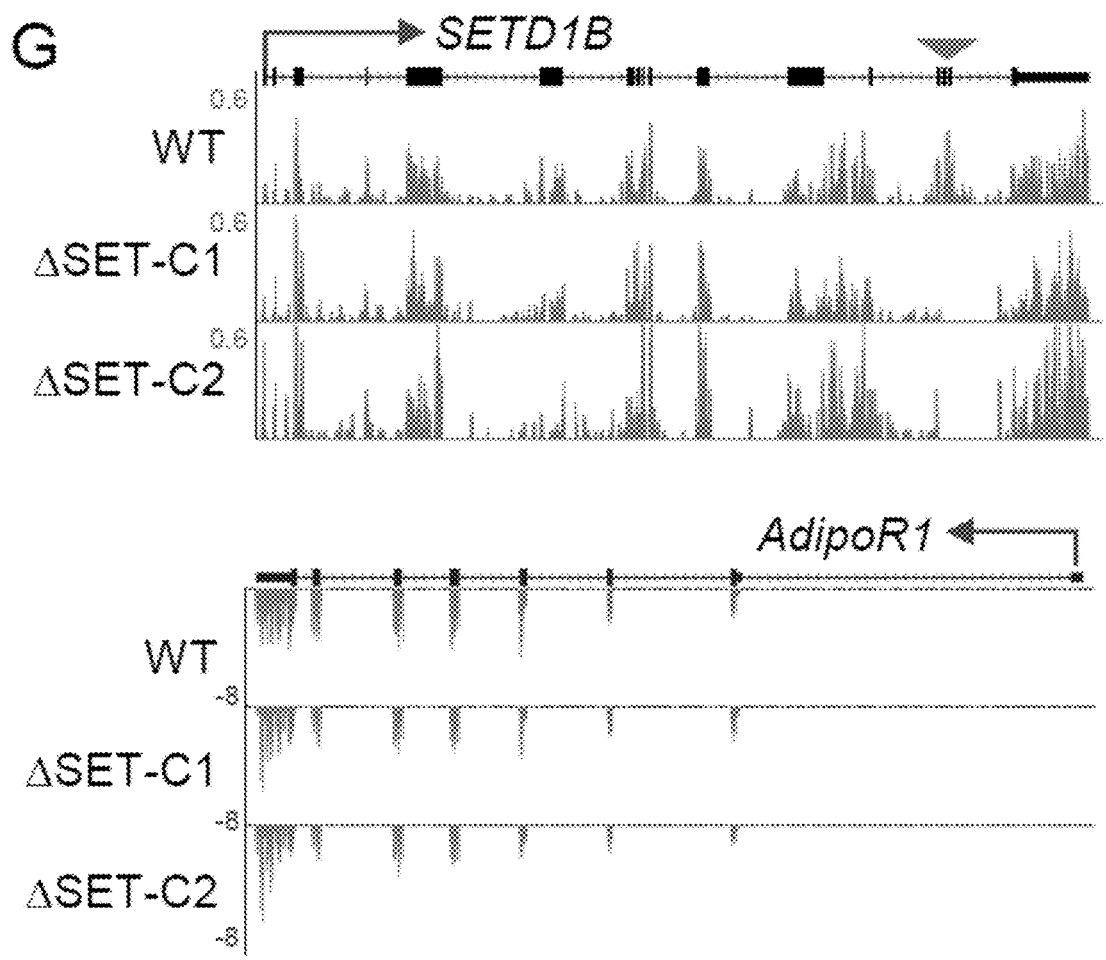
Figure 12:
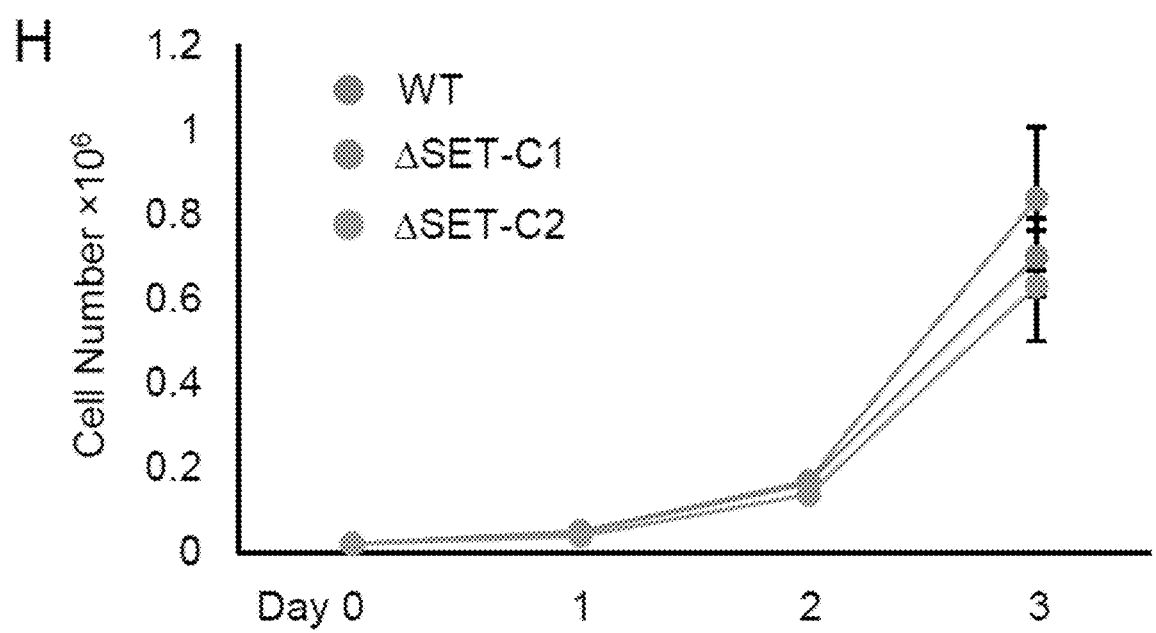

FIG. 12. SET1B regulates AdipoR1 expression in catalytic activity independent manner. A) RNA-seq was performed in MCF7 cells that were infected with retroviruses expressing Flag-tagged SET1B or lentiviruses expressing shSET1B. Heatmap shows the genes regulated by SET1B in either over-expressing system (left panel) or the knockdown condition (right panel), two replicates. B) Genes regulated by SET1B in both ER+ cells (MCF7 cells) and triple-negative cells (MDA-MB-231 cells) are shown in the Venn diagram. The ADIPOR1 signaling genes COX7C, PRKAR2A, and ADIPOR1 are indicated. C) Genome browser track examples of H3K4me1 and H3K4me3 ChIP-seq in MDA-MB-231 cells transduced with shCtrl, shSET1B for ADIPOR1 and ADIPOR2 genes. The x-axis indicates the chromosome position, and the y-axis represents normalized read density in reads per million (rpm). D) Design of CRIPSR-Cas9 targeting the catalytic domain of SETD1B gene locus. E) PCR was performed for genotyping in SET-domain wildtype and knockout cells. F) The protein level of SET1B was determined by western blot in wild-type cells and two SET-domain deleted clones. G) Representative tracks shows SETD1B gene and AdipoR1 gene in wild-type cells and two SET-domain deleted clones. H) Proliferation ability of SET1B-SET-domain wildtype or deleted cells were determined by cell counting.

Figure 13:
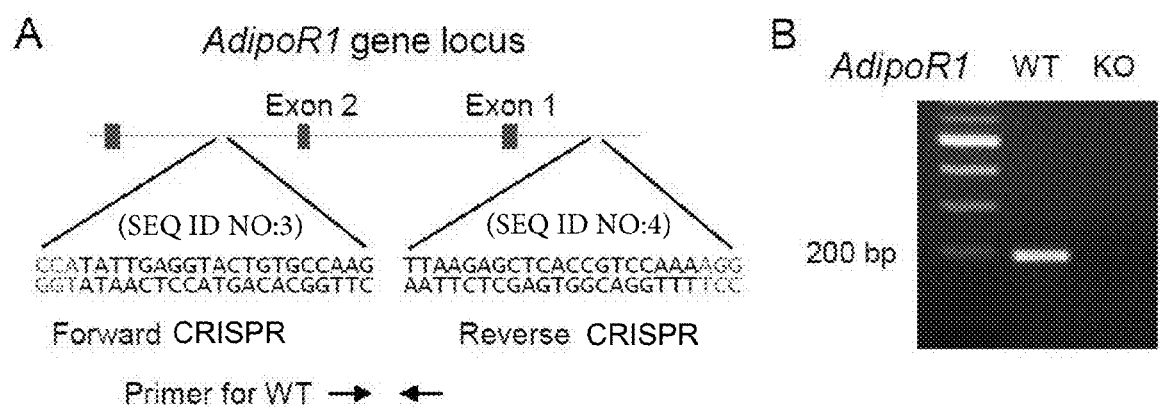
Figure 13:
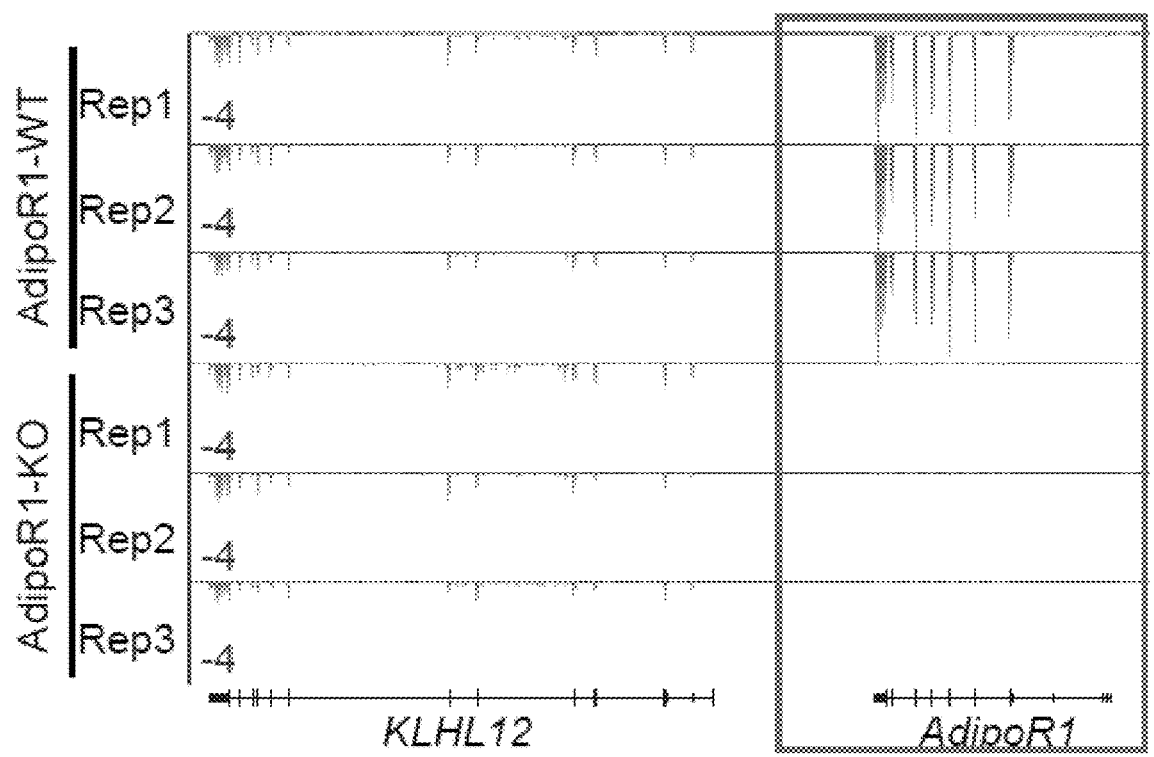
Figure 13:
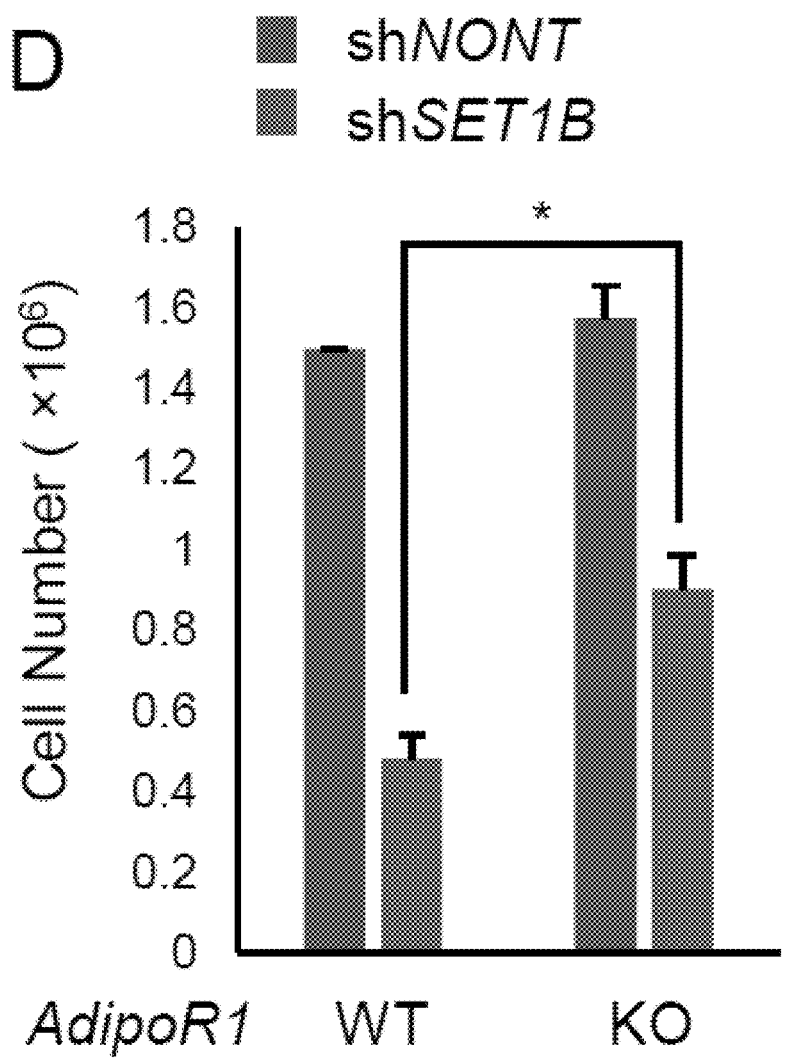
Figure 13:
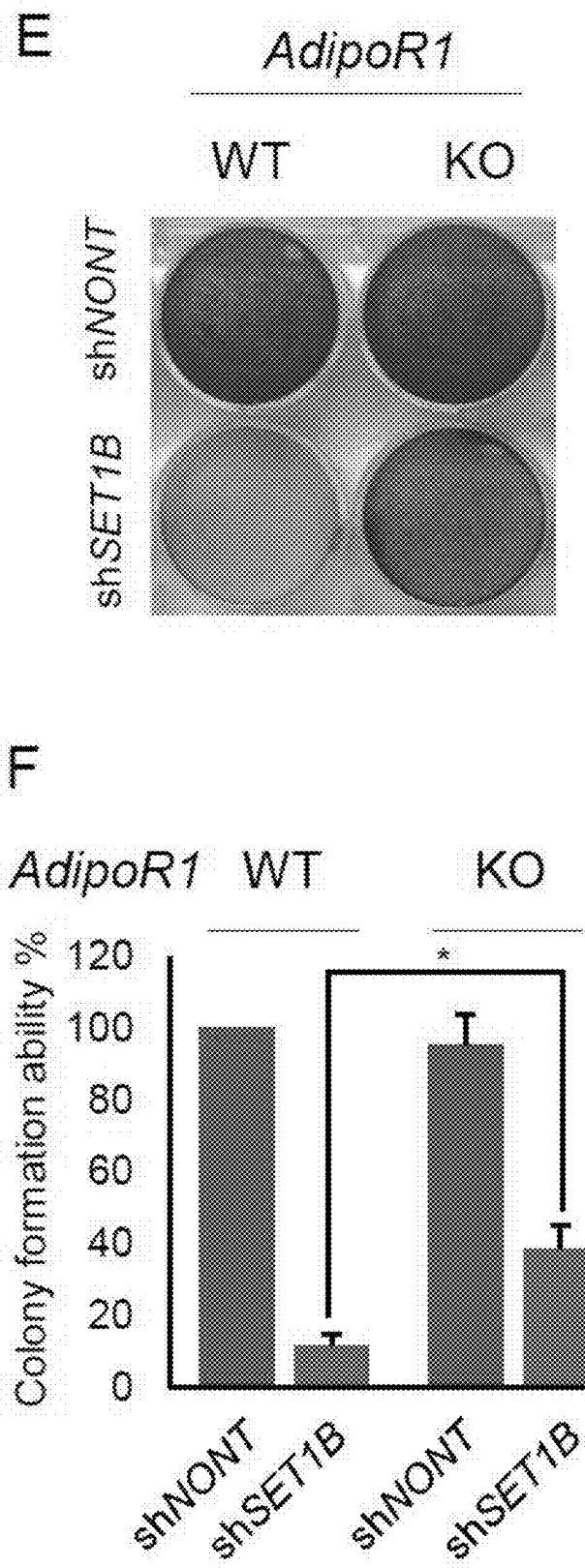
Figure 13:
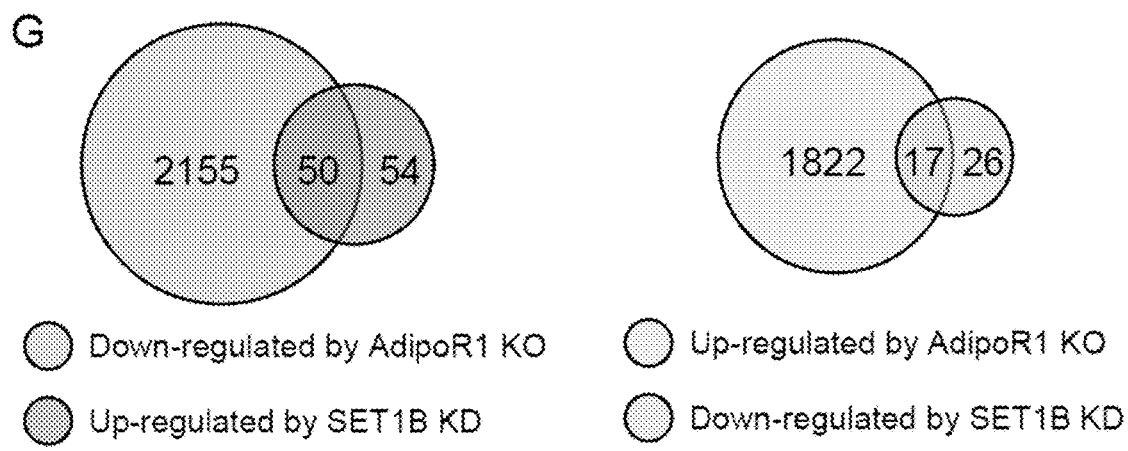
Figure 13:
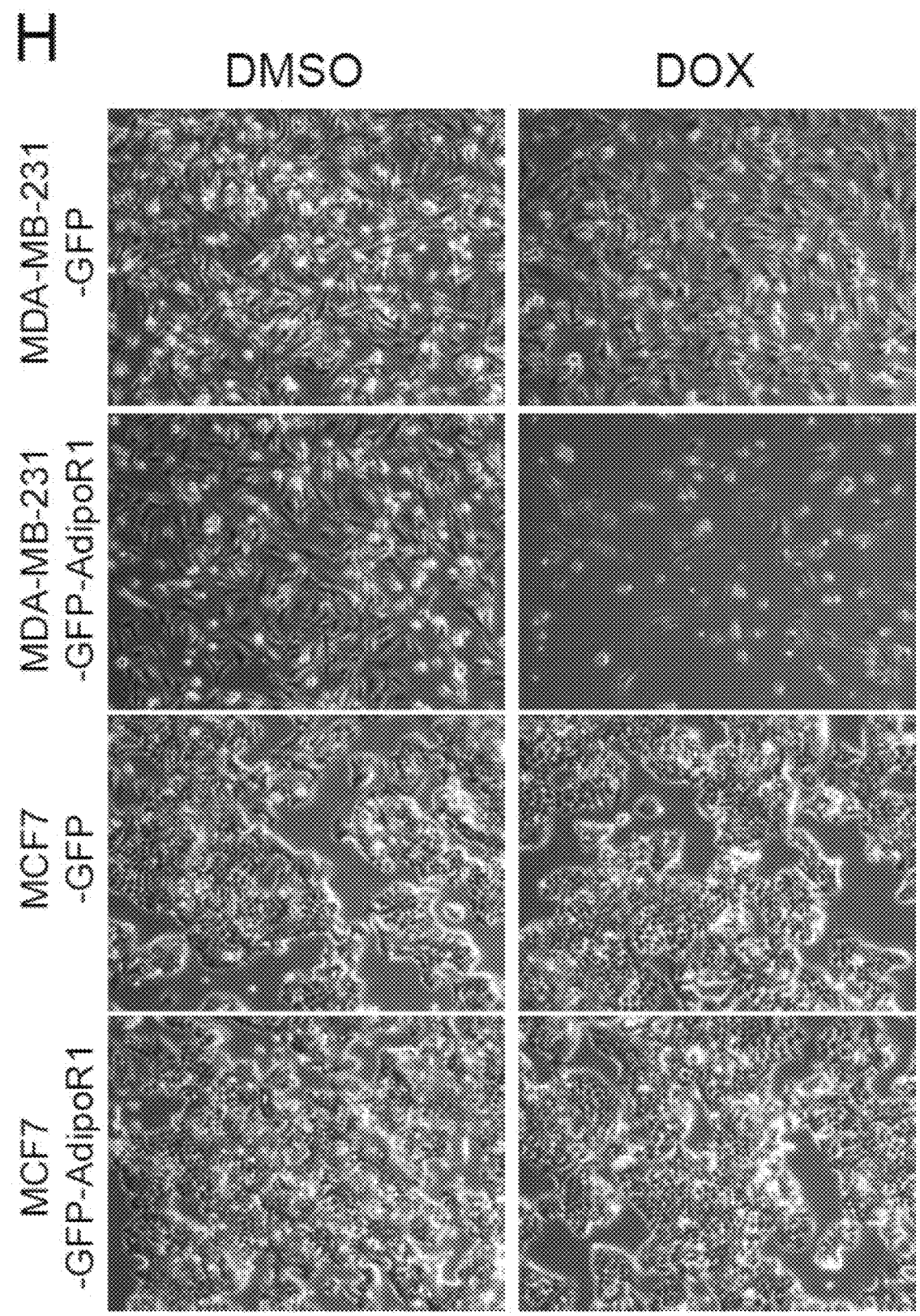
Figure 13:
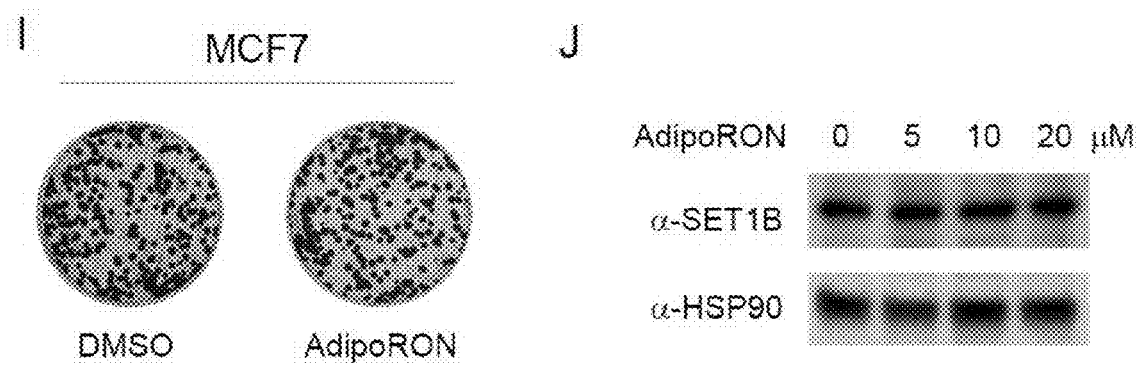

FIG. 13. Depletion of AdipoR1 by CRIPSR-CAS9 partially rescued cell death induced by SET1B depletion. A) Design of CRIPSR-Cas9 targeting ADIPOR1 gene locus. B) PCR was performed for genotyping of AdipoR1 wildtype and deleted cells. C) Total RNA was extracted from AdipoR1-WT and AdipoR1-KO cells and subjected to RNA-seq, three replicates. Representative tracks of AdipoR1 gene are shown. D) SET1B was further knocked down in ADIPOR1-WT and ADIPOR1-KO cells, respectively. After puromycin selection for 48 hours, $1 \times 10^5$ cells were seeded in 6-well plate, the cell viability of SET1B knocked down cells was determined by cell counting. E) The cells from panel C were seeded in 6-well plate ($1 \times 10^4$) and grown for one week before crystal violet staining. F) Quantification of crystal violet staining was determined as described in materials section. n=4, Student's t test was used for statistical analysis. **P<0.01; *P<0.05. Error bars represent sd. G) Van diagram shows the common genes that are regulated by both SET1B and ADIPOR1, two replicates. H) Cell morphology of GFP or GFP-AdipoR1 inducible cell lines after DMSO or Dox treatment, n=3. I) MCF7 cells were seeded in 6-well plates at the concentration of 500 cells per well. The cells were treated with either DMSO or AdipoRON (10 µM) for three weeks, and the colonies were stained with crystal violet. J) MDA-MB-231 cells were treated with various concentrations of AdipoRON for 24 hours. The protein level of SET1B was determined by western blot. HSP90 was used as internal control, n=3.

Figure 14:
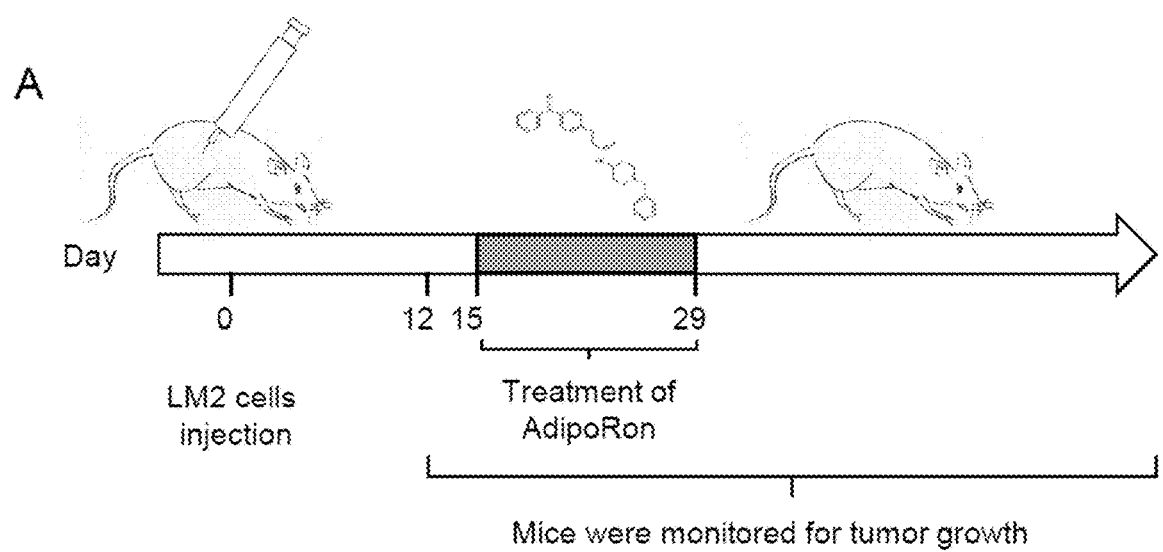
Figure 14:
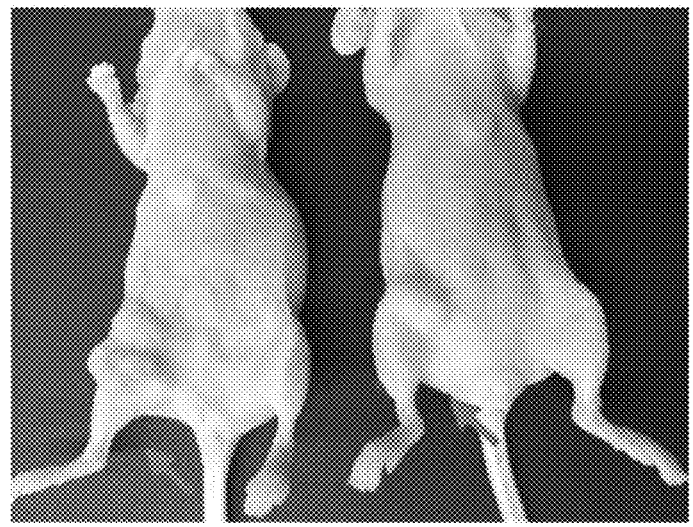
Figure 14:
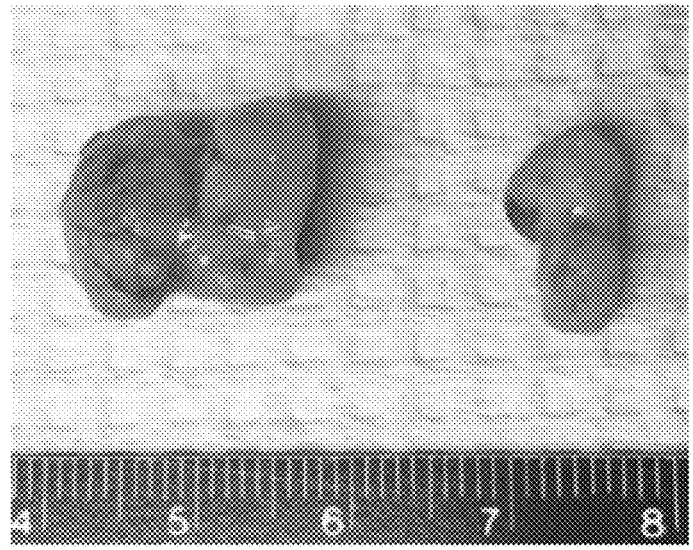
Figure 14:
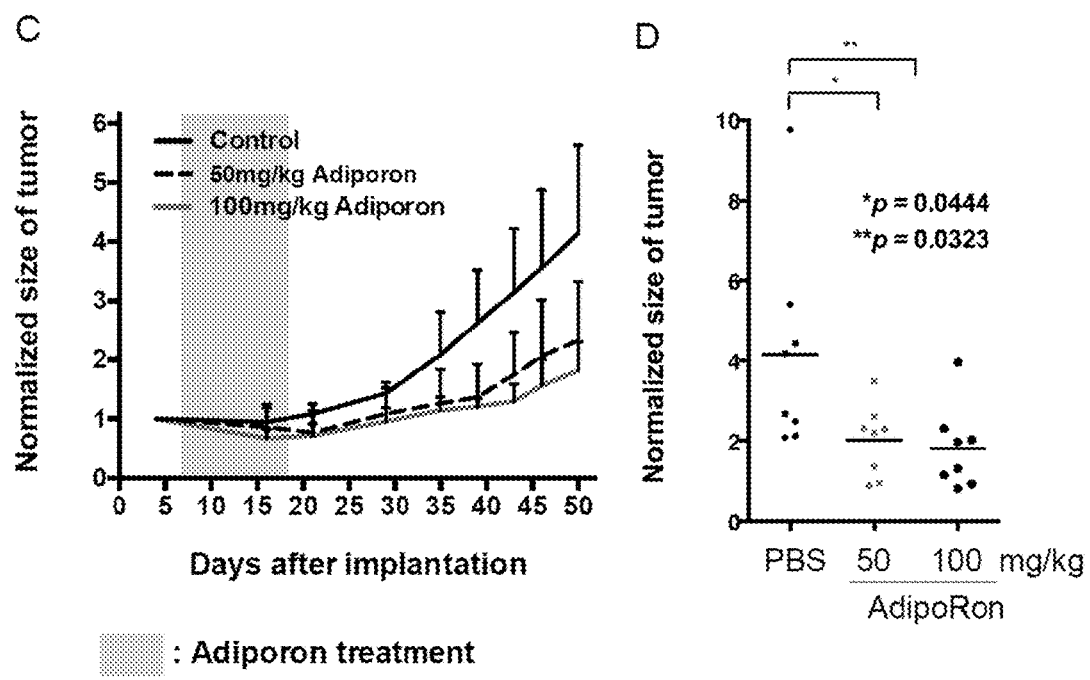

FIG. 14. Treatment of triple-negative breast cancer by AdipoRon. A) Flow chart of the animal experiment in FIGS. 7G and H. B) Representative tumors from each group of mice of the animal experiment in FIGS. 7G and H are shown. C, D) $4 \times 10^6$ of LM2 cells were inoculated into the fat pad of nude mice. 12 days after injection, when the tumor reached to 100 mm³, mice were randomly divided into two groups. They were treated with either PBS or AdipoRon (50 mg/kg and 100 mg/kg, respectively) for 10 times, and the tumor size was monitored. Tumor growth was measured two weeks after inoculation (n=8). Student's t test was used for statistical analysis. **P<0.01; *P<0.05.

DETAILED DESCRIPTION

The present invention is described herein using several definitions, as set forth below and throughout the application.

Definitions

Unless otherwise specified or indicated by context, the terms "a", "an", and "the" mean "one or more." For example, "an agonist" should be interpreted to mean "one or more agonists."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment, for example, treatment by include administering a therapeutic amount of one or more therapeutic agents that are agonists of an adiponectin receptor (e.g. adiponectin receptor 1) and/or that inhibit activity or expression of one or more members of Set1B/COMPASS.

A "subject in need of treatment" may include a subject having a disease, disorder, or condition that is responsive to an agonist of an adiponectin receptor. A "subject in need of treatment" may include a subject having a disease, disorder, or condition that is responsive to an agent that inhibits the expression and/or activity of one or more members of Set1B/COMPASS. For example, a "subject in need of treatment" may include a subject having a cell proliferative disease, disorder, or condition such as cancer. Cancers may include, but are not limited to adenocarcinoma, leukemia, lymphoma, melanoma, myeloma, sarcoma, and teratocarcinoma and particularly cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

A "patient in need of treatment" may include a patient having a Set1B/COMPASS-associated cancer that is characterized by expression (or overexpression) of Set1B/COMPASS, which may include but are not limited to adenocarcinoma, lymphoma, melanoma, myeloma, sarcoma, and teratocarcinoma. A subject in need thereof may include a patient having cancer of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

Formulations and Administration

The formula of the compounds disclosed herein should be interpreted as encompassing all possible stereoisomers, enantiomers, or epimers of the compounds unless the formulae indicates a specific stereoisomer, enantiomer, or epimer. The formulae of the compounds disclosed herein should be interpreted as encompassing salts, esters, amides, or solvates thereof of the compounds (e.g., pharmaceutically acceptable salts).

The disclosed therapeutic agents may be effective in inhibiting cell proliferation of cancer cells, including mixed lineage leukemia cells. Cell proliferation and inhibition thereof by the presently disclosed therapeutic agents may be assessed by cell viability methods disclosed in the art including colorimetric assays that utilize dyes such as MTT, XTT, and MTS to assess cell viability. Preferably, the disclosed therapeutic agents have an $IC_{50}$ of less than about 10 µM, 5 µM, 1 µM, or 0.5 µM in the selected assay.

The therapeutic agents utilized in the methods disclosed herein may be formulated as pharmaceutical compositions that include: (a) a therapeutically effective amount of one or more of the therapeutic agents as disclosed herein; and (b) one or more pharmaceutically acceptable carriers, excipients, or diluents. The pharmaceutical composition may include the therapeutic agent in a range of about 0.1 to 2000 mg (preferably about 0.5 to 500 mg, and more preferably about 1 to 100 mg). The pharmaceutical composition may be administered to provide the therapeutic agent at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the therapeutic agent at the site of action is about 2 to 10 µM.

The therapeutic agents utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The therapeutic agents utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The therapeutic agents utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The therapeutic agents utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The therapeutic agents utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the therapeutic agents may be adapted for administration by any appropriate route, for example by the oral (including buccal or sublingual), or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Therapeutic Targeting of SET1B/COMPASS Pathway for Treating Cancers

Disclosed are methods for treating Set1B/COMPASS-associated cancers that are characterized by expression or overexpression or activity of Set1B/COMPASS. The methods typically include administering to the patient a therapeutic amount of an inhibitor of Set1B/COMPASS and/or administering an agonist for a target that is negatively regulated by Set1B/COMPASS. Cancer that are treated by the disclosed methods may include breast cancers, such as ER-negative breast cancer, HER2-negative breast cancer, PR-negative breast cancer, or triple negative breast cancer (TNBC).

The disclosed methods typically include administering to the patient a therapeutic amount of an inhibitor of Set1B/COMPASS pathway and/or an agonist for a target that is negatively regulated by Set1B/COMPASS. In particular, the disclosed methods may include administering to the patient an agonist of an adiponectin receptor to the patient, such as an agonist of adiponectin receptor 1. Suitable agonists may include but are not limited to a compound having a formula:

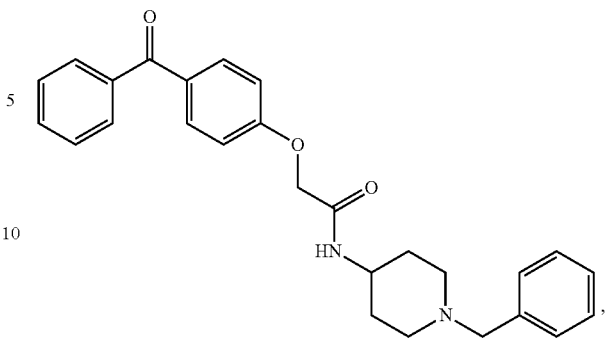

which is otherwise referred to as "adiporon." (See Okada-Iwabu et al., "A small-molecule AdipoR agonist for type 2 diabetes and short life in obesity," Nature 493 (503), Nov. 28, 2013, the content of which is incorporated herein by reference in its entirety). The disclosed methods may include administering other agents which may function as agonists for the adiponectin receptor 1. These other agents may include, but are not limited to peptide mimetics of adiponectin (see, e.g., U.S. Published Application No. 20140057833; Otvos et al. 2014, Frontiers in Chemistry, Vol. 2, Article 93: 1-15; and Ma et al., 2017, J. Enzyme Inhib and Medicinal Chem, Vol. 32, No. 1: 624-631); matairesinol, arctiin, (−)-arctigenin, gramine (see Sun et al. PLoS One, 2013, 8(5): e63354); and/or 6-C-beta-D-glcypyranosyl-(2S,3S)-(+)-5,7,3',4'-tetrahydroxydihydroflavonol (GTDF) (Singh et al., Mol. Cell Endocrinol. 2017 Jan. 5; 439:273-285); the contents of which are incorporated by reference herein in their entireties.

The disclosed methods may include administering to a subject in need thereof RNA interference (RNAi) therapy. For example, the disclosed methods may include administering to a subject in need thereof an interfering RNA and/or a vector that expresses an interfering RNA, wherein the interfering RNA inhibits expression of Set1B/COMPASS, optionally wherein the interfering RNA is a small hairpin RNA (shRNA) or a small interfering RNA (siRNA) that inhibits expression of Set1B and/or Bod1. Methods for administering RNAi therapy, for example, via administering a vector that expresses RNAi, are known in the art. (See, e.g., Mansoori et al., Adv. Pharm. Bull. 2014 December; 4(4):313-321; Angaji et al., J Genet. 2010 December; 89(4): 527-37; Wittrup et al., Nature Reviews Genetics 16, 543-552 (2015); Bobbin et al., Annual Revie of Pharma. and Toxic., Vol 56, 2016; 103-122; and Tatiparti et al., Nanomaterials, 5 Apr. 2017; 7, 77, nano7040077); the contents of which are incorporated by reference herein in their entireties.

Also disclosed are diagnostic/treatment methods that include identifying a cancer patient that has one or more mutations in a gene of the Set1/COMPASS pathway and/or identifying a cancer patient that is overexpressing Set1/COMPASS, and subsequently administering to the patient a therapeutic amount of an agonist and/or an inhibitor of the Set1B/COMPASS pathway to the patient identified as having one or more mutations in Set1/COMPASS and/or identified as expressing or overexpressing Set1/COMPASS. Mutations may be identified, for example, by obtaining a genomic DNA sample from the patient and treating the genomic DNA sample with reagents to identify one or more mutations in Set1/COMPASS (e.g., by sequencing the genomic DNA sample and/or by probing the genomic DNA sample, and optionally including amplifying the genomic DNA sample). Expression or overexpression may be identified by obtaining a biological sample from the patient and measuring Set1/COMPASS in the biological sample relative to a control sample (e.g., a sample from a normal patient).

Therapeutic agents administered in the disclosed diagnostic/treatment methods may include an inhibitor of Set1B/COMPASS and/or an agonist for a target that is negatively regulated by Set1B/COMPASS. The therapeutic agents may include, but are not limited to, small molecule agonists/inhibitors, peptide agonists/inhibitors, and/or nucleic acid molecules. Agonists and inhibitors may include small molecule agonists and/or inhibitors (e.g., which may be nonprotein agonists and/or inhibitors such as adiporon or derivative thereof) and also may include proteinaceous agonists and/or inhibitors.

Specifically contemplated herein is the use of agonists of the adiponectin receptor 1 (adipoR1 agonists) to treat triple negative breast cancer. In addition to adipoR1 agonists, other agents that can inhibit the Set1B/BOD1 pathway may be administered for treating triple negative breast cancer.

ILLUSTRATIVE EMBODIMENTS

The following embodiments are illustrative and are not intended to limit the scope of the claimed subject matter.

Embodiment 1

A method for treating a cancer characterized by expression or overexpression of Set1B/COMPASS in a subject in need thereof, the method comprising administering to the subject a therapeutic amount of an inhibitor of Set1B/COMPASS and/or administering an agonist of a target that is negatively regulated by Set1B/COMPASS.

Embodiment 2

The method of embodiment 1, wherein the cancer is breast cancer.

Embodiment 3

The method of embodiment 1 or 2, wherein the cancer is ER-negative breast cancer.

Embodiment 4

The method of any of the foregoing embodiments, wherein the cancer is HERB2-negative breast cancer.

Embodiment 5

The method of any of the foregoing embodiments, wherein the cancer is PR-negative breast cancer.

Embodiment 6

The method of any of the foregoing embodiments, wherein the cancer is triple negative breast cancer (TNBC).

Embodiment 7

The method of any of the foregoing embodiments comprising administering an agonist of an adiponectin receptor to the subject, optionally administering an agonist of adiponectin receptor 1 to the subject.

Embodiment 8

The method of any of the foregoing embodiments comprising administering to the subject a compound having a formula:

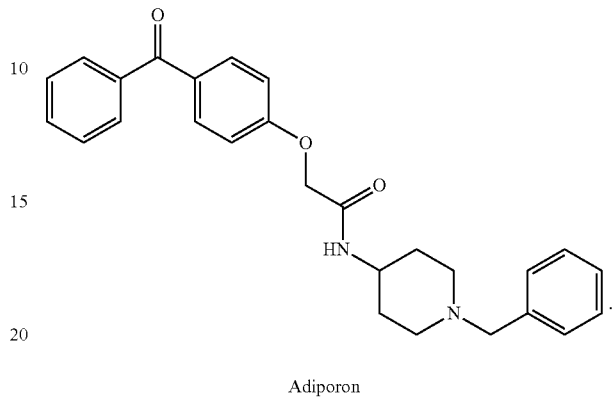

Adiporon

Embodiment 9

The method of any of the foregoing embodiments comprising administering to the subject a peptide mimetic of adiponectin, matairesinol, arctiin, (−)-arctigenin, gramine, and/or 6-C-beta-D-glcypyranosyl-(2S,3S)-(+)-5,7,3',4'-tetrahydroxydihydroflavonol (GTDF).

Embodiment 10

The method of any of the foregoing embodiments, comprising administering to the subject an RNA interference (RNAi) therapy, for example, by administering an interfering RNA and/or a vector that expresses an interfering RNA, wherein the interfering RNA inhibits expression of Set1B/COMPASS, optionally wherein the interfering RNA is a small hairpin RNA (shRNA) or a small interfering RNA (siRNA) that inhibits expression of Set1B and/or Bod1.

Embodiment 11

A method comprising identifying a cancer subject that has one or more mutations in a gene of the Set1/COMPASS pathway and/or identifying a cancer subject that is overexpressing Set1/COMPASS, and administering a therapeutic amount of an agonist and/or an inhibitor of the Set1B/COMPASS pathway to the subject identified as having one or more mutations in Set1/COMPASS and/or identified as overexpressing Set1/COMPASS.

Embodiment 12

The method of embodiment 11, wherein the subject has breast cancer.

Embodiment 13

The method of embodiment 11 or 12, wherein the subject has ER-negative breast cancer.

Embodiment 14

The method of any of embodiments 11-13, wherein the subject has HERB2-negative breast cancer.

Embodiment 15

The method of any of embodiments 11-14, wherein the subject has PR-negative breast cancer.

Embodiment 16

The method of any of embodiments 11-15, wherein the subject has triple negative breast cancer.

Embodiment 17

The method of any of embodiments 11-16 comprising administering an agonist of an adiponectin receptor to the subject, optionally administering an agonist of adiponectin receptor 1 to the subject.

Embodiment 18

The method of any of embodiments 11-17 comprising administering to the subject a compound having a formula:

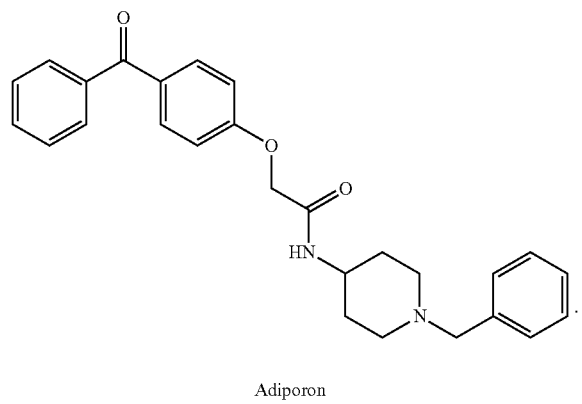 [SMILES: O=C(COc1ccc(C(=O)c2ccccc2)cc1)NC1CCN(Cc2ccccc2)CC1]

Adiporon

Embodiment 19

The method of any of embodiments 11-18 comprising administering to the subject a peptide mimetic of adiponectin, matairesinol, arctiin, (−)-arctigenin, gramine, and/or 6-C-beta-D-glcypyranosyl-(2S,3S)-(+)-5,7,3',4'-tetrahydroxydihydroflavonol (GTDF).

Embodiment 20

The method of any of embodiments 11-19, comprising administering to the subject an RNA interference (RNAi) therapy, for example, by administering an interfering RNA and/or a vector that expresses an interfering RNA, wherein the interfering RNA inhibits expression of Set1B/COMPASS, optionally wherein the interfering RNA is a small hairpin RNA (shRNA) or a small interfering RNA (siRNA) that inhibits expression of Set1B and/or Bod1.

EXAMPLES

The following Examples are illustrative and are not intended to limit the scope of the claimed subject matter.

Title: Therapeutic Targeting of SET1B/COMPASS Pathway in Treating Triple-Negative Breast Cancer Abstract Mutations and translocations within COMPASS (Complex Proteins Associated with Set1) family of histone lysine methyltransferases are associated with a large number of human diseases including cancer. We have demonstrated that the depletion of SET1B selectively inhibits multiple triple negative breast cancer (TNBC) cell survival in vitro and in vivo but does not affect ER-positive or normal epithelia cell growth. Surprisingly, in TNBC, SET1B/COMPASS regulates a specific gene expression profile without altering histone H3K4 methylation. We further identified that SET1B as the only cytoplasmic form of COMPASS family, with BOD1 as its unique cytoplasmic subunit interacting with the N-terminus of SET1B. Furthermore, we demonstrated that that loss of SET1B or the SET1B/BOD1 interaction induces activation of ADIPOR1 signaling pathway, which is inactivated in both obesity and during TNBC development. Finally, we found that a small molecular agonist for the SET1B/COMPASS target, the Adiponectin receptor 1, can dramatically inhibit TNBC growth in vitro and in vivo. Collectively, our results elucidate a new function for SET1B/COMPASS in the cytoplasm, which can be harnessed for a therapeutic strategy regulating signaling in human breast cancer.

INTRODUCTION

Misregulation of histones modifiers has emerged as a common therapeutic target for the treatment of human cancer (Piunti and Shilatifard, 2016). Although the physiological importance of protein lysine methylation remained obscure for many years, several protein lysine methyltransferases (KMTs), as well as lysine demethylases (KDMs) have now been identified, and their physiological significance during development and disease pathogenesis, particularly in the field of epigenetics has begun to be elucidated. Molecular perturbation of KMTs and KDMs have been demonstrated as a common mechanism during tumorigenesis (Hamamoto et al., 2004; Kotake et al., 2007; Mazur et al., 2014). Thus, both KMTs and KDMs are considered to be therapeutic targets in different human cancers (Ferguson et al., 2011; Klaus et al., 2014; Kubicek et al., 2007).

All known KMTs that associate with chromatin contain a SET domain, with the exception of Dot1, which harbors a unique catalytic domain. Based on the primary amino acid sequence architecture and substrate specificity, KMTs can be divided into six subfamilies KMT1-6 (Mohan et al., 2012). SET1A, SET1B and MLL1-4 belong to the KMT2 family, which mono-, di- and trimethylate histone H3K4, and they are considered to be involved in positive regulation of gene transcription (Kouzarides, 2007; Mohan et al., 2012; Shilatifard, 2012). This family of enzymes was first biochemically isolated initially from yeast within a macromolecular complex and named COMPASS (Complex Proteins Associated with Set1)(Krogan et al., 2002; Miller et al., 2001; Shilatifard, 2012). COMPASS was demonstrated to be highly conserved from yeast to human with one COMPASS family member in yeast and the six KMT2/COMPASS members in mammals (Piunti and Shilatifard, 2016; Shilatifard, 2012). MLL1- and MLL2/COMPASS contain the tumor suppressor factor Menin within their complexes, while MLL3 and MLL4/COMPASS are associated with PTIP, PA1, NCOA6 and UTX (Cho et al., 2007; Shilatifard, 2012). Interestingly, SET1A and SET1B are more similar to yeast SET1-COMPASS, and all of the yeast components have corresponding mammalian counterparts (Wu et al., 2008). Although both SET1A and SET1B share the same subunit composition, global reduction of 1-13K4 methylation levels is observed only in SET1A but not SEM knockout ESCs (embryonic stem cells) and embryos. Overexpression of SET1B fails to rescue the ESC proliferation defects induced by the loss of SET1A, suggesting that SET1B may have a distinct function from its homolog SET1A (Bledau et al., 2014). SET1A/COMPASS has been shown to regulate wnt target genes and to control tumor growth of colorectal cancer cells (Salz et al., 2014). However, the function of SET1B in human cancer remains unclear.

Breast cancer is the leading type of cancer among women in the United States. According to the 2015 annual report by the American Cancer Society, one out of eight women will develop breast cancer in their lifetime. About 15%-20% of breast cancers are characterized as triple negative breast cancer (TNBC) since they lack the expression of estrogen receptor, progesterone receptor and epidermal growth factor receptor-2/neu (Bauer et al., 2007; Dent et al., 2007). As measured by gene expression profiling, the majority of TNBC have a basal-like molecular phenotype. Management of this subtype of breast cancer is a challenge to the clinicians because of its aggressive features, poor outcome, and lack of therapeutic targets (Rouzier et al., 2005). In this study, we sought to investigate the role of COMPASS family in breast cancer, and translate the results into possible therapeutic strategy that could be harnessed for TNBC treatment. Here, we report that a cytoplasmic form of COMPASS family found within SET1B/COMPASS promotes TNBC growth and that a small molecule agonist for a SET1B/COMPASS-repressed target gene can inhibit TNBC growth in vitro and in vivo. These studies identify targeting SET1B/COMPASS pathway as a novel therapeutic strategy for human breast cancer therapy.

Results

SET1B/COMPASS is Essential for Human Breast Cancer Cell Survival.

Figure 1:
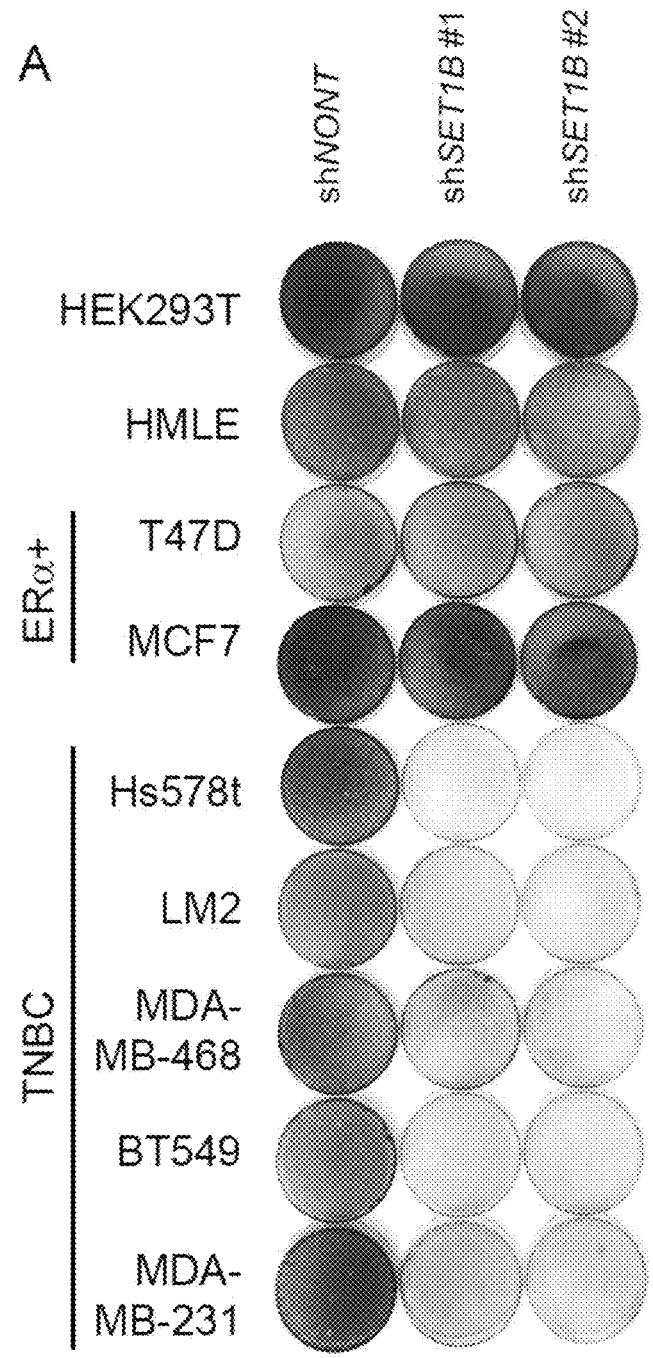
FIG. 1. SET1B/COMPASS is essential for human breast cancer cell survival. A) HEK293, ERα positive cell line MCF7, and T47D, human normal epithelia cell line HMLE, and five triple-negative breast cancer cell lines LM2, Hs578t, BT549, MDA-MB-468, and MDA-MB-231 cells were infected with lentiviruses expressing two distinct SET1B shRNAs (shSET1B#1 and shSET1B#2). Non-targeting shRNA (shNONT) was used as a control. After puromycin selection for 48 hours, $4 \times 10^4$ living cells were seeded in 6-well plates and grown for one week before crystal violet staining. B) Quantification of crystal violet staining was determined as described in materials section. n=4, Student's t test was used for statistical analysis.
Figure 1:
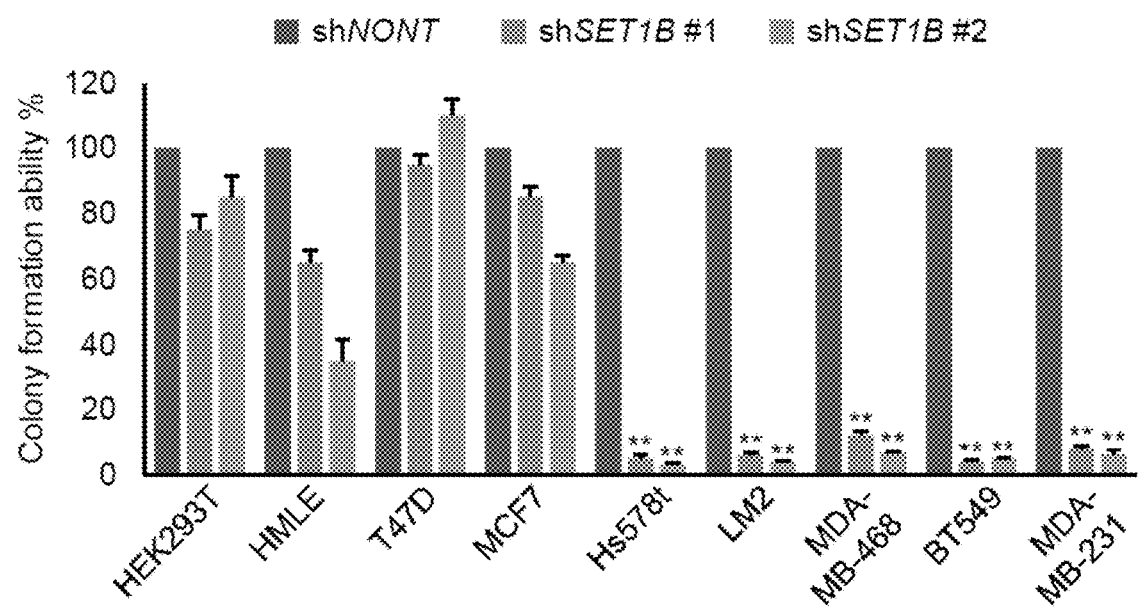
Figure 1:
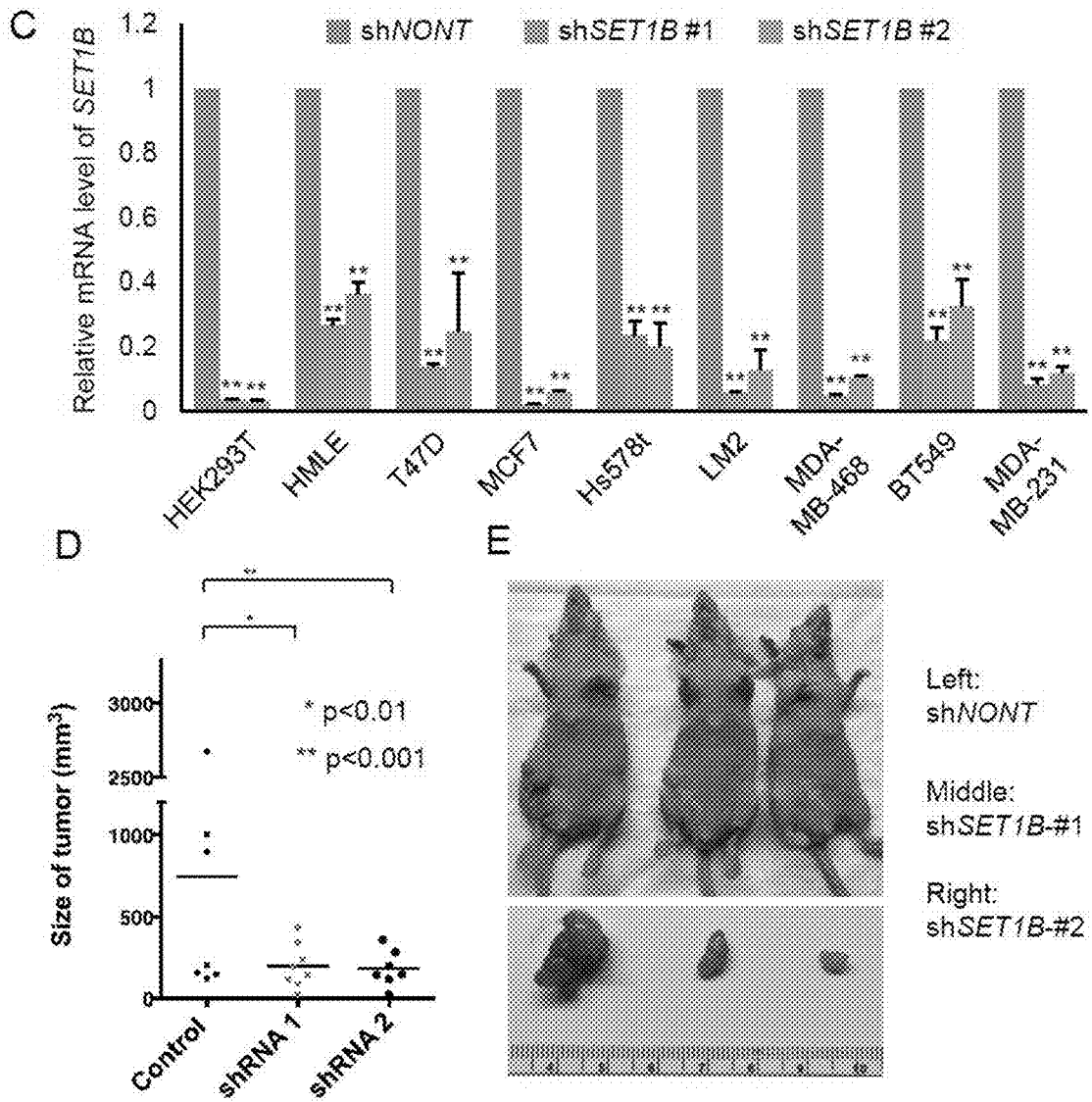
Figure 1:
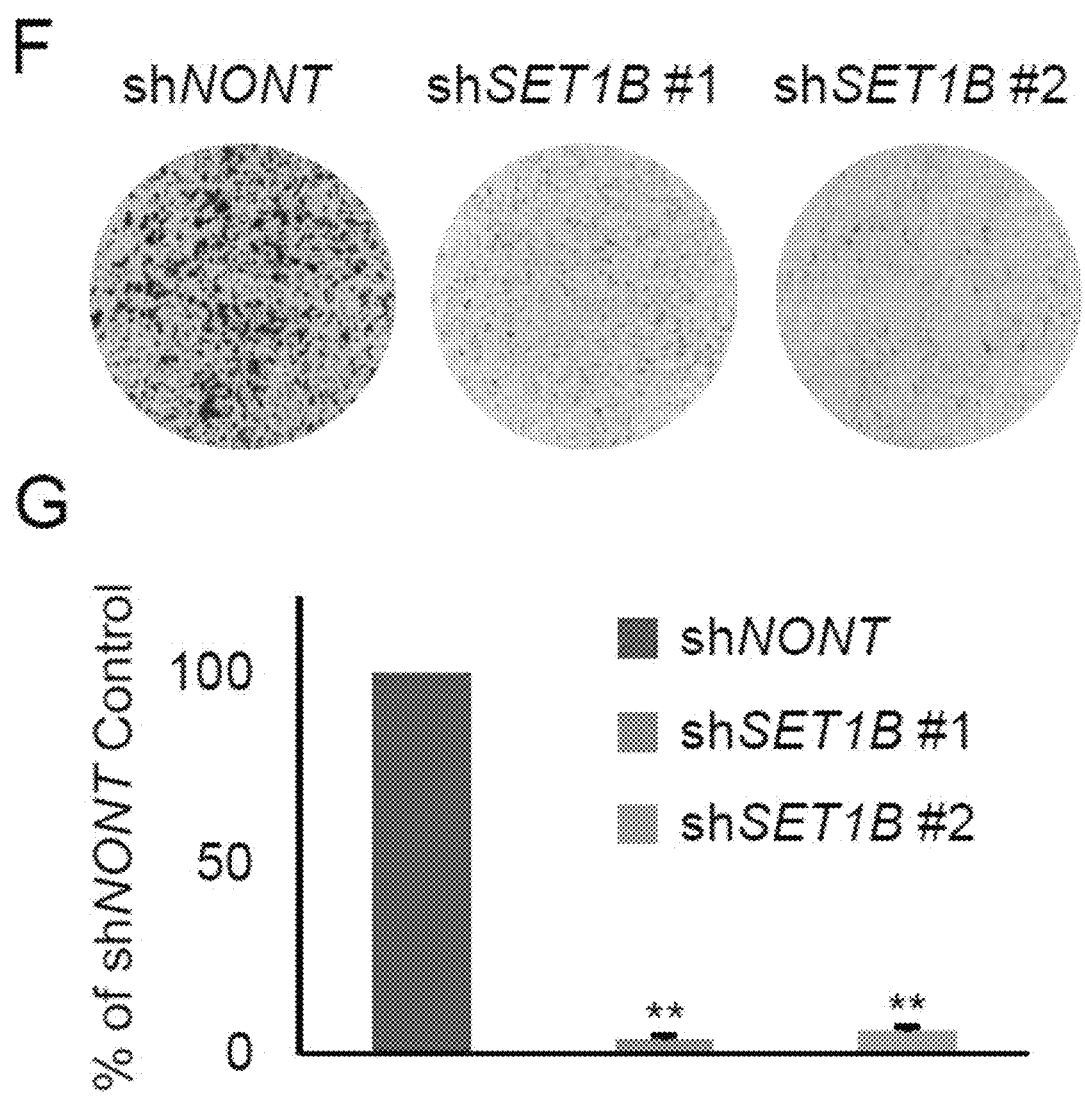

The COMPASS family in human is comprised of the SET1A, SET1B, MLL1, MLL2, MLL3, and MLL4 complexes (Mohan et al., 2012; Shilatifard, 2012). The cancer genome sequencing studies have revealed that MLL3, MLL4, and UTX components of the MLL3/MLL4-COMPASS family are highly mutated in different forms of cancers including both hematological malignancies and solid tumors (Herz et al., 2014; Kandoth et al., 2013). However, the functions of SET1A/B in human cancer remains unclear. To further explore the relationship between human breast cancer and the SET1A/B COMPASS family of methyltransferases, we knocked down either SET1A or SET1B in multiple human breast cancer cell lines. In FIG. 1A, we demonstrate the result of knocked down SET1B levels in cellular growth in multiple cell lines including: HEK293T cells; HMLE cells; estrogen receptor positive cell lines, MCF7 and T47D; and triple-negative cell lines Hs578t, LM2, MDA-MB-468, BT549, and MDA-MB-231. To exclude off-target effect of our shRNAs, we used two independent shRNA constructs for SET1B depletion. Interestingly, we found all five triple-negative breast cancer lines show remarkable sensitivity to SET1B depletion, while loss of SET1B has very little effect on cell growth for HEK293T and normal epithelial cells, or for ER-positive breast cancer cell lines (FIG. 1A). The quantified colony formation ability is shown in FIG. 1B. The knocking down efficiency was validated by real-time PCR (FIG. 1C). To determine that the effects observed are specific to SET1B, we also knocked down SET1A levels in five of the cell lines and assessed cell survival (FIG. 8). After confirming the knockdown efficiency of SET1A shRNA by Western blot (FIG. 8A), we found that a reduction in SET1A levels does not significantly alter cell survival as compared to the result of SET1B knockdown (compare FIG. 1A to FIG. 8B). As expected, the loss of SET1A does not significantly alter the bulk levels of histone H3K4me3 (FIG. 8C). To determine if the loss of SET1B also affects cell growth in vivo, we injected LM2 cells, which were transfected with non-targeting or SET1B shRNA, into the fat pad of nude mice. Consistent with what we observed in vitro, the reduction in SET1B protein significantly reduced tumor growth in animals (FIG. 1D, E). Moreover, depletion of SET1B also altered cell migration ability (FIG. 1F, G). These findings together suggest that SET1B/COMPASS is a potential biomarker and might function as an oncogene of human breast cancer. To validate whether the SET1B expression level increases during breast cancer malignant transformation, we compared SET1B protein levels between the mammary epithelial cell line HMLE and its malignant transformed clones, NAMEC3-11. As shown in FIG. 8D, the protein levels for SET1B are considerably increased in all of the NAMEC cell lines compared to extracts obtained from the normal epithelial cells. As a control, we also tested the expression levels of some other common COMPASS subunits, such as ASH2L and RBBP5, and did not observe any major changes in their protein levels (FIG. 8D). Based on these findings, we postulated that SET1B could play a role in breast cancer development and survival, which required further investigations.

Histone H3K4 Methylation-Independent Function of SET1B in the Regulation of Gene Expression.

In order to investigate the mechanistic role of SET1B/COMPASS and its contributions to breast cancer growth and survival, we knocked down SET1B with two individual shRNAs in triple-negative breast cancer line MDA-MB-231, and further performed RNA-seq analysis with the resulting cells. The two independent SET1B shRNAs affected the expression of 626 and 363 genes individually, while they co-affected the expression of 147 genes (FIG. 2A). The metascape pathway analysis reveals that most of the SET1B-regulated genes are involved in molecular mechanisms of cancer and cell cycle control (FIG. 2B), which suggests a potential function for SET1B in cellular growth. Interestingly, we noticed that the knocking down of SET1B resulted in up-regulation of some genes that suppress cell growth such as ZNF367, TMBIM16, and CASP3; while Set1B-dependent down-regulated genes promote cell growth such as ELK3, FOXQ1, and CCNJ (FIG. 9A). The mRNA level of FOXQ1 and TMBIM6 in shNONT and shSET1B cells was further validated by real-time PCR (FIG. 9B). Indeed, knocking down either ELK3, FOXQ1, or CCNJ affected the colony formation ability of MDA-MB-231 cells (FIG. 9C, D), similar to what we observe with SET1B shRNA (FIG. 1C), indicating that SET1B might function at least partially through the regulation of the expression of these oncogenes.

In vitro studies with SET1B/COMPASS suggested that this complex functions similar to its yeast homologue Set1/COMPASS and is capable of mono-, di-, and trimethylating histone H3K4 (Shilatifard, 2012). To test if the loss of SET1B in vivo also affects global histone H3K4 trimethylation on chromatin, we performed ChIP-seq analysis with anti-H3K4me1 and anti-H3K4me3 in MDA-MB-231 shCtrl and MDA-MB-231 shSET1B cells. Surprisingly, neither H3K4me1 nor H3K4me3 was significantly altered after knocking down SET1B (FIG. 2C, D). Representative H3K4me1 and H3K4me3 tracks at FOXQ1 and ZNF367 gene loci are shown in FIG. 2E. Surprisingly, neither knocking down nor over-expression of SET1B altered bulk histone H3K4 mono-, di-, and trimethylation levels in ER-positive MCF7 cells (FIG. 9E). We also knocked down SET1B in four other triple-negative breast cancer cell lines, and did not observe significant changes in bulk histone H3K4 methylation levels (FIG. 9F). Our findings suggest that SET1B/COMPASS may have histone methylation-independent function in these cells that needs to be further explored.

A Cytoplasmic COMPASS!

Since knocking down or overexpressing SET1B did not significantly altere histone H3K4 methylation patterns in bulk or on chromatin, we tested the subcellular localization of SET1B with antibodies that we have generated towards this COMPASS family member. To determine the specificity of the antibodies, we first tested the COMPASS specific antibodies by performing immunofluorescence (IF) in HeLa cells transfected with non-targeting shRNA or SET1B shRNA. Surprisingly, we found that in HeLa cells, most of the SET1B staining is localized in the cytoplasm, while SET1A is consistently localized in the nucleus (FIG. 3A, FIG. 10A). In order to exclude that there may be some mutations of the SET1B gene in HeLa cells that lead to its mislocalization to the cytoplasm, we transfected a Flag-tagged full-length SET1B plasmid into HEK293T cells, and performed immunofluorescence with anti-Flag (FIG. 10B). Consistent with the IF experiments in HeLa cells, we found the majority of the IF signal to be localized in the cytoplasm. We further confirmed SET1B localization by performing IF staining in four triple-negative breast cancer cell lines, LM2, MDA-MB-231, BT549, and Hs578t. As shown in FIG. 3B, the majority of SET1B protein in these cells is also detected in the cytoplasm. Moreover, the cellular localization of SET1B does not change in human normal epithelial cells nor in the ER-positive cell line MCF7 (FIG. 10C, D). In order to biochemically investigate the SET1B/COMPASS localization pattern in these cells, we purified Flag-RBBP5, which is a common subunit of all COMPASS family, from both cytoplasmic and nuclear extracts (FIG. 3C). Mass spectrometric analysis with the purified material confirmed our cytological data that majority of SET1B/COMPASS is found within the cytoplasmic fraction (FIG. 3D, E). Western blot analysis further confirms our mass spectrometry data by showing that SET1B is mostly confined to the cytoplasm in these cells (FIG. 3F).

In order to investigate whether cytoplasmic SET1B can function within COMPASS as a lysine methyltransferase, we immunoprecipitated members of the COMPASS family from cytoplasmic and nuclear extracts and analyzed their endogenous interactions with SET1B. As shown in FIG. 3G, the cytoplasmic SET1B stably interacts with the WARD complex, which is responsible for COMPASS catalytic activity (Shilatifard 2012), while MLL3 only forms a complex with the WARD complex in the nucleus. Overexpressing SET1B in MCF7 and HeLa cells resulted in sequestration of WARD components in the cytoplasm, which further leads to the reduced SET1A protein in the nucleus (FIG. 10E). This finding is in agreement with the COMPASS stability studies we performed in yeast, where in the absence of WARD, Set1 also becomes very unstable in yeast cells. Our findings suggest that SET1B/COMPASS is predominantly cytoplasmic and SET1A/COMPASS is predominantly nuclear in mammalian cells.

BOD1, the Cytoplasmic-Specific Subunit of SET1B/COMPASS.

In order to fully characterize the interactome of SET1B/COMPASS in triple-negative breast cancer cells and apply this information for the identification of their molecular targets, we infected MDA-MB-231 cells with retrovirus expressing Flag-tagged human full-length SET1B cDNA. After G418 selection, we obtained pooled clones of MDA-MB-231 cells stably expressing full-length SET1B. The Flag-tagged SET1B was then purified from either cytoplasmic or nuclear extracts (FIG. 4A). Silver staining of the purified complexes demonstrated that more SET1B is purified from cytoplasmic extracts of MDA-MB-231-Flag-SET1B expressing cells. Using mass spectrometric methods, we found that SET1B forms a COMPASS-like complex in both the cytoplasm and nucleus, having all of the core COMPASS subunits (FIG. 4B). However, we found that BOD1 protein, which is homologous to Cps15 subunit of yeast COMPASS, is largely enriched in the cytoplasmic purification of SET1B/COMPASS (FIG. 4C). Consistently, BOD1 was also found in the cytoplasmic immunoprecipitates of Flag-RBBP5 (FIG. 11A). RBM15, as well as its homologous RBM15B, were also found enriched in the nuclear SET1B complex (FIG. 4B), which is consistent with previous studies (Lee and Skalnik, 2012). We performed additional western blot analysis to confirm the distribution of BOD1 and RBM15 in both cytoplasmic- and nuclear-purified SET1B/COMPASS. As shown in FIG. 11C, ASH2L is detected in both cytoplasmic and nuclear SET1B/COMPASS. However, RBM15/RBM15B, which contain NLS in their C-termini, could only be detected with nuclear SET1B purifications. We further performed immunoprecipitation to confirm the interaction between endogenous SET1B and BOD1 protein (FIG. 4D). We also generated stable cells expressing ectopic BOD1, and purified Flag-tagged BOD1 protein from the cytoplasm (FIG. 4E). As shown in FIG. 4F, G, the entire SET1B/COMPASS was identified by mass spectrometry as top interacting proteins in this purification. Based on these observations, we conclude that the majority of SET1B/COMPASS is found with BOD1 in the cytoplasm, while SET1A/COMPASS is associated with BOD1L in the nucleus (FIG. 11B, D).

In order to investigate whether BOD1 contributes to SET1B's oncogenic function in TNBC, we knocked down BOD1 with two individual shRNAs in MDA-MB-231 cells. We found that the knockdown of BOD1 affects the protein level of SET1B (FIG. 4H). Accordingly, similar to SET1B depletion, loss of BOD1 also decreases cell growth (FIG. 4I) as well as changes in cell morphology (FIG. 4J). These results suggest that BOD1 functions with SET1B in cells. We also mapped the interaction region between BOD1 and SET1B and found that BOD1 interacts with the N-terminus of SET1B, consistent with the mapped interaction between Cps15 and Set1 in yeast (FIG. 11F, G) (Takahashi et al., 2011).

Set1B/COMPASS Containing BOD1 and the ADIPOR1 Signaling.

In order to identify common downstream targets of BOD1 and SET1B in growth and the malignant state of triple-negative breast cancer cells, we performed RNA-seq analyses in MDA-MB-231 infected with a lenti-virus expressing either non-targeting shRNA or two individual BOD1 or SET1B shRNAs. As shown in FIG. 5A, and similar to SET1B, BOD1 mainly functions through suppressing gene expression in cells. Strikingly, nearly half of the genes that are regulated by SET1B are also regulated by BOD1 (FIG. 5A). By Metascape pathway analysis (Tripathi et al., 2015), we found that Pathway in Cancer is the most enriched pathway for genes that are co-regulated by BOD1 and SET1B (FIG. 5B). By comparing the gene expression profile between BOD1 and SET1B shRNAs, we noticed that the knocking down of either SET1B or BOD1 significantly increases the expression of genes involved in adiponectin signaling pathway, such as ADIPOR1, PRKAR2A, and COX7C (FIG. 5C). Adiponectin, which is secreted by fat tissue, directly interacts with adiponectin receptor 1 (ADIPOR1) or 2 (ADIPOR2) and further stimulates the phosphorylation of AMPK through recruiting APPL1 to the cell membrane. PPARGC1A is subsequently stimulated by pAMPK and translocates into the nucleus and transcribes a subset of mitochondria biogenesis genes such as COX7C (Bremer et al., 2015). As far as we know, adiponectin signaling, which is considered to be a tumor suppressive, is inactivated in breast cancer patients (Pfeiler et al., 2010). We hypothesized that AdipoR1 signaling may be involved in SET1B-mediated function in triple-negative breast cancer cells. As shown in FIG. 5D, in MDA-MB-231 cells, SET1B/BOD1 only suppresses the gene expression of adiponectin receptor 1, but not adiponectin receptor 2. This result is further confirmed by real-time PCR (FIG. 5E) and western blot (FIG. 5F). To test if the ADIPOR1 signaling suppressed by SET1B/COMPASS is universal in triple-negative breast cancers, we knocked down SET1B and BOD1 in four different triple-negative breast cancer lines and detected changes in the gene expression of Adipor1. As shown in FIG. 5G, the gene expression of ADIPOR1 is significantly increased in all cell lines after knocking down either SET1B or BOD1 subunits of SET1B/COMPASS. In order to explore the potential mechanism of how SET1B/BOD1 regulates AdipoR1 expression level, we treated the MDA-MB-231-shNONT and MDA-MB-231-shSET1B with Actinomycin D, which blocks the mRNA synthesis. As shown in FIG. 5H, the AdipoR1 mRNA level in cells with SET1B depletion is more stable than cells transfected with non-targeting shRNA. This result indicated that the cytoplasmic SET1B/COMPASS may play an essential role in the regulation of mRNA metabolism and stability. Because ER-positive cell lines are not sensitive to the loss of SET1B protein levels, we asked whether SET1B shRNA also affects ADIPOR1 ER-positive cells. We compared the RNA-seq profile between SET1B stably knocked down and over-expressed MCF7 cells. We identified 1261 genes that are positively regulated by SET1B and 1394 genes that are negatively regulated by SET1B shRNA in MCF7 cells (FIG. 12A, B). Interestingly, there are 19 genes that are negatively regulated by SET1B shRNA in both MCF7 and MDA-MB-231 cells, which include ADIPOR1 signaling genes such as ADIPOR1, PRKAR2A, and COX7 (FIG. 12B). These results suggested that the regulation of ADIPOR1 signaling by the SET1B/BOD1 COMPASS is shared by both ER-positive and triple-negative breast cancer cells. Consistent with what we concluded in FIG. 2, that neither histone H3K4me1 nor H3K4me3 is affected after knocking down SET1B in cells (FIG. 12C). In order to further clarify whether SET1B controls AdipoR1 gene expression in catalytic activity dependent or independent manner, we knocked out the catalytic domain (SET domain) of SET1B gene by CRISPR-Cas9 (FIG. 12D). We performed PCR and western blot to confirm that the SET1 domain of SET1B is completely knocked out from MDA-MB-231 cells (FIG. 12E), while the protein level of SET1B was not affected by SET-domain deletion (FIG. 12F). The RNA-seq result demonstrated that the SET domain is successfully knocked out by CRISPR (FIG. 12G, upper panel, marked by red arrow), and strikingly, the mRNA level of AdipoR1 does not significantly change in the SET-domain deleted cells (FIG. 5G, lower panel). Cell growth assay revealed that loss of SET-domain of SET1B does not affect cell growth (FIG. 12H). Taken together, this result proved that AdipoR1 is a main downstream effector of SET1B, which is controlled by SET1B catalytic activity independent function.

Set1B/COMPASS Regulated ADIPOR1 Signaling Pathway as a Therapeutic Target in Triple-Negative Breast Cancer.

In order to investigate whether AdipoR1 is involved in cell death induced by SET1B depletion in TNBC cells, we designed a pair of CRISPR-Cas9 targeting the promoter region, Exon1 and 2 of AdipoR1 genes in MDA-MB-231 cells (FIG. 13A). According to the PCR genotyping and RNA-seq result, the transcripts of AdipoR1 in the cells are completely silenced (FIG. 13B, C). Interestingly, we found that knocking out of AdipoR1 partially but significantly rescued cell death by loss of SET1B protein by cell counting assay (FIG. 13D) and colony formation assay (FIG. 13E, F). RNA-seq result also revealed that around 46% (67/147) genes regulated by SET1B are controlled by AdipoR1 (FIG. 13G). These results suggested that AdipoR1 is one of the important and major downstream target genes of SET1B/COMPASS. Since TNBC cells are more sensitive to SET1B depletion levels (FIG. 1A), and since SET1B/BOD1 shRNA affects ADIPOR1 expression in both ER-positive and TNBC cells (FIG. 12B), we hypothesized that ADIPOR1 signaling selectively suppresses triple-negative breast cancer cells. To test this hypothesis, we generated multiple cell lines expressing inducible GFP or GFP-ADIPOR1 under the regulation of doxycycline (FIG. 6A). After dox treatment, we found that GFP-ADIPOR1 significantly suppresses the cell growth of both MDA-MB-231 and MDA-MB-468 TNBC cells, while there is no obvious effect on MCF7 cell growth (FIG. 6B, 13H). GFP-ADIPOR1 also inhibits the colony formation ability of triple-negative breast cancer cell lines while there is no effect on MCF7 cells (FIG. 6C, D). Given this observation, we considered treating triple-negative breast cancer cell lines with one of the newly identified ADIPOR1 agonists, AdipoRon, which shows promising results in insulin resistant, type 2 diabetes, and longevity in obese diabetic mouse models. Interestingly, we found that the treatment of AdipoRon significantly inhibited the colony formation ability of multiple triple-negative breast cancer lines (FIG. 6E, F, 13I). Moreover, treatment of AdipoRON does not affect SET1b protein level (FIG. 13J). In order to investigate AdipoRon's potential tumor suppressive effects in vivo for TNBC, we injected LM2 cells into the mammary gland of nude mice, and started the oral treatment of 50 mg/kg AdipoRon 12 days after transplantation (FIG. 14A). Tumor size was measured two times per week. As shown in FIGS. 6G and H, and consistent with the in vitro studies, treatment with AdipoRon significantly reduced tumor size and increased animal survival. We also confirmed the drug effect of AdipoRon by intraperitoneal injection, and got consistent result (FIG. 14C, D) as the oral treatment. Taken together, these results provide novel therapeutic strategy for clinical treatment of human triple negative breast cancer.

Discussion.

In this study, we report SET1B/COMPASS plays a central role in mediating human triple negative breast cancer (TNBC) cells survival and may serve as a potential therapeutic target for the treatment of human TNBC. Specifically, we demonstrated that (1) Loss of SET1B but not SET1A in TNBC cells significantly affects cell survival in vitro and tumor growth in vivo. (2) SET1B regulates expression of a set of genes involved in tumorigenesis without affecting histone modifications. (3) Purification of SET1B and subsequent proteomic analyses identified that the SET1B complex as the only predominantly cytoplasmic COMPASS family member, with BOD1 as its unique cytoplasmic subunit. (4) BOD1 regulates 50% of the genes that are regulated by SET1B, which include genes involved in ADIPOR1 signaling. (5) ADIPOR1, which is activated by SET1B and BOD1 depletion, selectively inhibited TNBC cells survival without affecting ER-positive cell growth, and (6) the newly identified ADIPOR1 agonist remarkably inhibited TNBC cell growth both in vitro and in vivo.

SET1B (KIAA1076 protein) was initially identified based on database analysis for proteins related to yeast Set1 (Lee et al., 2007). Human SET1A and SET1B proteins share 35 and 37% identity with yeast Set1, and the two proteins are 85% identical and 97% similar throughout the catalytic SET and post-SET domains. In in vitro studies, both SET1A and SET1B could methylate histone H3 at Lysine 4, however, in mouse ES cells, SET1A was found to be the major H3K4 methyltransferase, while loss of SET1B did not affect the methylation level of Histone H3K4 (Bledau et al., 2014). Consistent with these results, our ChIP-seq analysis in MDA-MB-231 cells did not detect obvious changes in H3K4me3 levels after depletion of SET1B.

A previous study reported that SET1A mRNA levels were elevated in breast cancer tissues and correlated with lymph node positive patients relapse free survival (Salz et al., 2015). However, by utilizing the latest version of KM plotter, which contains twice the number of samples as the version used in the previous study, we find that SET1A does not correlate with survival of either lymph node positive or negative breast cancer patients. On the contrary, SET1A mRNA levels correlate with improved patient survival according to our analysis, and knockdown of SET1A in breast cancer cell lines did not have a major effect on cell growth. Furthermore, SET1A was shown to cooperate with p300 through direct interactions and coupled histone modifications to facilitate p53 function (Tang et al., 2013), suggesting that SET1A might function as a tumor suppressor in human cells. In contrast, we find that loss of SET1B significantly reduces tumor growth both in vitro and in vivo, and both mRNA and protein levels of SET1B are positively correlated with malignancy.

Several KMTs are found to localize in the cytoplasm and catalyze lysine methylation. For instance, SMYD3 was first characterized as a histone H3K4 methyltransferase in vitro (Hamamoto et al., 2004), and later studies demonstrated that SMYD3 lacks a canonical nuclear localization signal (NLS) and functions as an oncogene in different types of cancers via methylating MAP3K2 at K260 in the cytoplasm (Mazur et al., 2014). Consistent with SET1B depletion not affecting H3K4 methylation, we found that the majority of SET1B is present in the cytoplasm.

In our previous studies, we identified BOD1 (Cps15, SHG1) as a component of COMPASS in yeast that had no obvious effect on H3K4 methylation levels (Krogan et al., 2002). In mammalian cells, BOD1 was found to function as a small kinetochore-associated protein required for mitotic chromosome congression (Porter et al., 2007), and to fine tune PP2A phosphatase activity at the kinetochore to ensure efficient chromosome congression and maintenance of chromatid cohesion (Porter et al., 2013). These findings could explain the cell growth defects we observe after BOD1 depletion. Furthermore, our findings that half of the genes regulated by BOD1 are also regulated by SET1B, and that BOD1-depleted cells exhibit the same morphological changes as SET1B depletion, indicate that the cytoplasmic SET1B/BOD1 complex could be involved in mitotic chromosome congression as well as maintenance of chromatid cohesion.

Adiponectin, an adipose tissue-derived hormone, has been studied intensively for the past decade because of its anti-inflammatory, anti-atherogenic, antidiabetic properties (Kershaw and Flier, 2004). Recent advances suggest that adiponectin also plays an important role in the development and progression of various cancers, especially obesity-related cancers (Surmacz, 2013). Three adiponectin receptors have been identified, ADIPOR1, ADIPOR2 and T-cadherin, with ADIPOR1 being ubiquitously expressed and having the highest binding affinity to adiponectin (Yamauchi et al., 2003). In human breast cancer, multiple studies have reported that low serum adiponectin levels are significantly associated with increased risk (Nagaraju et al., 2016). Lower expression level of ADIPOR1 is also observed in invasive breast cancer samples compared to normal breast tissues, suggesting that ADIPOR1 signaling may exert growth inhibitory effects with the potential to overcome the transformation of pre-invasive to invasive breast cancer (Pfeiler et al., 2010). However, the mechanism(s) by which ADIPOR1 signaling is reduced in invasive breast cancer is unknown, and there is a strong therapeutic interest in reactivating this signaling network.

In our current study, we found that knocking down the subunits of Set1B/COMPASS (SET1B or BOD1) significantly increases the expression of mRNA levels of ADIPOR1 but not ADIPOR2 and this is further observed in TCGA database that in 82 triple negative breast cancer samples, SET1B expression negatively correlates with ADIPOR1 expression at the mRNA level (Data not shown). These results suggest that elevated SET1B/COMPASS reduces ADIPOR1 levels in breast cancer patients. Previous studies have found that adiponectin, the ligand of ADIPOR1, was also reduced in the serum of breast cancer patients (Pfeiler et al., 2010), suggesting a general inactivation of Adiponectin/ADIPOR1 signaling in breast cancer patients. Therefore, reactivating its signaling by re-expressing ADIPOR1 in TNBC cells with an ADIPOR1 agonist or inhibition of SET1B/COMPASS function could potentially be effective therapies for breast cancer.

We found that TNBC cells are much more sensitive to ADIPOR1 protein levels than ER positive cells, indicating that the cell survival defect of elevated ADIPOR1 is at least partially responsible for the phenotype of the selective sensitivity of TNBC cells to SET1B knockdown. Recent studies identified a small molecule named AdipoRon, which is a specific agonist for adiponectin receptors with low toxicity in vivo (Okada-Iwabu et al., 2013). Because ADIPOR1 is suppressed by SET1B in TNBC cells, we believe that treatment with this small molecule could re-activate AdipoR signaling in TNBC cells. Surprisingly, we found that this small molecule developed for Type 2 diabetes also has a dramatic anti-tumor effect in vitro at a lower concentration (10 µM) than the plasma concentration (11.6 µM) of mice treated with 50 mg/kg AdipoRon (Okada-Iwabu et al., 2013). In LM2 breast cancer cell-transplanted nude mice, 12 treatments with 50 mg/kg AdipoRon, significantly reduced tumor growth and significantly increased lifespan.

Emerging evidence has shown that there is close relationship between being over body weight or obese and risk of breast cancer (Anderson et al., 2015; Gathirua-Mwangi et al., 2015; Neuhouser et al., 2015), and it remains unknown how obesity contributes to breast cancer or facilitates breast cancer cell growth and metastasis. Based on previous findings, the adiponectin/AdipoR cascade acts as a key tumor suppressor signaling pathway in human breast cancer. Our study suggests a model (FIG. 7) in which increased cytoplasmic SET1B/COMPASS in breast cancer cells suppresses ADIPOR1 expression, and when coupled with decreased circulating adiponectin in patients, leads to hyper-inactivation of this tumor suppressive network. Taken together, our findings reveal a new oncogenic function of COMPASS in the cytoplasm, and provide a novel therapeutic strategy for reactivating ADIPOR1 signaling in human breast cancer through COMPASS pathway inhibition.

Materials and Methods

Antibodies. HSP90 (sc-7947) and GFP (sc-9996) antibodies were purchased from Santa Cruz, M2 Flag (F3165) antibody was purchased from Sigma, RBBP5 (A300-109A) antibody was from Bethyl Laboratories, ASH2L (#5091) and WDR5 (#13105) antibodies were purchased from Cell Signaling. The anti-SET1A polyclonal antibody was generated with a peptide corresponding to human SET1A amino acids 1240-1444, anti-SET1B polyclonal antibody was generated with the peptide corresponding to human SET1B amino acids 1407-1627. Anti-MLL3 was generated against human MLL3 amino acids 1-200 and anti-MLL4 was generated as described before.

Cell Lines and RNA Interference.

MCF7, T47D, BT549, Hs578t, MDA-MB-468 cells were obtained from ATCC, and maintained with DMEM (Gibco, Gaithersburg, Md.) containing 10% FBS (Sigma). LM2 cells (derived from MDA-MB-231 cells) were kindly provided by Dr. Yibin Kang. The cells were infected with lentivirus containing short-hairpin RNAs in the presence of 4 μg/ml Polybrene (Sigma) for 24 hr in DMEM supplemented with 10% FBS. The infected cells were selected with 2 μg/ml puromycin for an extra 48 hours before harvest. The shRNA constructs were purchased from Sigma. The clone IDs for SET1B are TRCN0000237963 (shSET1B-#1) and TRCN0000237965 (shSET1B-#2), clone IDs for SET1A is TRCN0000153348, clone IDs for BOD1 are TRCN0000168741 and TRCN0000167057, clone IDs for FOXQ1 are TRCN0000431639 and TRCN0000017924, clone IDs for ELKS are TRCN0000013880 and TRCN0000013878, clone IDs for CCNJ are TRCN0000045232 and TRCN0000045229. The non-targeting (shCtrl) shRNA construct (SHC002) was purchased from Sigma.

Crystal Violet Staining.

Cells were stained with 0.5% crystal violet staining solution, and incubate for 20 min at room temperature on a bench rocker with a frequency of 20 oscillations per minute. Then wash the plate four times in a stream of tap water followed by air-dry for 2 hours, RT. Then add 200 μL of methanol to each well, and incubate the plate with its lid on for 20 min at room temperature on a bench rocker with a frequency of 20 oscillations per minute and measure the optical density of each well at 570 nm (OD570) with a plate reader.

Mass Spectrometry.

For Orbitrap Fusion Tribrid MS analysis, the tryptic peptides were purified with Pierce C18 spin columns (Thermo Scientific). Three micrograms of each fraction was auto-sampler loaded with a Thermo EASY nLC 1000 UPLC pump onto a vented Acclaim Pepmap 100, 75 um×2 cm, nanoViper trap column coupled to a nanoViper analytical column (Thermo-164570, 3 μm, 100 Å, C18, 0.075 mm, 500 mm) with stainless steel emitter tip assembled on the Nanospray Flex Ion Source with a spray voltage of 2000V. Buffer A contained 94.785% $H_2O$ with 5% ACN and 0.125% FA, and buffer B contained 99.875% ACN with 0.125% FA. The chromatographic run was for 2 hours in total with the following profile: 0-7% for 3 minutes, 10% for 3 minutes, 25% for 80 minutes, 33% for 20 minutes, 50% for 3 minutes, 95% for 3 minutes and again 95% for 8 minutes. Additional MS parameters include: Ion transfer tube temp=300° C., Easy-IC internal mass calibration, default charge state=2 and cycle time=3 seconds. Detector type set to Orbitrap, with 60K resolution, with wide quad isolation, mass range=normal, scan range=300-1500 (m/z), max injection time=50 ms, AGC target=200,000, microscans=1, S-lens RF level=60, without source fragmentation, and datatype=centroid. MIPS was set as on, included charge states=2-6 (reject unassigned). Dynamic exclusion enabled with n=1 for 30 seconds and 45 second exclusion duration at 10 ppm for high and low. Precursor selection decision=most intense, top 20, isolation window=1.6, scan range=auto normal, first mass=110, collision energy 30%, CID, Detector type=ion trap, OT resolution=30K, IT scan rate=rapid, max injection time=75 ms, AGC target=10,000, Q=0.25, inject ions for all available parallelizable time.

Tandem Mass Spectra Analysis.

Spectrum raw files from samples were extracted into ms1 and ms2 files using in-house program RawXtractor or RawConverter available from the laboratory of John R Yates III at the Scripps Research Institute (He et al., 2015), and the tandem mass spectra were searched against UniProt human protein database (downloaded on Mar. 25, 2014) (The UniProt Consortium 2015) and matched to sequences using the ProLuCID/SEQUEST algorithm (ProLuCID ver. 3.1) (Eng et al., 1994; Xu et al., 2015) with 50 ppm peptide mass tolerance for precursor ions and 600 ppm for fragment ions. The search space included all fully and half-tryptic peptide candidates that fell within the mass tolerance window with no miscleavage constraint, assembled and filtered with DTASelect2 (ver. 2.1.3) (Cociorva et al., 2007; Tabb et al., 2002) through Integrated Proteomics Pipeline (IP2 v.3, Integrated Proteomics Applications, Inc., CA, USA http://www.integratedproteomics.com). To estimate peptide probabilities and false-discovery rates (FDR) accurately, we used a target/decoy database containing the reversed sequences of all the proteins appended to the target database (Elias and Gygi, 2007). Each protein identified was required to have a minimum of one peptide of minimal length of six amino acid residues and within 10 ppm of the expected m/z. However, this peptide had to be an excellent match with a FDR less than 0.001 and at least one excellent peptide match. After the peptide/spectrum matches (PSM) were filtered, we estimated that the protein FDRs were ≤1% for each sample analysis.

ChIP-Seq.

$5 \times 10^7$ cells were used for each ChIP assay, as performed as previously described (Chen et al., 2015). ChIP-sequencing libraries were prepared with Illumina's Tru-seq DNA sample prep kit.

ChIP-Seq Analysis.

ChIP-seq reads were aligned to the human genome (UCSC hg19) for MDA-MB-231 cells, using Bowtie version 1.0.0 (Langmead et al., 2009). Only uniquely mapping reads with up to two mismatches within the entire length of the read were considered for further analysis. The resulting reads were extended to 150 bases toward the interior of the sequenced fragment and were normalized to total reads aligned (reads per million, rpm). Peak detection for H3K4me1, H3K4me3 and Pol II were done with MACS (model-based analysis of ChIP-Seq) (Zhang et al., 2008) version 1.4.2 using default parameters. Gene annotations from Ensembl release 72 were used.

RNA-Seq Analysis.

Total RNA was extracted from trizol according to the manufacturer's instructions. Then total RNA was treated with DNase I and cleaned with the QIAGEN RNeasy mini kit. 500 ng RNA was used for library preparation with TruSeq Stranded Total RNA with Ribo-Zero Gold kit (Illumina, RS-123-2201). The sequenced reads were aligned to the human genome (UCSC hg19) with TopHat v2.0.9 (Trapnell et al., 2009). To evaluate differential gene expression, gene count tables were constructed using Ensembl gene annotations and used as input into edgeR 3.0.8 (Robinson et al., 2010). Adjusted p values were computed using the Benjamini-Hochburg method. Protein coding genes, long non-coding RNA and pseudogenes with adjusted p values less than 0.01 were used for the downstream analysis with Metascape. P values for Venn diagrams were performed with the hypergeometric test.

Animal Experiments.

All animal work was performed in accordance with protocols approved by The Center for Comparative Medicine (CCM) of Northwestern University. Athymic nude mice at 5-6 weeks old were used for xenograft experiments. For tumor growth assay, $4 \times 10^6$ breast cancer cells were inoculated into the fat pad of nude mice. Tumor growth was monitored every other day two weeks after inoculation. For treatment assay, $4 \times 10^6$ breast cancer cells were inoculated into the fat pad of nude mice. 12 days after injection, when the tumor reached to 100 mm$^3$, mice were randomly divided into two groups. They were treated with either PBS or AdipoRon (50 mg/kg) for 10 times, and the tumor size (G) and animal survival (H) was monitored. Tumor growth was measured two weeks after inoculation

REFERENCES

Anderson, A. S., Key, T. J., Norat, T., Scoccianti, C., Cecchini, M., Berrino, F., Boutron-Ruault, M. C., Espina, C., Leitzmann, M., Powers, H., et al. (2015). European Code against Cancer 4th Edition: Obesity, body fatness and cancer. Cancer Epidemiol 39 Suppl 1, S34-45.

Bauer, K. R., Brown, M., Cress, R. D., Parise, C. A., and Caggiano, V. (2007). Descriptive analysis of estrogen receptor (ER)-negative, progesterone receptor (PR)-negative, and HER2-negative invasive breast cancer, the so-called triple-negative phenotype: a population-based study from the California cancer Registry. Cancer 109, 1721-1728.

Bledau, A. S., Schmidt, K., Neumann, K., Hill, U., Ciotta, G., Gupta, A., Tones, D. C., Fu, J., Kranz, A., Stewart, A. F., et al. (2014). The H3K4 methyltransferase Setd1a is first required at the epiblast stage, whereas Setd1b becomes essential after gastrulation. Development 141, 1022-1035.

Bremer, K., Kocha, K. M., Snider, T., and Moyes, C. D. (2015). Sensing and responding to energetic stress: The role of the AMPK-PGC1alpha-NRF1 axis in control of mitochondrial biogenesis in fish. Comp Biochem Physiol B Biochem Mol Biol.

Chen, F. X., Woodfin, A. R., Gardini, A., Rickels, R. A., Marshall, S. A., Smith, E. R., Shiekhattar, R., and Shilatifard, A. (2015). PAF1, a Molecular Regulator of Promoter-Proximal Pausing by RNA Polymerase II. Cell 162, 1003-1015.

Cho, Y. W., Hong, T., Hong, S., Guo, H., Yu, H., Kim, D., Guszczynski, T., Dressler, G. R., Copeland, T. D., Kalkum, M., et al. (2007). PTIP associates with MLL3- and MLL4-containing histone H3 lysine 4 methyltransferase complex. The Journal of biological chemistry 282, 20395-20406.

Cociorva, D., D, L. T., and Yates, J. R. (2007). Validation of tandem mass spectrometry database search results using DTASelect. Current protocols in bioinformatics/editoral board, Andreas D. Baxevanis . . . [et al.] Chapter 13, Unit 13 14.

Dent, R., Trudeau, M., Pritchard, K. I., Hanna, W. M., Kahn, H. K., Sawka, C. A., Lickley, L. A., Rawlinson, E., Sun, P., and Narod, S. A. (2007). Triple-negative breast cancer: clinical features and patterns of recurrence. Clin Cancer Res 13, 4429-4434.

Elias, J. E., and Gygi, S. P. (2007). Target-decoy search strategy for increased confidence in large-scale protein identifications by mass spectrometry. Nature methods 4, 207-214.

Eng, J. K., McCormack, A. L, and Yates, J. R. (1994). An approach to correlate tandem mass spectral data of peptides with amino acid sequences in a protein database. Journal of the American Society for Mass Spectrometry 5, 976-989.

Ferguson, A. D., Larsen, N. A., Howard, T., Pollard, H., Green, I., Grande, C., Cheung, T., Garcia-Arenas, R., Cowen, S., Wu, J., et al. (2011). Structural basis of substrate methylation and inhibition of SMYD2. Structure 19, 1262-1273.

Gathirua-Mwangi, W. G., Zollinger, T. W., Murage, M. J., Pradhan, K. R., and Champion, V. L. (2015). Adult BMI change and risk of Breast Cancer: National Health and Nutrition Examination Survey (NHANES) 2005-2010. Breast Cancer 22, 648-656.

Hamamoto, R, Furukawa, Y., Morita, M., Iimura, Y., Silva, F. R, Li, M., Yagyu, R, and Nakamura, Y. (2004). SMYD3 encodes a histone methyltransferase involved in the proliferation of cancer cells. Nature cell biology 6, 731-740.

He, L., Diedrich, J., Chu, Y. Y., and Yates, J. R., 3rd (2015). Extracting Accurate Precursor Information for Tandem Mass Spectra by RawConverter. Analytical chemistry 87, 11361-11367.

Herz, H. M., Hu, D., and Shilatifard, A. (2014). Enhancer malfunction in cancer. Molecular cell 53, 859-866.

Kandoth, C., McLellan, M. D., Vandin, F., Ye, K., Niu, B., Lu, C., Xie, M., Zhang, Q., McMichael, J. F., Wyczalkowski, M. A., et al. (2013). Mutational landscape and significance across 12 major cancer types. Nature 502, 333-339.

Kershaw, E. E., and Flier, J. S. (2004). Adipose tissue as an endocrine organ. J Clin Endocr Metab 89, 2548-2556.

Klaus, C. R., Iwanowicz, D., Johnston, D., Campbell, C. A., Smith, J. J., Moyer, M. P., Copeland, R. A., Olhava, E. J., Scott, M. P., Pollock, R. M., et al. (2014). DOT1L inhibitor EPZ-5676 displays synergistic antiproliferative activity in combination with standard of care drugs and hypomethylating agents in MLL-rearranged leukemia cells. J Pharmacol Exp Ther 350, 646-656.

Kotake, Y., Cao, R., Viatour, P., Sage, J., Zhang, Y., and Xiong, Y. (2007). pRB family proteins are required for H3K27 trimethylation and Polycomb repression complexes binding to and silencing p16INK4alpha tumor suppressor gene. Genes Dev 21, 49-54.

Kouzarides, T. (2007). Chromatin modifications and their function. Cell 128, 693-705.

Krogan, N. J., Dover, J., Khorrami, S., Greenblatt, J. F., Schneider, J., Johnston, M., and Shilatifard, A. (2002). COMPASS, a histone H3 (Lysine 4) methyltransferase required for telomeric silencing of gene expression. The Journal of biological chemistry 277, 10753-10755.

Kubicek, S., O'Sullivan, R. J., August, E. M., Hickey, E. R., Zhang, Q., Teodoro, M. L., Rea, S., Mechtler, K., Kowalski, J. A., Homon, C. A., et al. (2007). Reversal of H3K9me2 by a small-molecule inhibitor for the G9a histone methyltransferase. Mol Cell 25, 473-481.

Langmead, B., Trapnell, C., Pop, M., and Salzberg, S. L. (2009). Ultrafast and memory-efficient alignment of short DNA sequences to the human genome. Genome biology 10, R25.

Lee, J. H., and Skalnik, D. G. (2012). Rbm15-Mkl1 interacts with the Setd1b histone H3-Lys4 methyltransferase via a SPOC domain that is required for cytokine-independent proliferation. PLoS One 7, e42965.

Lee, J. H., Tate, C. M., You, J. S., and Skalnik, D. G. (2007). Identification and characterization of the human Set1B histone H3-Lys4 methyltransferase complex. The Journal of biological chemistry 282, 13419-13428.

Mazur, P. K., Reynoird, N., Khatri, P., Jansen, P. W., Wilkinson, A. W., Liu, S., Barbash, O., Van Aller, G. S., Huddleston, M., Dhanak, D., et al. (2014). SMYD3 links lysine methylation of MAP3K2 to Ras-driven cancer. Nature 510, 283-287.

Miller, T., Krogan, N. J., Dover, J., Erdjument-Bromage, H., Tempst, P., Johnston, M., Greenblatt, J. F., and Shilatifard, A. (2001). COMPASS: a complex of proteins associated with a trithorax-related SET domain protein. Proceedings of the National Academy of Sciences of the United States of America 98, 12902-12907.

Mohan, M., Herz, H. M., and Shilatifard, A. (2012). SnapShot: Histone lysine methylase complexes. Cell 149, 498-498 e491.

Nagaraju, G. P., Rajitha, B., Aliya, S., Kotipatruni, R. P., Madanraj, A. S., Hammond, A., Park, D., Chigurupati, S., Alam, A., and Pattnaik, S. (2016). The role of adiponectin in obesity-associated female-specific carcinogenesis. Cytokine & growth factor reviews.

Neuhouser, M. L., Aragaki, A. K., Prentice, R. L., Manson, J. E., Chlebowski, R., Carty, C. L., Ochs-Balcom, H. M., Thomson, C. A., Caan, B. J., Tinker, L. F., et al. (2015). Overweight, Obesity, and Postmenopausal Invasive Breast Cancer Risk: A Secondary Analysis of the Women's Health Initiative Randomized Clinical Trials. JAMA Oncol 1, 611-621.

Okada-Iwabu, M., Yamauchi, T., Iwabu, M., Honma, T., Hamagami, K., Matsuda, K., Yamaguchi, M., Tanabe, H., Kimura-Someya, T., Shirouzu, M., et al. (2013). A smallmolecule AdipoR agonist for type 2 diabetes and short life in obesity. Nature 503, 493-499.

Pfeiler, G., Hudelist, G., Wulfing, P., Mattsson, B., Konigsberg, R., Kubista, E., and Singer, C. F. (2010). Impact of AdipoR1 expression on breast cancer development. Gynecologic oncology 117, 134-138.

Piunti, A., and Shilatifard, A. (2016). Epigenetic balance of gene expression by Polycomb and COMPASS families. Science 352, aad9780.

Porter, I. M., McClelland, S. E., Khoudoli, G. A., Hunter, C. J., Andersen, J. S., McAinsh, A D., Blow, J. J., and Swedlow, J. R. (2007). Bod1, a novel kinetochore protein required for chromosome biorientation. The Journal of cell biology 179, 187-197.

Porter, I. M., Schleicher, K., Porter, M., and Swedlow, J. R. (2013). Bod1 regulates protein phosphatase 2A at mitotic kinetochores. Nat Commun 4.

Robinson, M. D., McCarthy, D. J., and Smyth, G. K. (2010). edgeR: a Bioconductor package for differential expression analysis of digital gene expression data. Bioinformatics 26, 139-140.

Rouzier, R., Perou, C. M., Symmans, W. F., Ibrahim, N., Cristofanilli, M., Anderson, K., Hess, K. R., Stec, J., Ayers, M., Wagner, P., et al. (2005). Breast cancer molecular subtypes respond differently to preoperative chemotherapy. Clin Cancer Res 11, 5678-5685.

Salz, T., Deng, C. W., Pampo, C., Siemann, D., Qiu, Y., Brown, K., and Huang, S. M. (2015). Histone Methyltransferase hSETD1A Is a Novel Regulator of Metastasis in Breast Cancer. Mol Cancer Res 13, 461-469.

Salz, T., Li, G., Kaye, F., Thou, L., Qiu, Y., and Huang, S. (2014). hSETD1A regulates Wnt target genes and controls tumor growth of colorectal cancer cells. Cancer research 74, 775-786.

Shilatifard, A. (2012). The COMPASS family of histone H3K4 methylases: mechanisms of regulation in development and disease pathogenesis. Annu Rev Biochem 81, 65-95.

Surmacz, E. (2013). Leptin and adiponectin: emerging therapeutic targets in breast cancer. Journal of mammary gland biology and neoplasia 18, 321-332.

Tabb, D. L, McDonald, W. H., and Yates, J. R., 3rd (2002). DTASelect and Contrast: tools for assembling and comparing protein identifications from shotgun proteomics. Journal of proteome research 1, 21-26.

Takahashi, Y. H., Westfield, G. H., Oleskie, A. N., Trievel, R. C., Shilatifard, A., and Skiniotis, G. (2011). Structural analysis of the core COMPASS family of histone H3K4 methylases from yeast to human. Proceedings of the National Academy of Sciences of the United States of America 108, 20526-20531.

Tang, Z. Y., Chen, W. Y., Shimada, M., Nguyen, U. T. T., Kim, J., Sun, X. J., Sengoku, T., McGinty, R. K., Fernandez, J. P., Muir, T. W., et al. (2013). SET1 and p300 Act Synergistically, through Coupled Histone Modifications, in Transcriptional Activation by p53. Cell 154, 297-310.

Trapnell, C., Pachter, L., and Salzberg, S. L. (2009). TopHat: discovering splice junctions with RNA-Seq. Bioinformatics 25, 1105-1111.

Tripathi, S., Pohl, M. O., Thou, Y., Rodriguez-Frandsen, A., Wang, G., Stein, D. A., Moulton, H. M., DeJesus, P., Che, J., Mulder, L. C., et al. (2015). Meta- and Orthogonal Integration of Influenza "OMICs" Data Defines a Role for UBR4 in Virus Budding. Cell host & microbe 18, 723-735.

Wu, M., Wang, P. F., Lee, J. S., Martin-Brown, S., Florens, L, Washburn, M., and Shilatifard, A. (2008). Molecular regulation of H3K4 trimethylation by Wdr82, a component of human Set1/COMPASS. Molecular and cellular biology 28, 7337-7344.

Xu, T., Park, S. K., Venable, J. D., Wohlschlegel, J. A., Diedrich, J. K., Cociorva, D., Lu, B., Liao, L., Hewel, J., Han, X., et al. (2015). ProLuCID: An improved SEQUEST-like algorithm with enhanced sensitivity and specificity. Journal of proteomics 129, 16-24.

Yamauchi, T., Kamon, J., Ito, Y., Tsuchida, A., Yokomizo, T., Kita, S., Sugiyama, T., Miyagishi, M., Hara, K., Tsunoda, M., et al. (2003). Cloning of adiponectin receptors that mediate antidiabetic metabolic effects. Nature 423, 762-769.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for inhibiting tumor growth of a cancer characterized by expression of Set1B/COMPASS in a subject in need thereof, the method comprising administering to the subject a therapeutic amount of a compound having a formula:

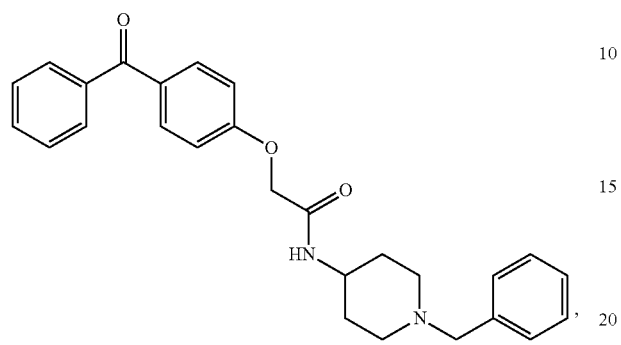

wherein the cancer is triple negative breast cancer (TNBC).

2. A method for inhibiting tumor growth of triple negative breast cancer (TNBC) in a subject in need thereof, the method comprising administering to the subject a therapeutic amount of a compound having a formula:

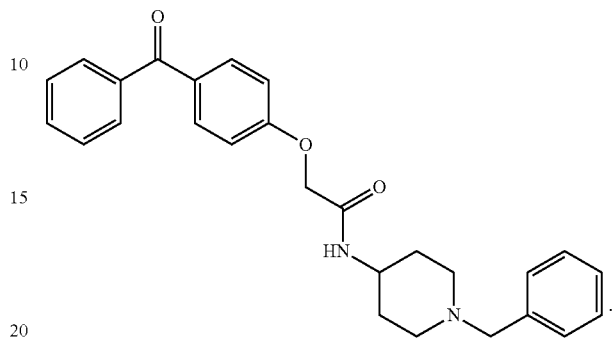

* * * * *